United States Patent
Brenner et al.

(10) Patent No.: US 9,232,947 B2
(45) Date of Patent: Jan. 12, 2016

(54) CLOSURE DEVICE AND METHOD

(75) Inventors: Jacob S. Brenner, Menlo Park, CA (US); Gregory A. Magee, Menlo Park, CA (US); Ruey Feng Peh, Singapore (SG); Erika I. Palmer, Menlo Park, CA (US)

(73) Assignee: THE BOARD OF TRUSTEES OF THE LELAND STANFORD JUNIOR UNIVERSITY, Palo Alto, CA (US)

( * ) Notice: Subject to any disclaimer, the term of this patent is extended or adjusted under 35 U.S.C. 154(b) by 1028 days.

(21) Appl. No.: 13/201,079

(22) PCT Filed: Feb. 17, 2010

(86) PCT No.: PCT/US2010/000470
§ 371 (c)(1),
(2), (4) Date: Nov. 23, 2011

(87) PCT Pub. No.: WO2010/096174
PCT Pub. Date: Aug. 26, 2010

(65) Prior Publication Data
US 2012/0059394 A1    Mar. 8, 2012

Related U.S. Application Data

(60) Provisional application No. 61/153,278, filed on Feb. 17, 2009, provisional application No. 61/220,742, filed on Jun. 26, 2009, provisional application No. 61/266,981, filed on Dec. 4, 2009.

(51) Int. Cl.
*A61B 17/10* (2006.01)
*A61B 17/12* (2006.01)
(Continued)

(52) U.S. Cl.
CPC ....... *A61B 17/12013* (2013.01); *A61B 1/00087* (2013.01); *A61B 1/012* (2013.01);
(Continued)

(58) Field of Classification Search
CPC .............. A61B 17/04; A61B 17/0469; A61B 17/0487; A61B 17/0644; A61B 17/072; A61B 2017/306
USPC .......................................... 606/213, 216, 221
See application file for complete search history.

(56) References Cited

U.S. PATENT DOCUMENTS

| 4,493,319 A | 1/1985 | Polk et al. |
| 4,513,746 A | 4/1985 | Aranyi et al. |

(Continued)

FOREIGN PATENT DOCUMENTS

| DE | 9205453 U1 | 6/1992 |
| EP | 0136949 | 10/1985 |

(Continued)

OTHER PUBLICATIONS

Office Action from the Chinese Patent Office dated Jan. 7, 2014 for corresponding Japanese Application No. P2011-550138, 7 pages.
(Continued)

*Primary Examiner* — Gregory Anderson
(74) *Attorney, Agent, or Firm* — William A. English; Vista IP Law Group LLP

(57) ABSTRACT

Devices and methods for treatment of prolapsed hemorrhoidal arteries is disclosed. The devices can identify the hemorrhoid and ligate the artery without causing significant pain or distension of the rectum. The artery can be identified with ultrasound. The ligation can be performed using energy and/or mechanical structures, such as clips or rubber bands.

16 Claims, 46 Drawing Sheets

(51) Int. Cl.
*A61B 1/00* (2006.01)
*A61B 1/012* (2006.01)
*A61B 1/31* (2006.01)
*A61B 5/00* (2006.01)
*A61B 8/06* (2006.01)
*A61B 8/12* (2006.01)
*A61B 17/064* (2006.01)
*A61B 17/122* (2006.01)
*A61B 17/128* (2006.01)
*A61B 17/04* (2006.01)
*A61B 17/072* (2006.01)
*A61B 18/02* (2006.01)
*A61B 18/08* (2006.01)
*A61B 18/14* (2006.01)
*A61B 17/00* (2006.01)
*A61B 17/06* (2006.01)
*A61B 17/29* (2006.01)
*A61B 17/30* (2006.01)
*A61B 17/34* (2006.01)
*A61B 18/00* (2006.01)
*A61B 19/00* (2006.01)
*A61N 7/02* (2006.01)

(52) U.S. Cl.
CPC ............ *A61B 1/31* (2013.01); *A61B 5/415* (2013.01); *A61B 5/418* (2013.01); *A61B 8/06* (2013.01); *A61B 8/12* (2013.01); *A61B 17/0644* (2013.01); *A61B 17/122* (2013.01); *A61B 17/1227* (2013.01); *A61B 17/1285* (2013.01); *A61B 18/1485* (2013.01); *A61B 5/489* (2013.01); *A61B 17/04* (2013.01); *A61B 17/0469* (2013.01); *A61B 17/0487* (2013.01); *A61B 17/072* (2013.01); *A61B 18/02* (2013.01); *A61B 18/08* (2013.01); *A61B 18/1477* (2013.01); *A61B 2017/00106* (2013.01); *A61B 2017/00867* (2013.01); *A61B 2017/0417* (2013.01); *A61B 2017/06176* (2013.01); *A61B 2017/12018* (2013.01); *A61B 2017/2927* (2013.01); *A61B 2017/306* (2013.01); *A61B 2017/308* (2013.01); *A61B 2017/3452* (2013.01); *A61B 2018/005* (2013.01); *A61B 2018/0022* (2013.01); *A61B 2018/00029* (2013.01); *A61B 2018/00214* (2013.01); *A61B 2018/00267* (2013.01); *A61B 2018/00291* (2013.01); *A61B 2018/00642* (2013.01); *A61B 2018/00982* (2013.01); *A61B 2018/1425* (2013.01); *A61B 2018/1465* (2013.01); *A61B 2018/1495* (2013.01); *A61B 2018/1497* (2013.01); *A61B 2019/304* (2013.01); *A61B 2218/002* (2013.01); *A61N 7/022* (2013.01)

(56) References Cited

U.S. PATENT DOCUMENTS

| | | |
|---|---|---|
| 4,548,201 A | 10/1985 | Yoon |
| 4,566,620 A | 1/1986 | Green et al. |
| 4,794,927 A | 1/1989 | Yoon |
| 4,860,746 A | 8/1989 | Yoon |
| 5,156,315 A | 10/1992 | Green et al. |
| 5,570,692 A * | 11/1996 | Morinaga ............ 600/453 |
| 6,936,005 B2 | 8/2005 | Poff et al. |
| 6,936,055 B1 | 8/2005 | Ken et al. |
| 7,037,314 B2 | 5/2006 | Armstrong |
| 7,896,895 B2 * | 3/2011 | Boudreaux et al. ........ 606/157 |
| 2002/0062130 A1 | 5/2002 | Jugenheimer et al. |
| 2003/0069592 A1* | 4/2003 | Adams et al. ............ 606/142 |
| 2004/0138527 A1* | 7/2004 | Bonner et al. ............ 600/114 |
| 2005/0277945 A1 | 12/2005 | Saadat et al. |
| 2006/0167473 A1 | 7/2006 | Scheyer |
| 2006/0259041 A1 | 11/2006 | Hoffman et al. |
| 2006/0264706 A1 | 11/2006 | Piskun |
| 2008/0058786 A1 | 3/2008 | Boyden et al. |
| 2008/0281267 A1 | 11/2008 | Mehier |
| 2010/0331862 A1* | 12/2010 | Monassevitch et al. ...... 606/142 |

FOREIGN PATENT DOCUMENTS

| | | |
|---|---|---|
| JP | H01139050 | 5/1989 |
| JP | H07184901 | 7/1995 |
| JP | H114833 | 1/1999 |
| JP | 2002520113 | 7/2002 |
| WO | WO-01/91646 A1 | 12/2001 |
| WO | WO-2007/093198 A1 | 8/2007 |
| WO | WO2008/081436 A2 | 7/2008 |

OTHER PUBLICATIONS

International Search Report dated Jun. 10, 2010 for Application PCT/US2010/000470.

Office Action from Japanese Patent Office for corresponding Japanese application No. P2011-550138, Nov. 10, 2014, 6 pages.

* cited by examiner

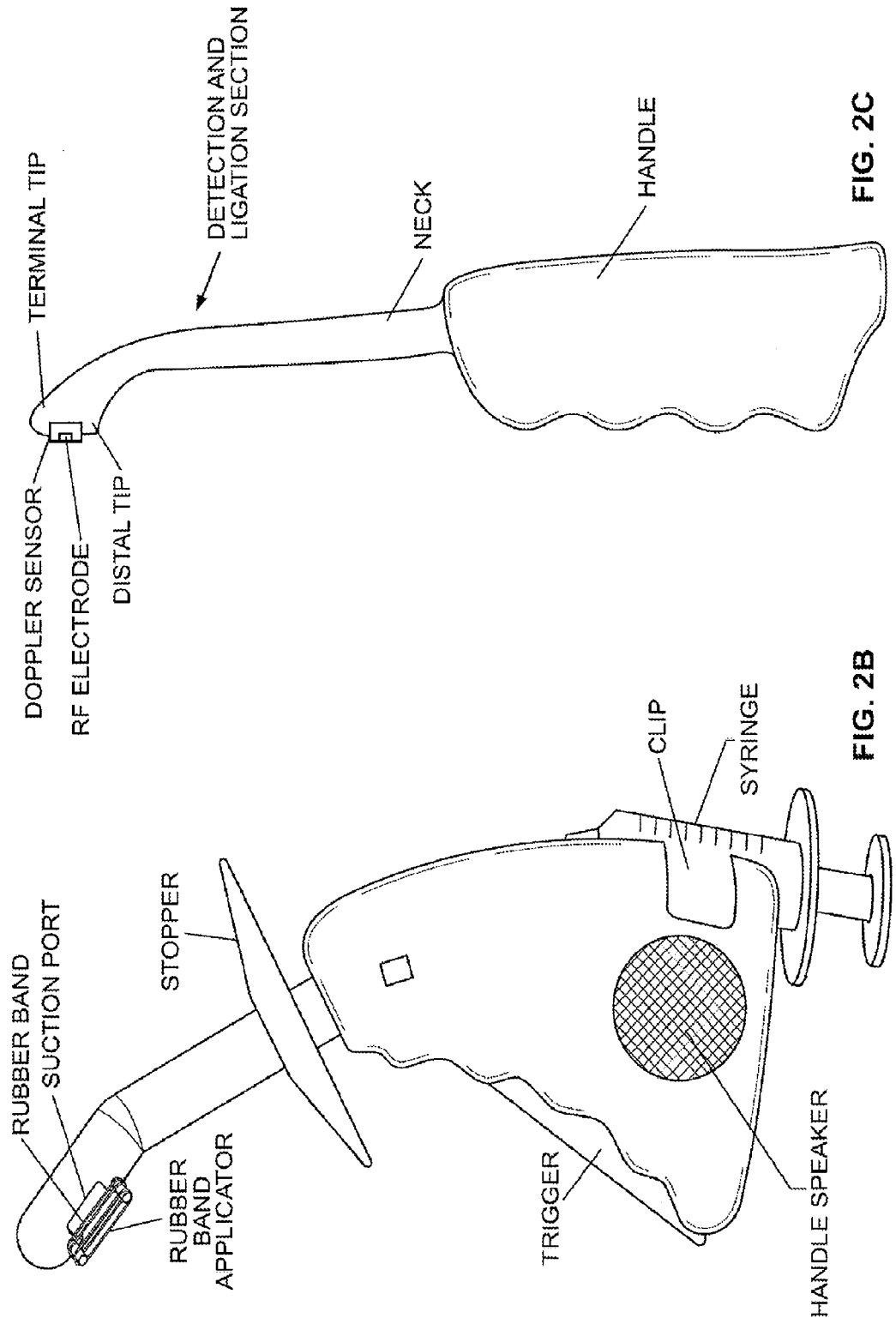

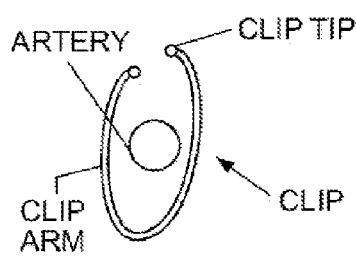 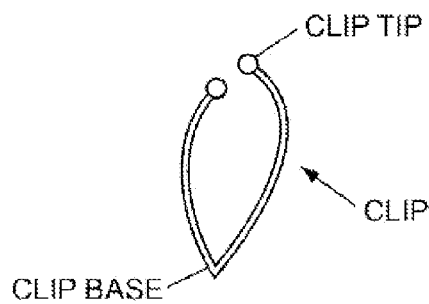 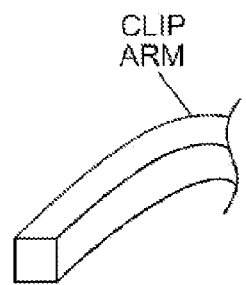
FIG. 6A  FIG. 6B  FIG. 6C
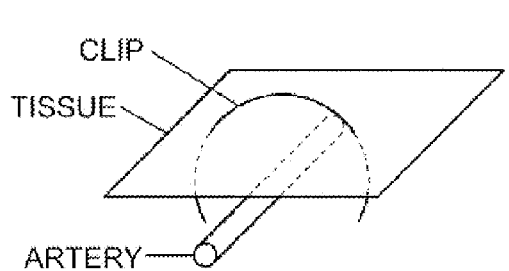 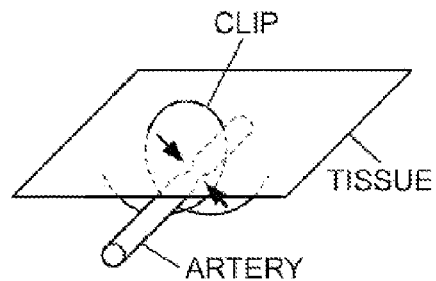
FIG. 7A  FIG. 7B
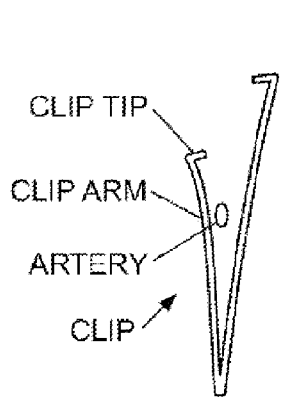 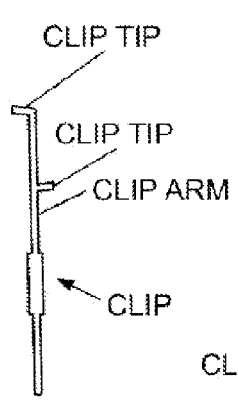  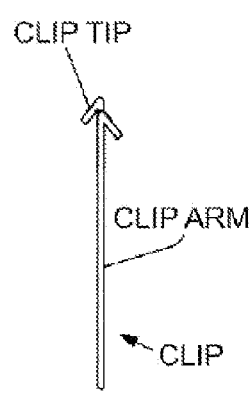
FIG. 8A  FIG. 8B  FIG. 8C  FIG. 8D

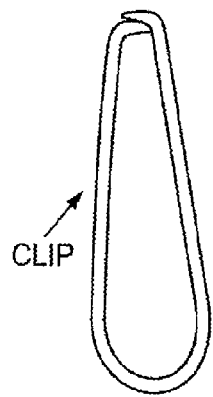 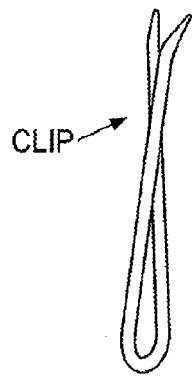 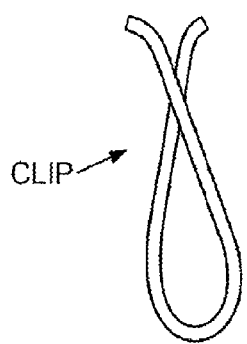 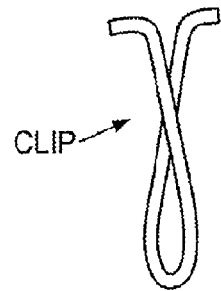
FIG. 10A    FIG. 10B    FIG. 10C    FIG. 10D
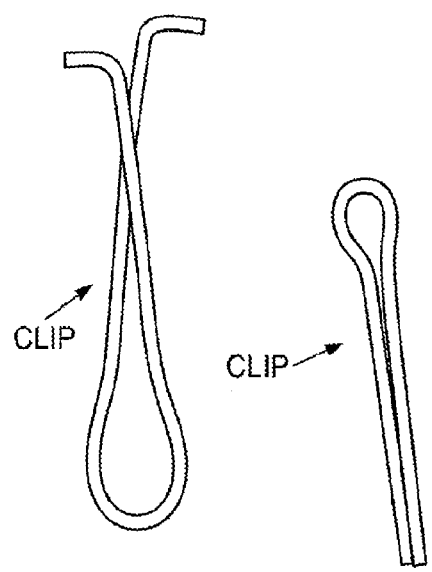
FIG. 10E    FIG. 10A'

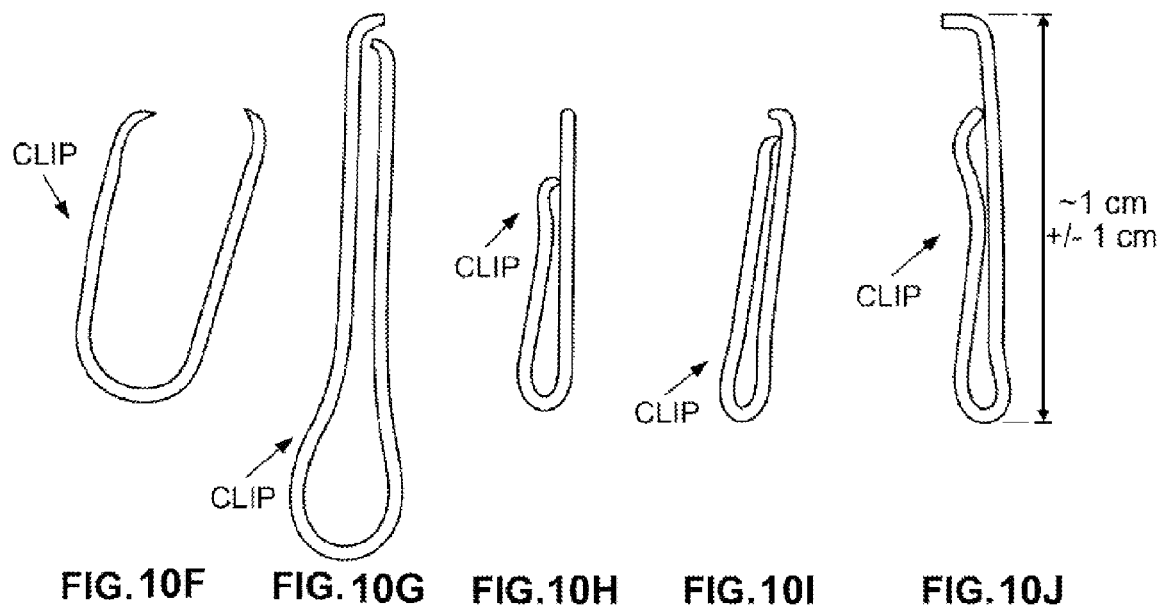

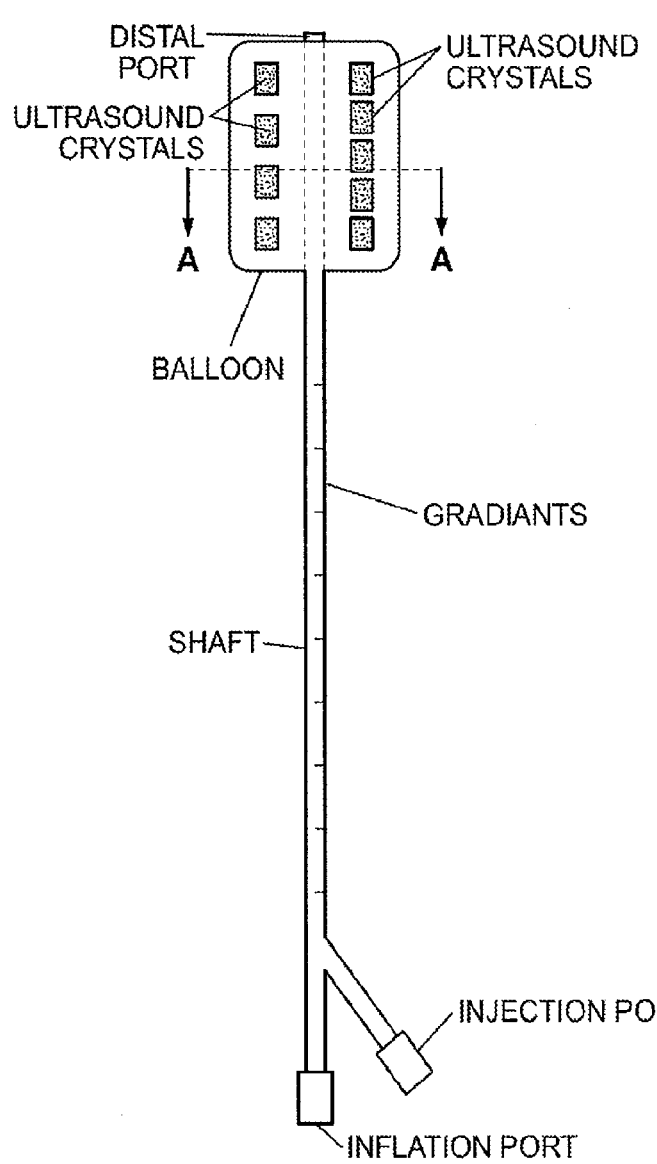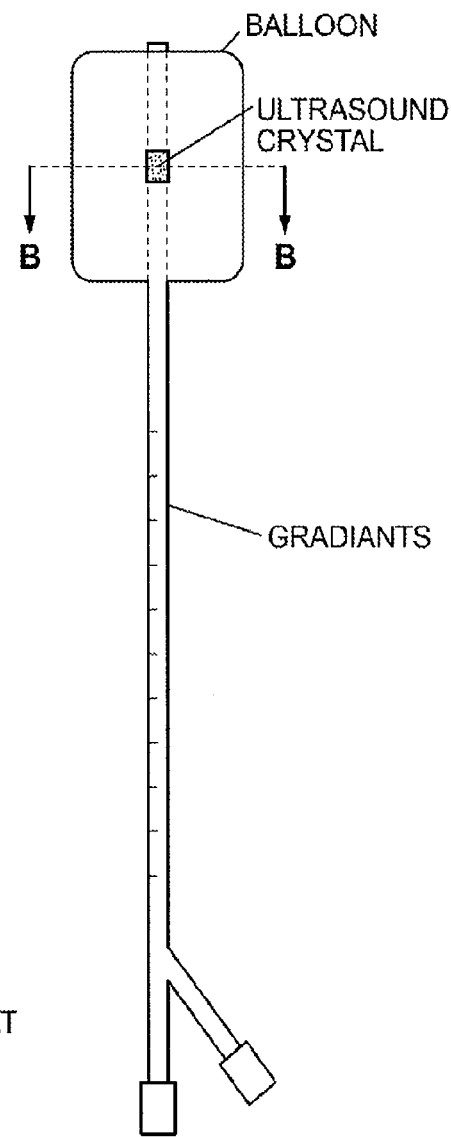
FIG. 14A
FIG. 14C
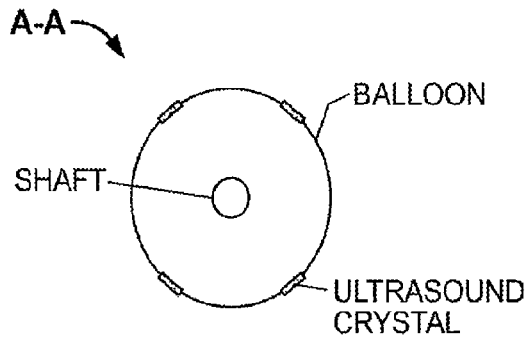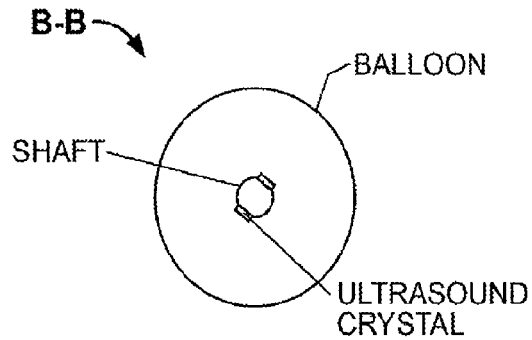
FIG. 14B
FIG. 14D

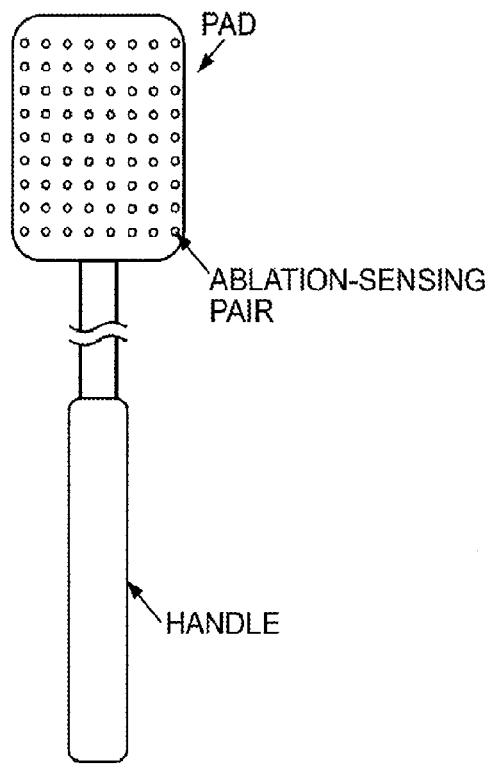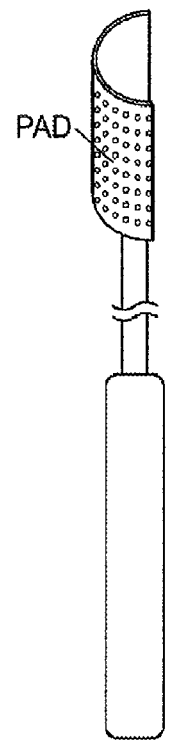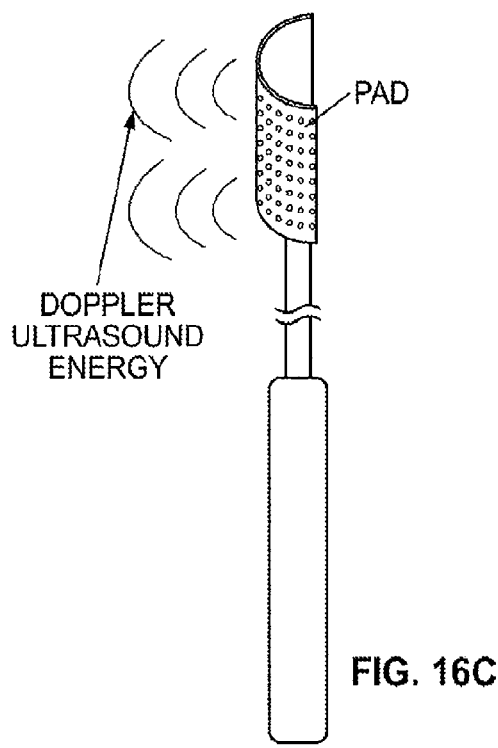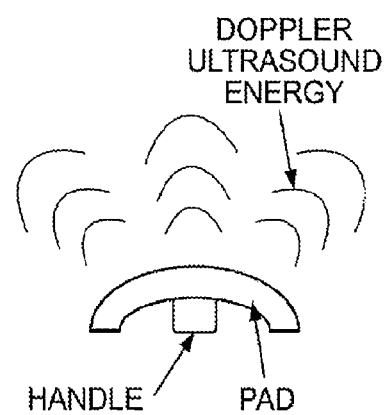
FIG. 16A
FIG. 16B
FIG. 16C
FIG. 16D

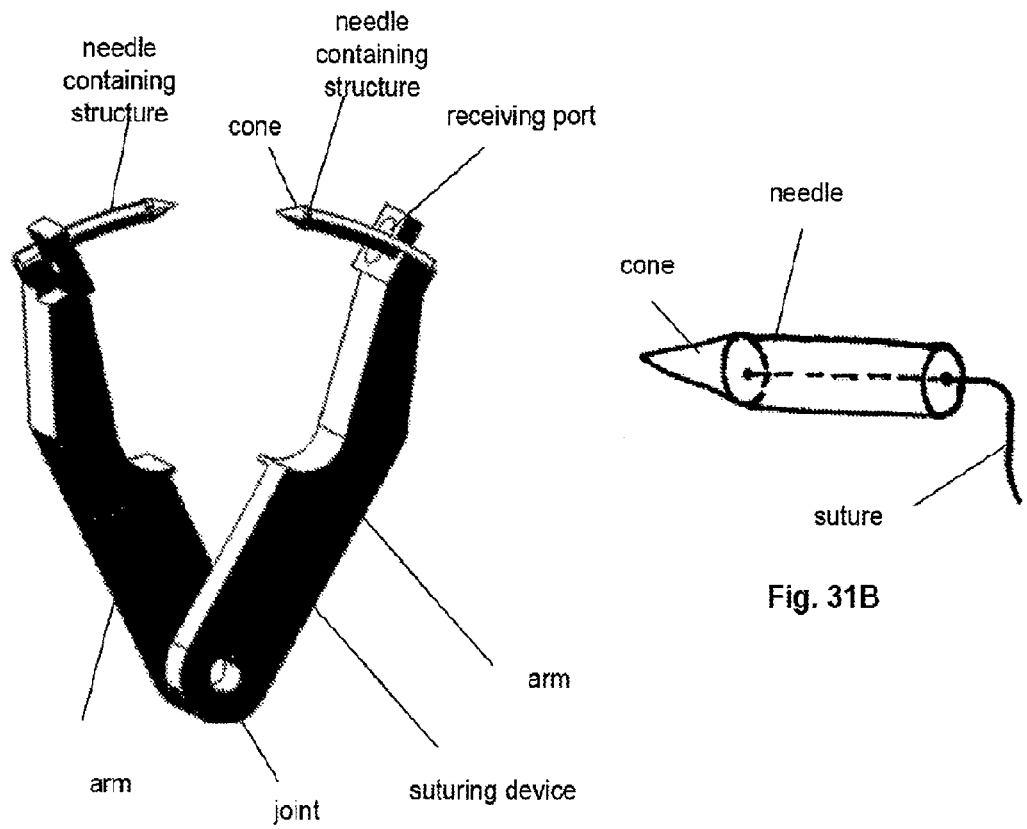
Fig. 31A
Fig. 31B
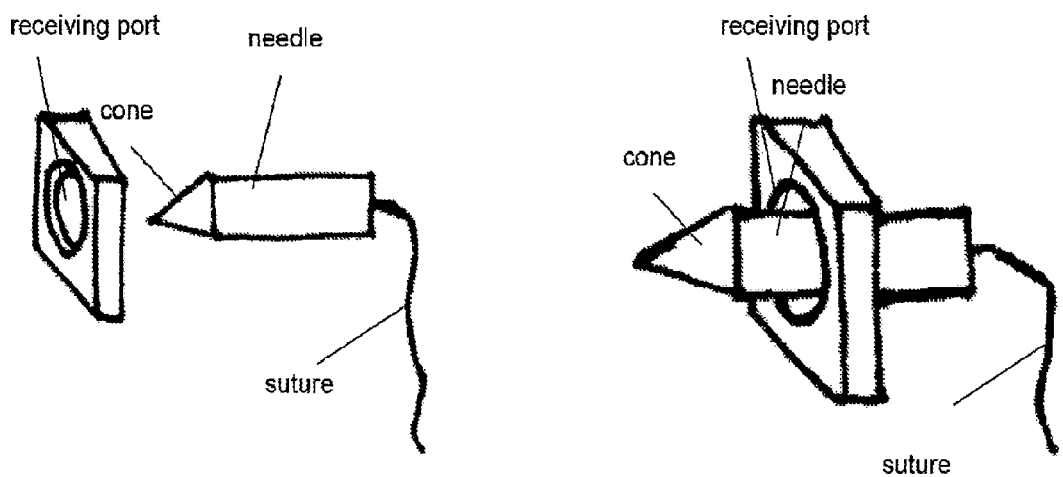
Fig. 31C
Fig. 31D

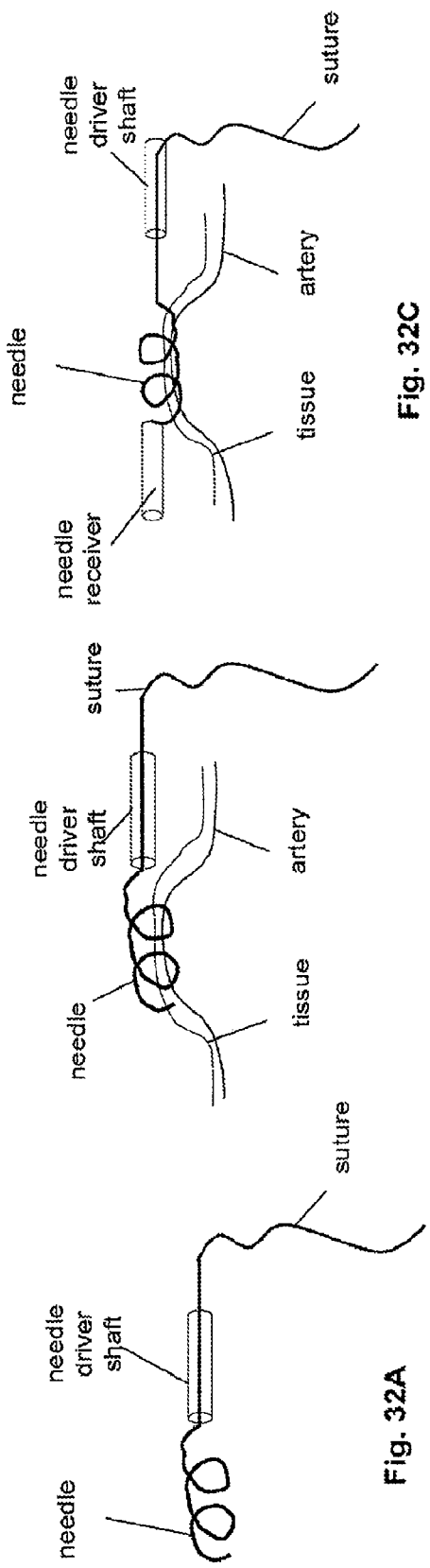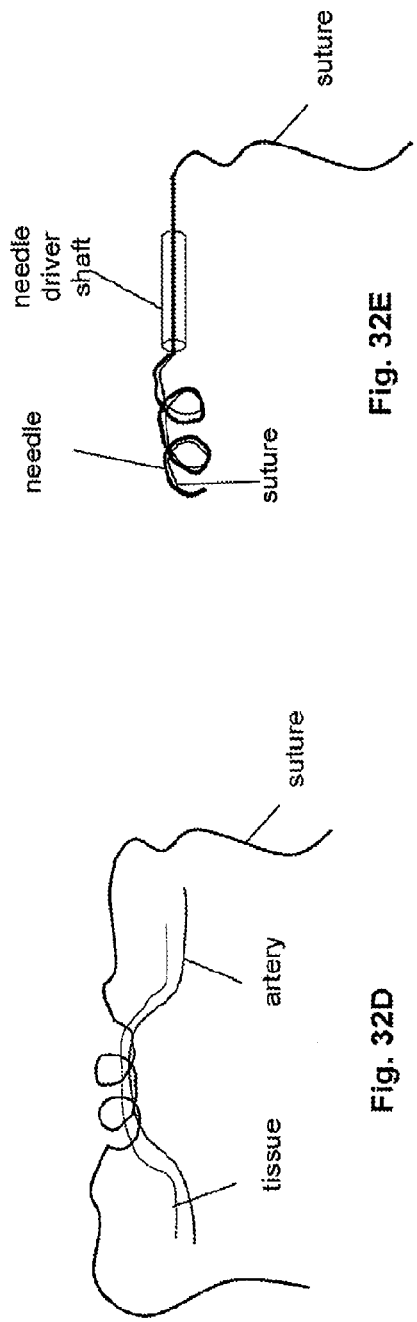
Fig. 32A Fig. 32B Fig. 32C Fig. 32D Fig. 32E

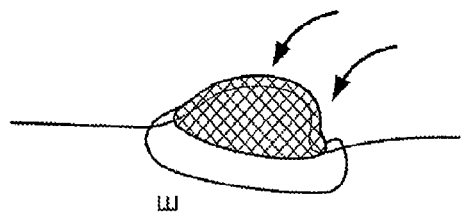
FIG. 35A PROLAPSED HEMORRHOID
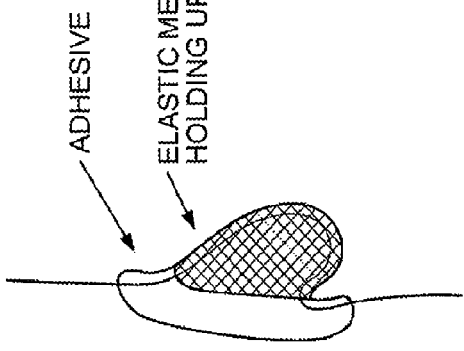
FIG. 35B ADHESIVE / ELASTIC MESH OR MEMBRANE HOLDING UP HEMORRHOID
FIG. 35C
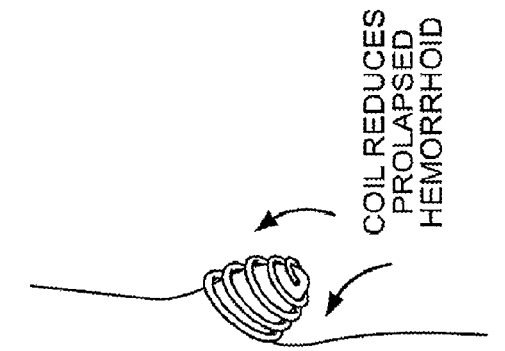
FIG. 36A SHAPE MEMORY ELASTIC COIL
FIG. 36B
FIG. 36C COIL REDUCES PROLAPSED HEMORRHOID
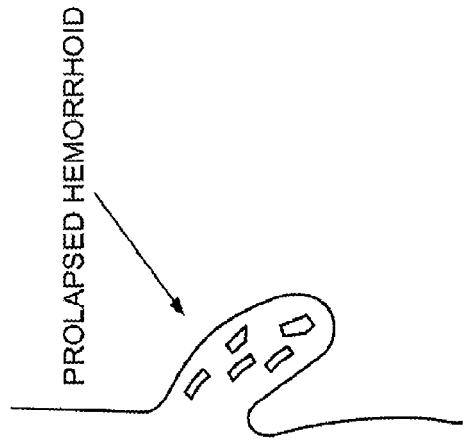

CLOSURE DEVICE AND METHOD

CROSS_REFERENCE TO RELATED APPLICATIONS

This application claims priority to U.S. Provisional Application Nos. 61/153,278, filed 17 Feb. 2009; 61/220,742, filed 26 Jun. 2009; and 61/266,981, filed 4 Dec. 2009, which are incorporated herein by reference in their entireties.

BACKGROUND OF THE INVENTION

1. Field of the Invention

The present invention relates to medical devices used for closure or ligation (e.g., mechanical ligation) of vessels, such as arteries or veins, such as vessels in the GI tract, for example veins in the esophagus or arteries in the GI tract, more narrowly the hemorrhoidal arteries, More particularly, the present invention relates to methods and apparatus to treat hemorrhoids without subjecting patients to pain, or with minimal pain.

2. Description of the Related Art

Hemorrhoids are a network of vascular cushions that exist as a normal part of human anatomy present in all healthy individuals. However, the term 'hemorrhoids' is generally used to refer to the disease process whereby a person develops symptoms when the hemorrhoids become inflamed, thrombosed, or prolapsed. When a person strains during defecation the pressure within the rectum increases and causes engorgement of the hemorrhoids. The mechanism of action is believed to be due to decreased venous return and continued arterial supply. Additionally aging causes laxity of connective tissues supporting the hemorrhoids and, hence, increases their ability to prolapse.

Hemorrhoids are simply enlarged vascular structures in the anal canal that produce discomfort, soiling of undergarments, intense itching, and in some patients, excruciating pain.

Hemorrhoids are one of the most common medical afflictions of older adults. The prevalence of hemorrhoids in the United States is approximately 13 million with a yearly incidence of 1.5 million. With a peak prevalence in the 45-65 age range, hemorrhoids particularly impact the quality of life for millions of Baby Boomers. However, only about a third of these patients seek medical treatment. This may be due to the fact that people are uncomfortable talking about this problem, that there is perception that there is no good treatment for this problem, or that there is a complicated referral pathway. The grading system used by physicians has 4 grades of increasing severity. Grade I are internal hemorrhoids that bleed. Grade II hemorrhoids are those that bleed and prolapse with straining but return by themselves. Grade III hemorrhoids bleed and prolapse with straining and require manual replacement. Grade IV hemorrhoids do not return to the anal canal and are chronically prolapsed.

Grade I hemorrhoids are treated conservatively with dietary changes (including increasing fiber and water intake) to soften the stool and medications to increase the lubrication of the stool. Grade II hemorrhoids that do not resolve with the above therapies are treated by a variety of methods, with rubber band ligation being the most common and effective. This method is fast and relatively pain-free, but has a recurrence rate of about 70% after 3 years and it usually requires several return visits to the physician. Grade III hemorrhoids are candidates for several different treatments as well, with an emphasis currently on stapled hemorrhoidopexy, doppler-guided hemorrhoidal artery ligation (DHAL), and hemorrhoidectomy. The efficacies of these therapies are approximately 80% for stapled hemorrhoidopexy and 70% for DHAL. DHAL is associated with significantly less pain that stapled hemorrhoidopexy or hemorrhoidectomy, but it is a relatively new technology and is currently not widely adopted. Grade IV hemorrhoids are typically treated by a surgical hemorrhoidectomy, which has an efficacy of 95% and almost no recurrence, but it causes a significant amount of post-operative pain and can risk complications such as permanent fecal incontinence. Patients miss an average of 11 days of work due to the severity and duration of pain.

Currently there is no treatment that is both highly effective and has a low rate of post-procedural pain and complications. Procedures with low invasiveness, such as rubber-band ligation, are used on mild hemorrhoids with few complications, but have poor long-term efficacy. More invasive procedures, such as hemorrhoidectomy and stapled hemorrhoidopexy, have good long-term efficacy, but are associated with significant pain and high complication rates. Thus, there is a need for a more effective way to treat Grade II, III, and IV hemorrhoids that is effective, but produces little pain and few complications, and has a low recurrence rate.

Methods of treatment using hemorrhoidal dearterialization (HD) work by ligating the hemorrhoidal (aka rectal) arteries, more specifically the superior hemorrhoidal arteries via hand-thrown sutures, performed through an anoscope that required significant dilation of the anal canal. HD causes the blood-engorged hemorrhoids to regain their normal structure within a few weeks. Numerous studies show that HD cures greater than 90% of grade II-IV hemorrhoids, with almost no post-operative pain in 95% of patients.

There is also great need for a treatment that can be performed outside the operating room (OR) by surgeons and non-surgeons alike. Meeting this need could decrease costs and increase the number of patients who could receive treatment. First, costs should decrease because current treatments, such as hemorrhoidectomy, can only be performed in the OR, which is tremendously expensive. Second, a new treatment performed by non-surgeons would simplify the referral pathway, which could increase the number of hemorrhoids treated. Currently, patients must first see a primary care physician and/or a gastroenterologist, who then refer to a surgeon who has the requisite skills to perform current procedures. The long cycle of care causes many patients to never receive treatment, as patients are lost between referrals. If gastroenterologists had a tool to effectively treat hemorrhoids, they could treat the patients they diagnose, preventing patients from being lost in a long referral chain. Fewer appointments would also decrease costs.

SUMMARY OF THE INVENTION

Methods, systems, and apparatus of ligation (e.g., mechanical ligation) of vessels, such as arteries or veins, such as vessels in the GI tract, for example veins in the esophagus or arteries in the GI tract, more narrowly the hemorrhoidal arteries are disclosed. The systems and methods can utilize hemorrhoidal dearterialization (HD) in which the arteries feeding the hemorrhoids are located and then sealed off. The systems and methods can utilize transanal open hemorrhoidopexy (TOH) in which the hemorrhoids are pexied (lifted and tacked up) to the more proximal anorectal canal, thereby preventing their prolapse. Tools are disclosed to make HD and TOH easier to perform, safer, require less anal dilation, able to be performed outside the OR, and can be performed without surgical training.

Apparatus and methods are disclosed for treating hemorrhoids with minimal or no pain to the patient during and/or after the procedure. The disclosed treatments can be performed outside an operation room (for example in a clinic or office setting), rapidly without the need to have multiple tool exchanges (approximately 10 minutes), easily with minimal training or prerequisite skills required for the operator (surgeons, gastroenterologists, primary care physicians, nurses, and/or the patient themselves) and efficaciously with minimal reoccurrence.

A device is disclosed comprising two or more distinct sections: a sensor component for vessel (e.g. artery) detection and location, and a ligation component to ligate the vessel. Some embodiments contain other components, for example, a fixation component to allow for easier ligation, a stopper to ensure the working end of the device is inserted to the proper depth, and a handle. Coupled with the device is a vessel (e.g. artery) detection processing unit, such as a Doppler processor.

Some embodiments contain a ligation electrode(s), a shaft and a proximal handle. Coupled with some embodiments is an ablation energy generator, such as radiofrequency, high intensity focused ultrasound (HIFU), laser, microwave or cryo.

The device can be inserted into the anus until either the touch sensor is in contact with the external anus, or when the stopper stops the device from being inserted further into the anal canal, to position the Doppler sensor and electrode above the dentate line. (Interventions performed above the dentate line are painless.) Next, the user/operator will turn the distal surface of the device to be in contact with the interior wall of the rectum (e.g. by articulating a steerable joint). The device is then rotated until the Doppler transducer picks up signals of arterial flow beneath the rectal mucosa that the transducer is in contact with. Next, the ligation mechanism is deployed to stop flow through the artery. In some embodiments the mucosa is fixed in place after detection of the appropriate artery and prior to deploying the ligation component. In some embodiments the ligation component is a mechanical closure.

In some embodiments the ligation component uses energy that is delivered through an electrode that is adjacent to the Doppler transducer to the hemorrhoidal artery to ligate or ablate the artery. For example, radiofrequency energy can be delivered to precisely increase the temperature of the hemorrhoidal artery to a temperature above 85 degrees Celsius. Fibrotic closure of the artery or plexus occurs when subjected to heat above 85 degrees Celsius. As neighboring tissue surrounding the hemorrhoidal artery is mucosal or sub-mucosal tissue, any potential collateral injury (if any) due to the energy source will be healed with minimal inflammatory response or clinical complications. Thermal or ablative energy is delivered until the Doppler transducer does not pick up any signal of arterial flow. At this point, the hemorrhoidal artery that is subjected to the thermal or ablative energy would be ligated, thereby stopping blood flow downstream from the ligated section to the prolapsed hemorrhoidal plexus. This consequently over time will reduce the engorged hemorrhoid plexus and treat the prolapsed hemorrhoids downstream of the ligated hemorrhoidal artery definitively. The procedure can then be repeated by rotating the device circumferentially 360 degrees until all hemorrhoidal arteries close to the surface of the interior rectal wall are ligated.

The user/operator can then perform a confirmation check by rotating the device for another 360 degrees to detect any arterial blood flow and look for any hemorrhoidal artery that might have been missed or not ligated previously. The procedure can be considered complete when the confirmation check detects no arterial blood flow to the downstream hemorrhoid prolapsed plexus.

Other embodiments of the invention include the use of balloon, expandable basket, mesh or other expandable member in place of a solid probe at the distal end of the device. Instead of the use of radiofrequency, other energy sources such as HIFU can be used in place of RF electrodes. In another embodiment the hemorrhoidal artery ligation can be performed with the use of steam injected directly into the artery to reduce collateral injury.

Other features include: a control circuit which automatically determines the optimal power and time requirements, based on feedback from the artery and arterial flow sensor; and a radio frequency (RF) electrode-array controlled by an array of Doppler ultrasound elements, such that only electrode elements overlying an artery are activated to ablate underlying tissue.

Other artery detection sensors or methods are also described. First, the sensor can be laser Doppler flowmetry. Second, the patient can receive intravenous indocyanine green dye, followed by detection of the arteries by near-infrared video angiography. Third, the arteries can be detected by measuring absorption of electromagnetic energy from the mucosa. Fourth, the sensor can use multiple wavelength bands of electromagnetic energy to differentiate arteries from veins, by comparing absorption at these wavelengths. Including Doppler ultrasound sensors, a combination of any of the above sensors can also be used to detect submucosal arterial segments with internal blood flow, in conjunction with or incorporated into inventions described in this document.

The devices and methods herein can reduce or eliminate the pain of hemorrhoid treatment. Methods and apparatus in this application also describe a rapid, convenient and simple way to perform minimally invasive, painless (or minimally painful) treatment of hemorrhoids as both the hemorrhoidal artery detector, such as the Doppler transducer, and the artery ligation tool, such as the RF electrode, can be in a single device with no working channels required. No tool exchanges, such as passing suture and needles, laser coagulation device, or other energy ablation tools, through the working channel of an anoscope or a dilator with Doppler transducer sensors, is required to perform the treatment. Inventions described in this application also represent apparatus and methods to access the anal canal and treat hemorrhoids that do not require patient's anus to be dilated. This is a key advantage as excessive or prolonged anal dilation has been known to be a potential cause of fecal incontinence, a possible complication that could result using other hemorrhoid treatment tools or options as described in prior art. Other advantages also include safety features to ensure energy delivery or ablation can only be performed when the electrode is positioned above the dentate line (for management of pain); and obviating the need for users/operators to depend on good direct visualization (often challenging due to obstructing tissue and poor illumination) to perform ligation of superior hemorrhoidal artery.

Various embodiments and methods by which HD and/or TOH is accomplished via mechanical compression of the hemorrhoidal artery are also described. Platforms on which the devices perform HD and/or TOH can include a hand-held wand that can be inserted into the anus; and a device on the end of an endoscope.

SUMMARY OF THE DRAWINGS

FIGS. 2A through 2C illustrate variations of the device.

FIGS. 6A through 6C illustrate variations of the clip.

FIGS. 7A and 7B illustrate an embodiment of a clip in open and closed configurations, respectively.

FIGS. 8A and 8B illustrate another variation of a clip having different length clip arms.

FIGS. 8C and 8D are side views of another variation of a clip in which the clip arms have the same length.

FIGS. 10A and 10A' are side views of variations of a clip in an undeformed configuration.

FIGS. 10B through 10E are side views of variations of the clip of FIG. 10A in deformed configurations.

FIG. 10F illustrates another variation of the clip in an undeformed configuration.

FIGS. 10G through 10J illustrate variations of the clip of FIG. 10F in deformed configurations.

FIG. 13A is a side view of the hemorrhoid treatment device with the distal expandable basket half deployed.

FIG. 14A illustrates a variation of a balloon catheter with ultrasound crystals mounted to the exterior of the balloon.

FIG. 14B illustrates a variation of cross-section A-A of FIG. 14A.

FIG. 14C illustrates a variation of a balloon catheter with ultrasound crystals mounted on the internal shaft of the balloon.

FIG. 14D illustrates a variation of cross-section B-B of FIG. 14C.

FIGS. 16C and 16D are oblique and top view, respectively, of the device with a Doppler-electrode-array and ultrasound waves emanating from the array.

FIGS. 16A' and 16B' are side views of another embodiment of a clip in open and closed configurations.

FIGS. 24A' and 24B' illustrate a variation of a method for treating hemorrhoids by pexying with a radially expandable stent.

FIGS. 25A' and 25B' illustrate a variation of a method using hooks to create a tissue mound before applying a clip.

There is no FIG. 27.

Figure 28:
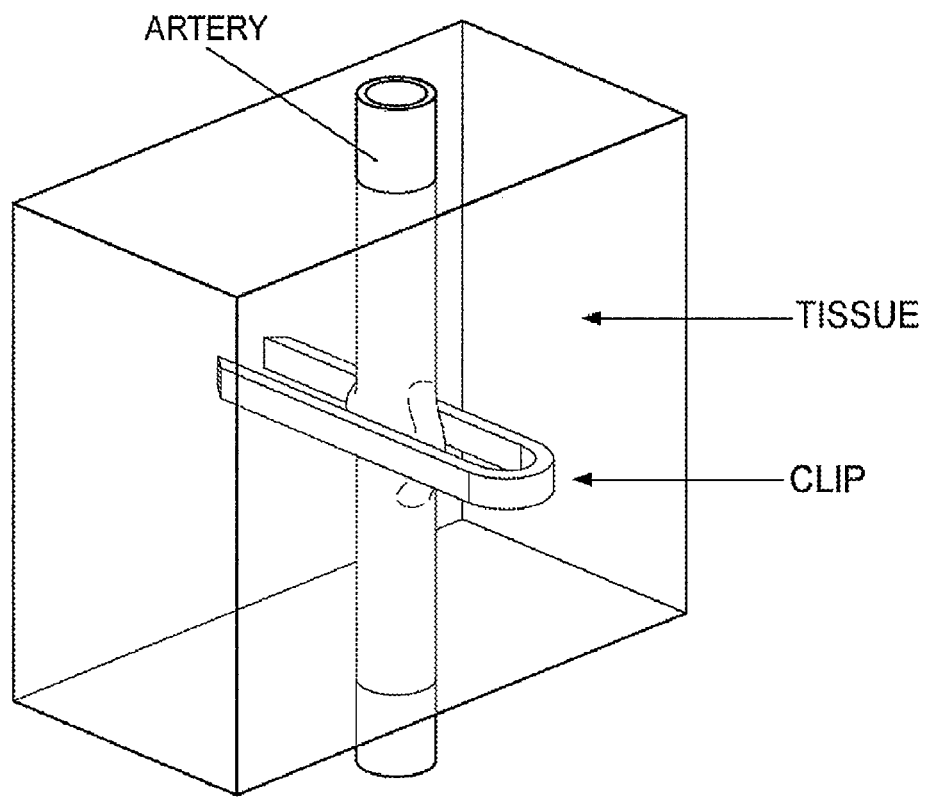

FIG. 28 illustrates a variation of using a clip in a section of tissue.

Figure 29A:
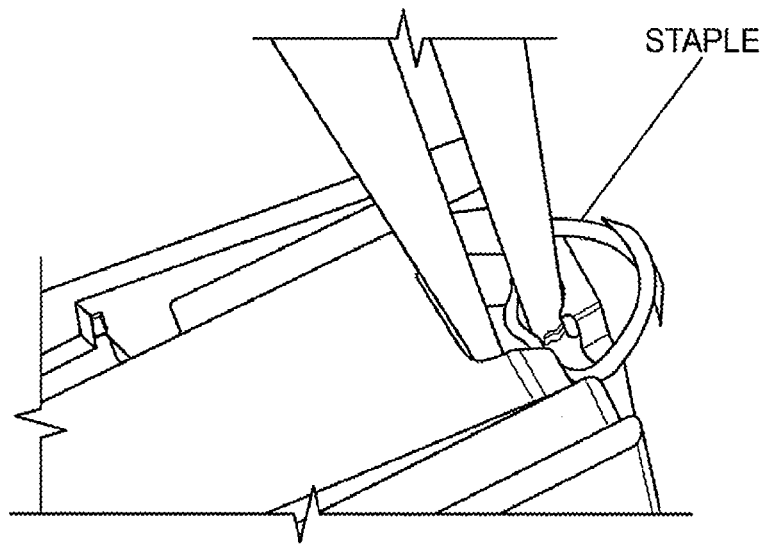
Figure 29B:
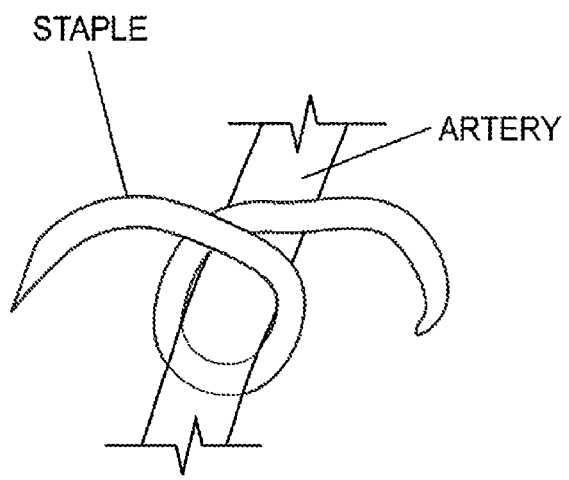

FIGS. 29A and 29B illustrate a variation of a method for using a staple.

FIGS. 30A through 30D illustrate a variation of ligating a hemorrhoidal artery.

FIGS. 31A through 31H illustrate a variation of ligating a hemorrhoidal artery.

FIGS. 32A through 32D illustrate a variation of ligating a hemorrhoidal artery.

FIG. 32E illustrates a variation of the device of FIGS. 32A through 32D.

Figure 33A:
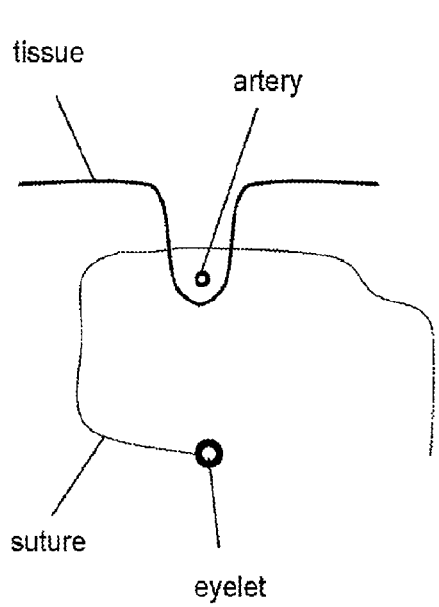
Figure 33B:
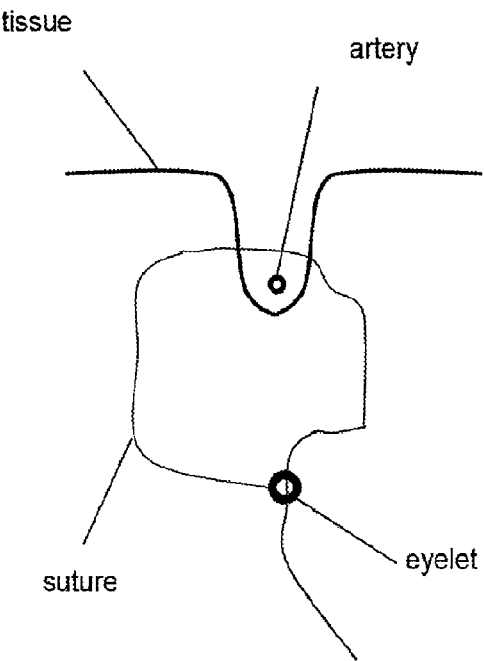

FIGS. 33A through 33B illustrate a variation of ligating a hemorrhoidal artery.

FIGS. 34A through 34E illustrate a variation of ligating a hemorrhoidal artery.

FIGS. 35A through 35C illustrate a method of pexying a prolapsed hemorrhoid.

FIGS. 36A through 36C illustrate a method of pexying a prolapsed hemorrhoid.

DETAILED DESCRIPTION

This application discloses devices (i.e., apparatuses) and methods that provide a way to treat patients suffering from hemorrhoids. The apparatuses and methods can treat hemorrhoids with minimal or no pain to the patient during and/or after the procedure. The treatment can be performed outside an operation room (for example in a clinic or office setting), rapidly without the need to have multiple tool exchanges, in approximately 10 minutes, easily with minimal training or prerequisite skills required for the operator (e.g., surgeon, gastroenterologist, primary care physician, nurse, and/or the patient themselves), efficaciously with minimal reoccurrence, or combinations thereof.

Figure 1B:
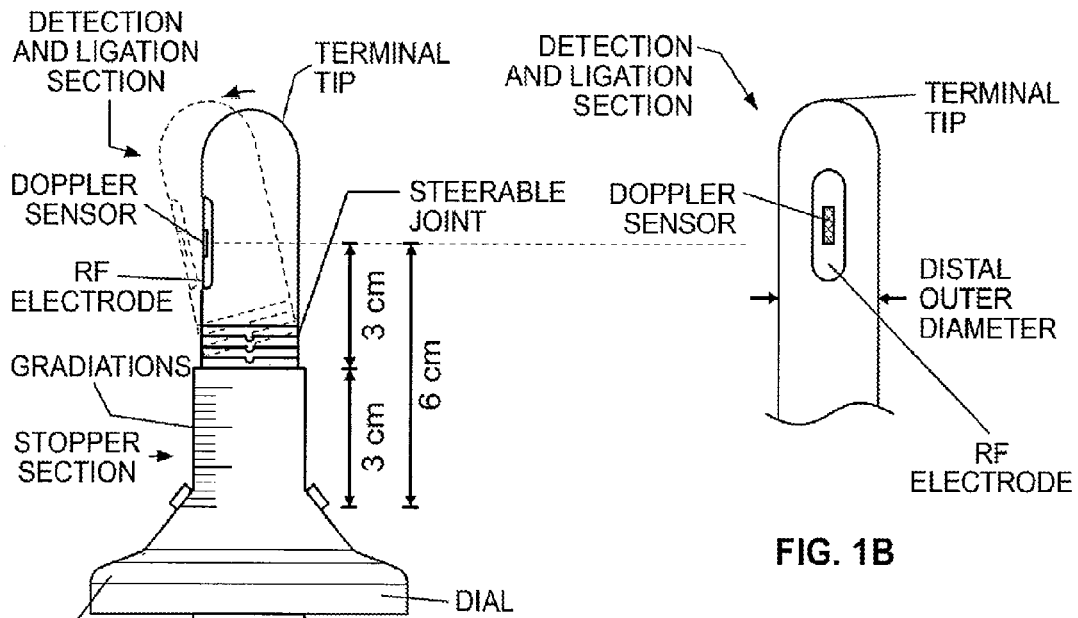
FIG. 1B is an orthogonal view of the distal end of the device shown in FIG. 1A.
Figure 1A:
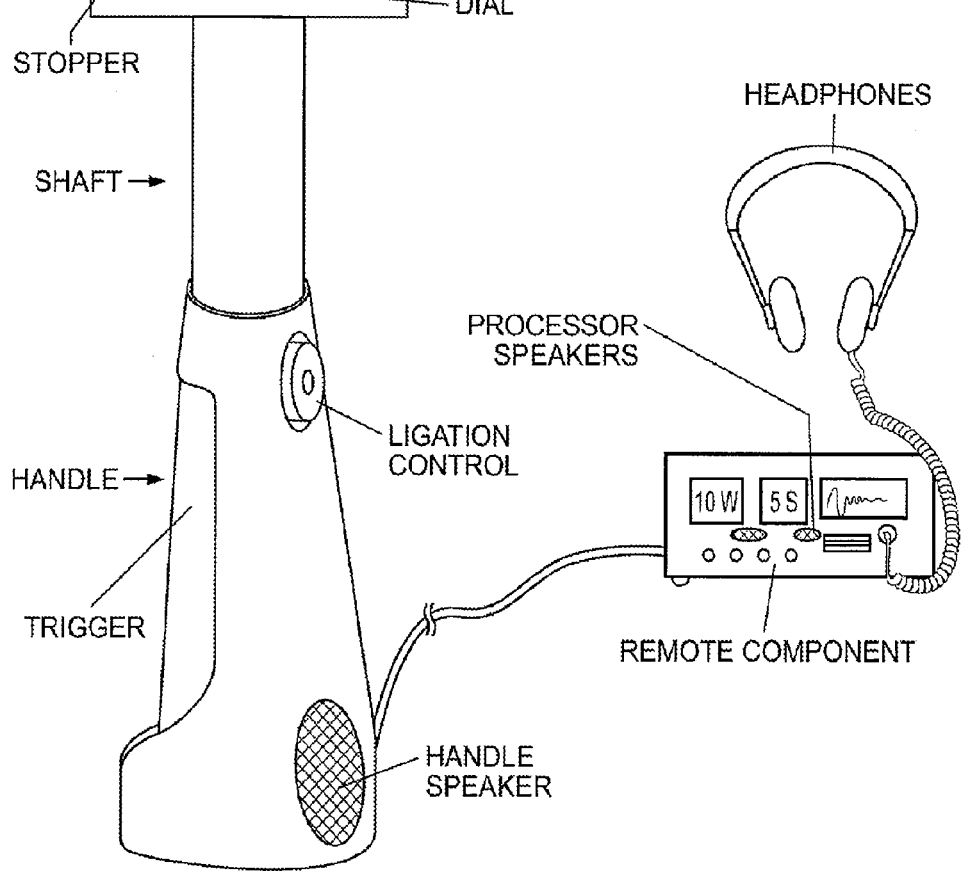
FIG. 1A is a side view of one embodiment of the painless hemorrhoid treatment device coupled to a radiofrequency energy generator and a Doppler processor.

As seen in FIG. 1A, the device can have about four distinct sections: a distal artery detection and ligation section, an insertion stopper section, a shaft, and a proximal handle. Coupled with the device is an ablation energy generator, such as radiofrequency, high intensity focused ultrasound (HIFU), laser, microwave energy generation or cryo generation component, and the artery detection processing unit, such as a Doppler processor.

The distal artery detection and ligation section ("distal section") can have a traumatic or atraumatic terminal tip. For example, the terminal tip can be soft, such as by being covered with a soft elastomer, and comfortable for use during insertion into the anus.

FIGS. 1A and 1B illustrate that the distal tip can have an ligation element, such as a monopolar or bipolar RF ablation electrode, mounted on the exterior surface of the distal section. A Doppler sensor/transducer can be positioned in the middle of the electrode. The RF electrode can surround the Doppler transducer, for example to maximize ablation of the area sensed by the Doppler transducer (e.g., to ablate to fully stop the blood flow or otherwise ligate the hemorrhoidal artery detected by the Doppler transducer). The Doppler transducer can be positioned in the middle of the ablation electrode, for example to deliver energy to ligate the artery detected by the Doppler signal.

The distal section can have a distal outer diameter that is small enough to not require a patient's anal canal to be dilated before said invention can be inserted. For example, the distal outer diameter can be about equal to or smaller than the diameter of an average adult human finger. The distal outer diameter can be smaller than about 2 cm, more narrowly smaller than about 1.5 cm, yet more narrowly smaller than about 1 cm.

The section connecting the distal artery and ligation section to the mid-shaft section can be made of one or more steerable joints or links, for example covered by a flexible case, housing or boot. The steerable joints or links can enable the distal detection and ligation section to be articulated at an angle to access and be in contact with the rectal wall. The articulating joint can be made from pull wires, pinned links, laser cut extrusions, double durometer extrusions, or combinations thereof.

Proximal to the steerable joints, the device can have an insertion stopper. The insertion stopper can have at least about two different outer diameters along the longitudinal profile, the first distal diameter can be approximately the diameter of the artery detection and ligation section, and the second outer diameter, proximal to the first diameter, is of an outer diameter at least two times that of said first outer diameter. The insertion stopper can prevent the hemorrhoid treatment device from being inserted too deep into the anal canal (e.g., greater than about 8 cm from anal verge) and potentially damaging the middle or superior rectum or the sigmoid colon. The insertion stopper can have depth measurement gradations or markings longitudinally along the insertion stopper, for example, to inform the user/operator length of the device that is inserted into the anal canal. The visible gradations can be checked during insertion of the device into the anus. The gradations can be used to increase the likelihood that the ablation component, such as the RF electrode, has been inserted into the colon above the dentate line before performing a substantially painless (e.g., performed superior to the dentate line) ligation, for example inserted about 2-3 cm.

FIG. 1A illustrates that for example, when the device is fully inserted through the hemorrhoid patient's anus, the Doppler transducer and ablative electrode can be positioned approximately 6 cm (e.g., plus-minus 1 cm) above the anal verge, or approximately 1 cm to 2 cm above the dentate line. This position represents a pain-free position for the device to locate superior hemorrhoidal arteries and to ligate the hemorrhoidal arteries by the ablative energy source, such as radiofrequency, via the electrode around the Doppler transducer.

The device can have multiple touch sensors positioned circumferentially around the insertion stopper at the transition between first distal smaller outer diameter and the second proximal larger outer diameter. Said touch sensors can be a safety mechanism, for example to ensure ablative energy can only be activated when the electrode is placed above the dentate line. When the touch sensors are in contact with the external anoderm, the device is fully inserted with the electrode and Doppler transducer at least 5 cm from the anal verge, thereby being at least 2 cm above the dentate line. (The dentate line is about 2.5-3 cm above the anal verge.) Delivering of ablative energy or heat above the dentate line is important as therapy on the interior wall of the rectum is painless if it is above the dentate line.

The stopper can have a dial, for example at the proximal end of the stopper. Rotating the dial can control rotating of the device, for example to rotate the electrode and Doppler sensor about 360° or more with respect to the remainder of the device proximal to the stopper.

The third section of the device is a cylindrical shaft connecting the insertion stopper section and the proximal handle section. Said shaft can be rigid or flexible. If said shaft is flexible, it will be at a durometer that allows proper force transmission along the shaft such that the device can be easily inserted into the anus and apply decent contact pressure on the rectal wall for the Doppler transducer to effectively locate and detect arterial flow and for the electrode to effectively delivery heat or other ablative energy (such as cryo) to ligate the hemorrhoidal artery. Between the shaft and the insertion stopper is also a rotation dial that tracks the rotation of the device. Hence, if the device is rotated over, for example 30 deg, the dial located on the proximal side of the insertion stopper (distal to the shaft) will indicate a colored arc showing that the device has been rotated for 30 degrees as a way to help user/operator keep track. The purpose of said rotation dial is to ensure that the user/operator has rotated the device a full 360 degrees to thoroughly locate all hemorrhoidal arteries circumferentially to ligate.

The device can have a handle section ("handle") proximal to the shaft section. The handle section can be the most proximal section of the device. The handle can comprise of a squeeze trigger that steers the steerable section of the distal tip, a ligation control such as an ablation start/stop button to manually activate or override the energy source used for ablation or ligation, an audio handle speaker to playback Doppler audio signals when an artery is located. The audio handle speakers can be built in to the handle and broadcast sound corresponding to the detected vascular (e.g., arterial) flow. The trigger can have a locking mechanism to fix the angle of the steerable section of the distal tip at an angle.

The device can be coupled from the handle to an energy generator, such as a radio frequency, HIFU, microwave, laser or cryo generator. The device can be coupled to a Doppler ultrasound signal processor, or a processor of an alternative sensor that can be used in place of Doppler to locate and detect hemorrhoidal arteries. More of such alternative sensors that can be used in place or in conjunction with Doppler are disclosed in the later part of this application. The Doppler or alternative processor can deliver output to visual (e.g., video monitor) and/or audible (e.g., processor speakers and/or headphones) components. The processor and/or generator can be within the housing of the handle and/or attached to a remote component.

Figure 2A:
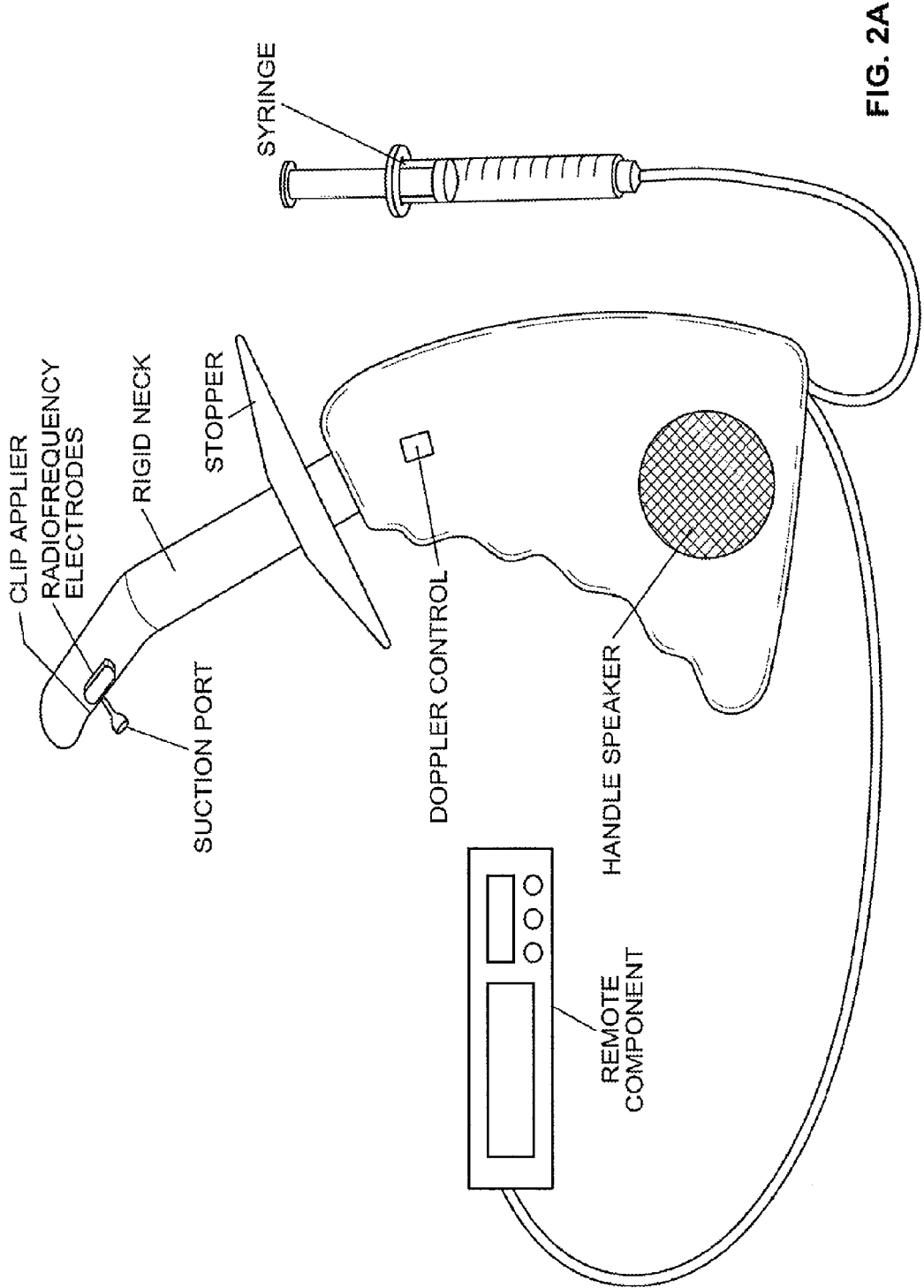

FIG. 2A illustrates that the device can be a hand-held, stand alone device. The device can have a Doppler ultrasound sensor, suction, an energy-based ligation component such as a radiofrequency (RF) energy applier such as one or more RF electrodes, and/or a mechanical ligation component such as a clip applier. Initially, the physician can place the device into the patient's anus until the stopper or device cuff comes in contact with the external anus, for example to position the sensing and ligating components of the device above the dentate line. Once the device is positioned at the target site, the physician can turn on the Doppler sensor allowing the physician to locate the hemorrhoidal artery (of which there are approximately six). The distal tip can have a suction port in fluid communication with a section source. The suction source can be located away from the distal tip. For example the suction source can be a syringe coupled to the handle (as shown) or central suction (delivered from a wall port in a health care facility's room). The suction port can be extended from and retracted into the distal section of the device.

When the probe has located the artery, the physician can turn on the suction source (e.g., press a control button or draw on the syringe). The suction delivered by the suction port can fix to and/or pull the rectal tissue containing the hemorrhoidal artery of interest into the distal section of the device. The physician can then activate the clip applier, thereby sealing or collapsing the hemorrhoidal artery and/or turn on the radiofrequency energy from the RF electrodes, sealing or collapsing the hemorrhoidal artery.

The Doppler sensor, which can be continuously on during a surgical procedure, can determine if the artery has been sealed off when it no longer detects blood flow through the artery. If the radiofrequency energy is used, the radiofrequency energy can be automatically turned off (or the physician can determine when to turn it off) when the Doppler sensor no longer detects blood flow through the artery. This procedure will be repeated until all six of the hemorrhoidal arteries are collapsed. In place of a clip applier, this same device can also use any of the other methods of mechanical ligation described below, or other mechanical ligation mechanisms. The handle can have a Doppler control, such as a switch to turn the Doppler sensor on and off.

The distal section can be non-articulating and have a rigid neck.

FIG. 2B shows a variation of the device that can use a rubber band, or other mechanical mechanism to pinch closed the hemorrhoidal artery. The device can use Doppler ultrasound to locate the hemorrhoidal artery and suction to isolate the tissue of interest in the distal end of the device. The device can have a mechanical mechanism, such as a rubber band applicator, that can seal off the hemorrhoidal artery. Additionally, in this variation, the handle of the device can have a trigger that can have a lever mechanism by which the mechanical seal can be activated. The mechanical sealing mechanism could be performed in numerous ways, including via rubber bands, staples or clips.

The remote component and/or suction device (e.g., syringe, as shown) can have a clip. The remote component and/or suction device can be removably attached to the handle.

FIG. 2C illustrates that the distal section can have a distal lip proximal of the terminal tip. The distal lip can be proximal of the sensing component, such as the Doppler sensor, and ligation component, such as the RF electrode. The distal lip can be distal of the stopper. The distal lip configuration can bend sharply toward the longitudinal axis of the neck proximal to the distal lip. The Doppler sensor and RF electrode can be positioned laterally away from the longitudinal axis of the neck of the device. During use, the distal lip can be inserted past the prolapsed hemorrhoid and then pulled back partially toward the anus. The distal lip can be used to pull the prolapsed hemorrhoid down (i.e., inferiorly) to position the hemorrhoid adjacent to the Doppler sensor and RF electrode and inferior to the terminal tip.

Figure 3B:
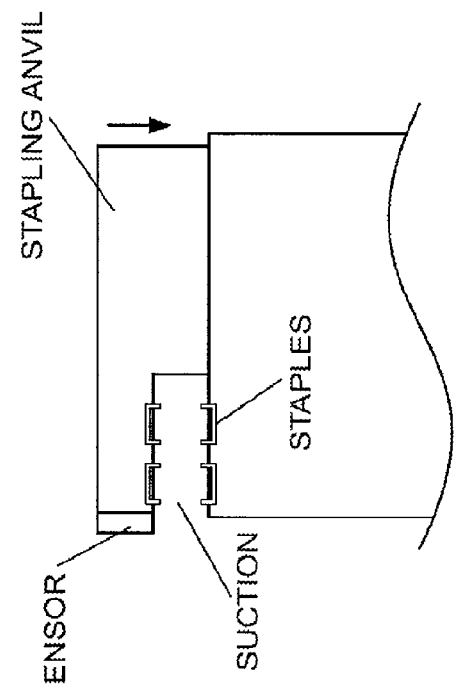
FIGS. 3A, 3B and 3C illustrate variations of the distal end of the device having various ligating components.
Figure 3C:
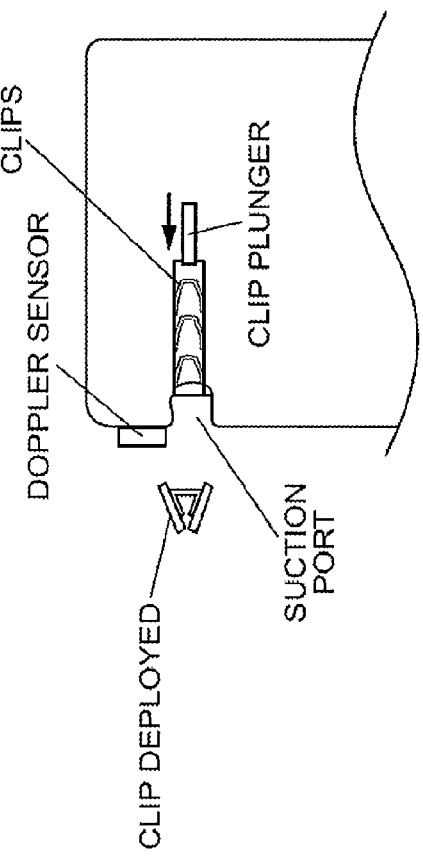
Figure 3A:
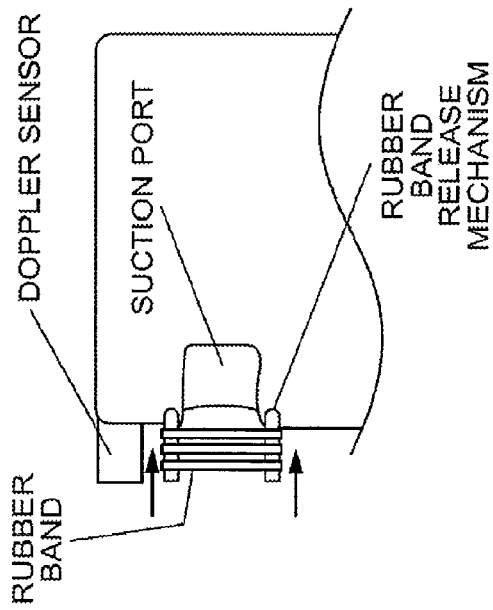

FIG. 3A illustrates the distal end of the mechanical sealing device using rubber bands to seal the hemorrhoidal artery. As shown, a cartridge of rubber bands can be circumferentially located around the distal window. In this embodiment, the tissue can be pulled into the distal window of the device via suction and then the physician can deploy the rubber band by pulling on the lever, shown in FIG. 2A. By pulling on the lever, the mechanism holding the rubber bands in place can retract, thereby pushing the most distal rubber band and releasing said rubber band around the base of the tissue. The pinching effect on the tissue fold can mechanically occlude the hemorrhoidal arteries.

FIG. 3B shows the distal end of the mechanical sealing device using staples to seal the hemorrhoidal artery. In this variation, two rows of staples will be located inside the mouth of the anvil at the distal end of the device. Once the artery has been located via Doppler and suction applied to pull tissue into the device, the physician will pull the lever at the proximal end of the device (as shown in FIG. 2A). This action will force the anvil to close and drive a row of staples into the tissue, thereby sealing the artery.

FIG. 3C shows another variation of the mechanical sealing invention by which clips are used to collapse the artery. In this embodiment, the artery is again located via Doppler, and suction is applied to pull tissue into the distal end of the device. The physician will then activate the lever located at the proximal end of the device to push a clip out of the device. Upon deploying said clip off the device onto the tissue fold, the clip will collapse into a closed configuration around the isolated tissue, thereby sealing the artery. (The clip applicator is shown in-plane for illustrative purposes, but can be out-of-plane compared to the figure as shown.)

Figure 4A:
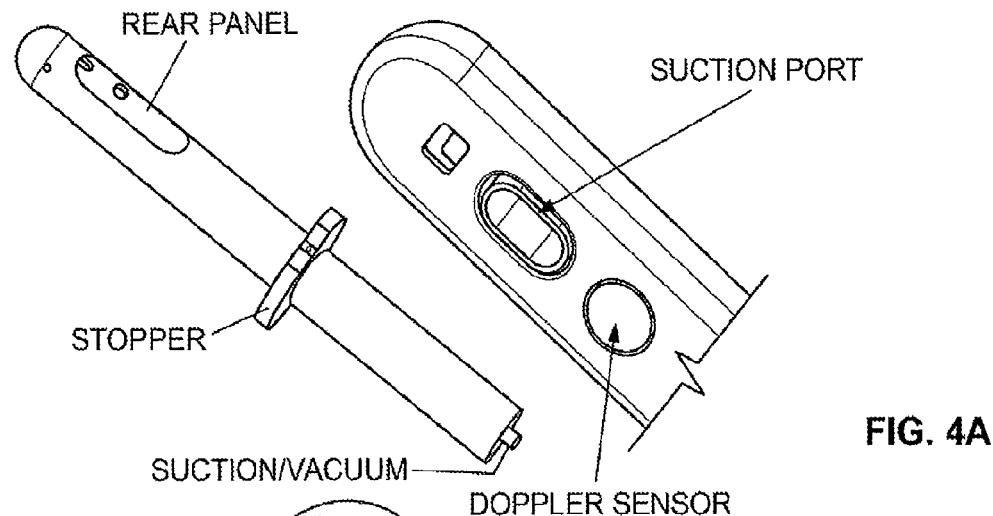
FIGS. 4A through 4C illustrate a variation of the distal end of the device during use.

FIG. 4A illustrates a device that has a suction port or aperture that can be flush with the bottom of the housing during the initial stage of suction. The suction port can have a suction port cover.

Figure 4B:
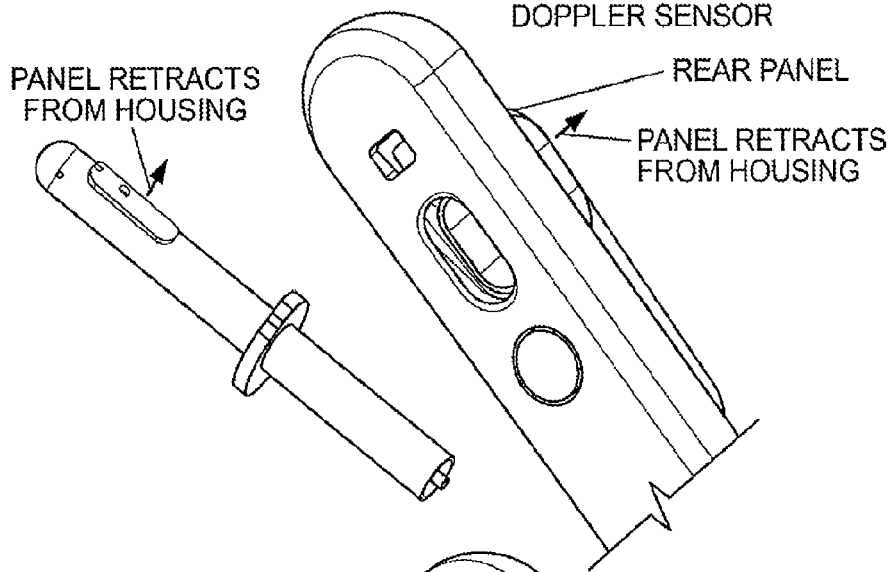

FIG. 4B illustrates that after the tissue is sucked into the suction port, the suction port cover can be retracted into the housing of the distal section as a rear panel attached to the suction port cover is elevated away from the opposite side of the housing from the suction port. The tissue that has been sucked into the suction port can be drawn into the housing.

Figure 4C:
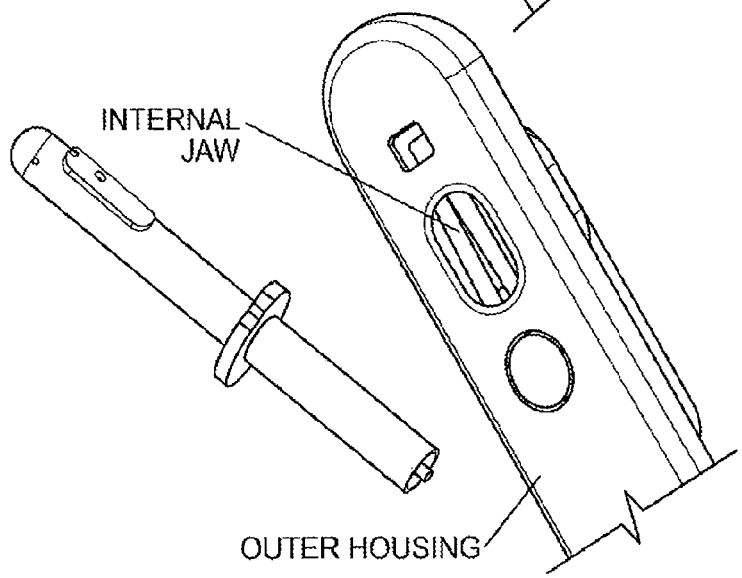

FIG. 4C illustrates that the distal end of the device can have a clamping mechanism located within the housing. The clamping mechanism can have opposed internal jaws that can clamp a clip onto tissue that has been sucked into the housing. When the suction port cover retracts into the housing, the tissue mound drawn into the housing by the suction port cover can be positioned adjacent to, and between, the internal jaws.

Figure 5A:
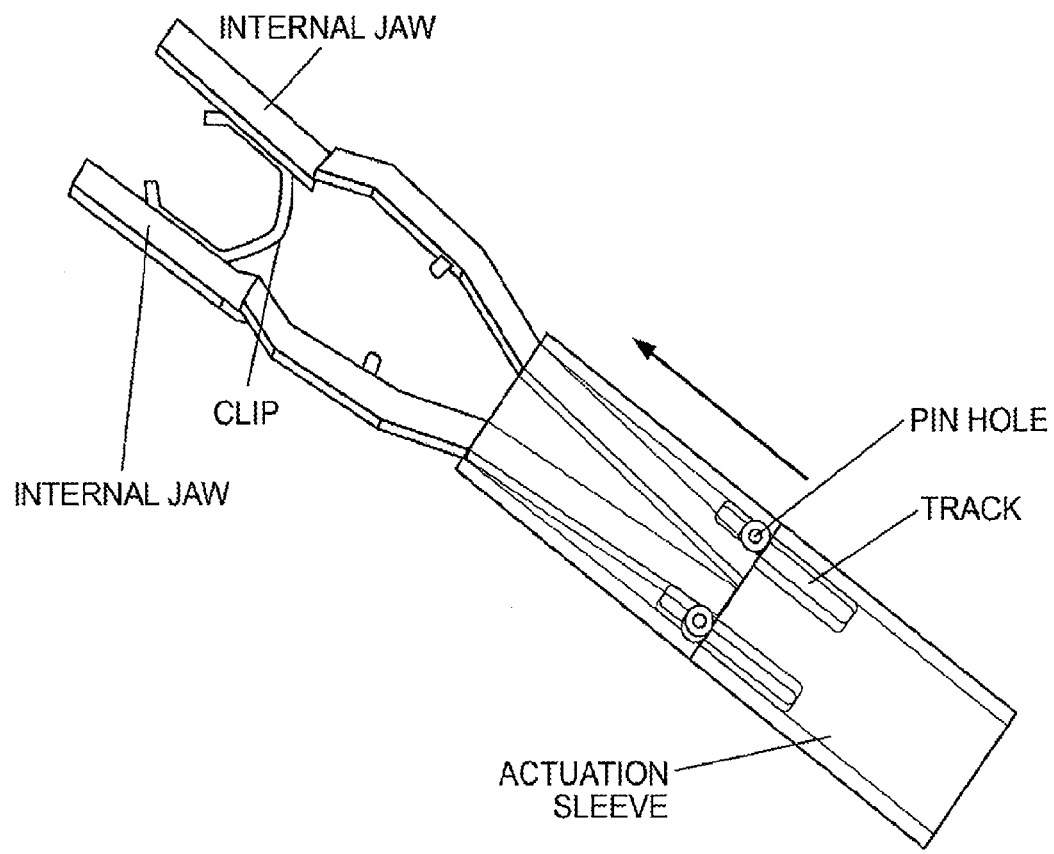
FIG. 5A illustrates a variation of a clip deployment mechanism that can be located inside of the housing of the device.

FIG. 5A illustrates that the jaws, which lie just inside the device housing, close on the tissue mound, thereby placing a clip across the tissue mound. The proximal ends of the internal jaws can be slidably attached by pins inserted through pin holes in the jaws to tracks in an actuation sleeve. The tracks can control and limit the jaw closure and opening by interference fitting against the pins. The actuation sleeve can encompass the length of the internal jaws positioned within the actuation sleeve. The width of the actuation sleeve can be less than the width between the opposed internal jaws when the jaws are in a relaxed configuration. The internal jaws can form a natural spring biased to be in an open configuration, and/or the internal jaws can have a spring attached between the jaws to bias the jaws outward from each other. As the actuation sleeve is slid distally with respect to the jaws, the jaws compress toward each other, compressing a clip positioned between the jaws and clamping any tissue located between the jaws. The jaws can be configured to close the clip tip before closing the clip base.

Figure 5B:
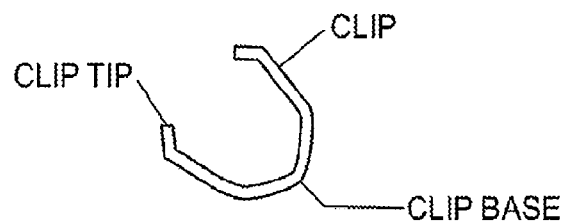
FIG. 5B illustrates a variation of the clip.

FIG. 5B illustrates a variation of the clip. The clip can have a clip tip and a clip base. When compressed, the clip tip can be closed before the clip base, for example to prevent tissue within the clip from being pushed out of the clip during clamping and clip compression. The clip can be plastically deformed when closed or the clip can be elastic and held open until deployed.

FIG. 6A illustrates that the clip tips at the terminal ends of the clip arms (i.e., clip legs) can be traumatic. For example, the clip tips can be barbed. The barbs pierce through the mucosa to the submucosa, thereby fixing the clip to the tissue. The barbs are offset (different clip arm lengths), so that when the clip is closed (goes from U-shaped to I-shaped), the barbs can flatten out better with increased interaction area. Additionally, the medial surfaces of the clips should be flat (rather than rounded), which can prevent scissoring of the clip. A cross-section of an artery shows a placement of the vessel within the clip during use.

FIG. 6B illustrates that the clip base can be V-shaped, which can aid in the clip being easier to close completely. The clip tips can be atraumatic. The clip tips can be configured to reduce puncture of tissue by the tips. The clip tips can be configured as spheres with larger cross-section diameters than the clip arms.

The lengths of the opposed clip arms can be different (as shown) or the same.

FIG. 6C illustrates that the cross section of the clip can be square. The clip can be configured to reduce the motion of the arms of the clip to scissor or move out of plane with the remainder of the clip.

FIG. 7A illustrates a naturally curled clip help in an open C-shaped configuration and inserted into the tissue around the artery. FIG. 7B illustrates that the clip can be released and relax into a closed configuration, compressing and ligating the artery.

FIGS. 8A and 8B illustrate that the clip tips can be directed inward and out of plane with the clip legs. The clip arms can be different lengths. The clip tips can point in opposite directions when out of plane.

FIGS. 8C and 8D illustrate that the clip arms can be the same length. The clip tips can abut each other in a staple-like fashion when closed and press downward. The clip tips can be out of plane and not abut each other when closed.

FIGS. 10A and 10A' illustrate variations of the clip in an undeformed configuration. The clip arms can be symmetric (e.g., have the same length) or asymmetric (e.g., have different lengths). FIGS. 10B through 10E illustrate variations of the clip of FIG. 10A in deformed configurations. The clips can be symmetrically barbed. The interaction area and forces can be high and the clips can be configured to scissor.

FIG. 10F illustrates a variation of the clip in an undeformed configuration. The legs of the clip can be asymmetric or offset (e.g., have different lengths). FIGS. 10G through 10J illustrate variations of the clip of FIG. 10F in deformed configurations. The clips can be offset barbed. The interaction area can be high. The clips can have a flattening interaction area. The clips can be configured to reduce or prevent scissoring.

Figure 12:
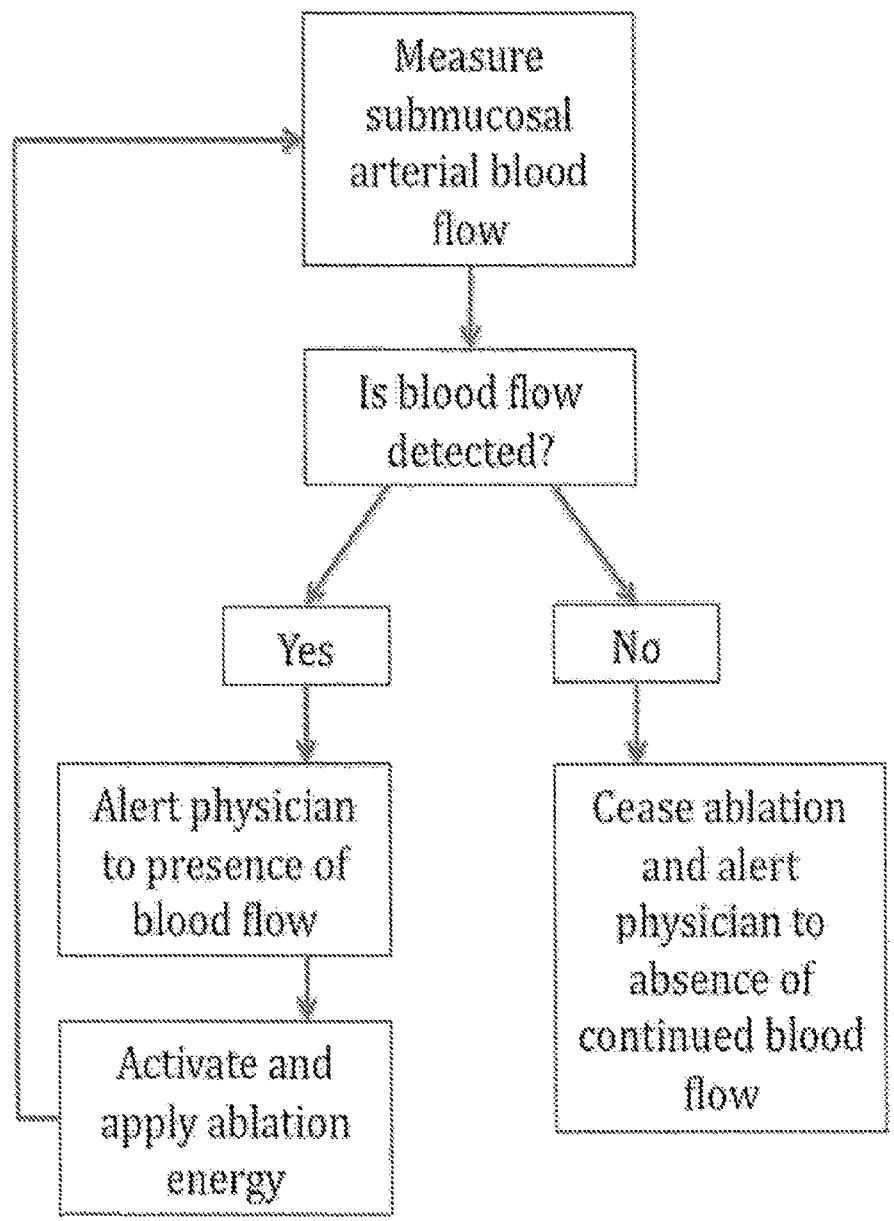
FIG. 12 is a schematic diagram illustrating automatic activation of the energy source based on signals picked up by the Doppler transducer to enable rapid and precise ligation of hemorrhoidal arteries.
Figure 12A:
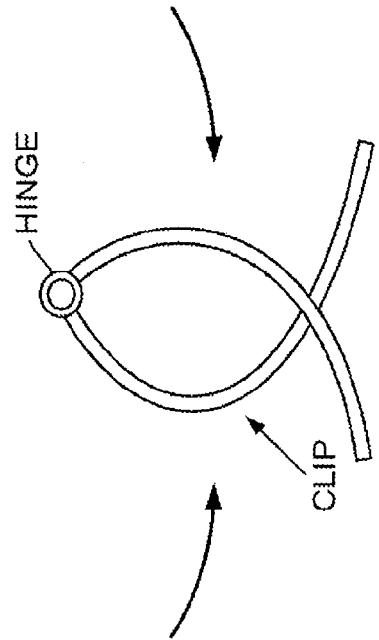
FIGS. 12A' and 12B' illustrate a variation of a clip that includes clip arms that are rotatable attached at a hinge.
Figure 12B:
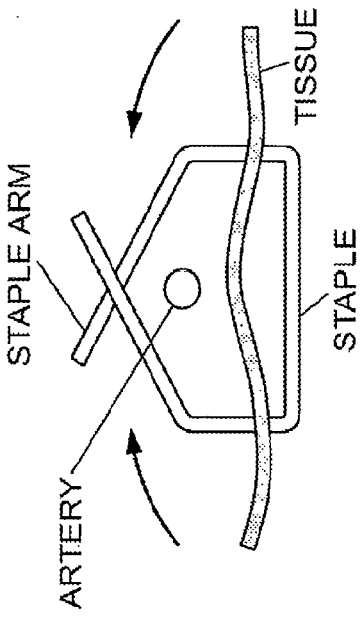

FIGS. 12A' and 12B' illustrate that the clip arms can be rotatably attached at a hinge.

Figure 13A:
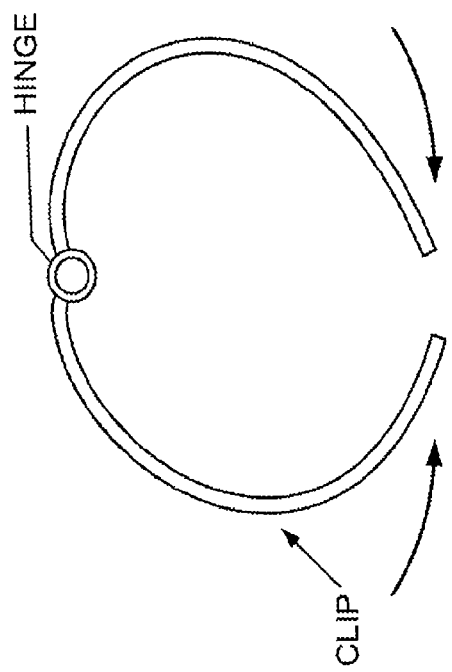
FIGS. 13A' and 13B' illustrate an embodiment of a staple that can be inserted around an artery.

FIGS. 13A' and 13B' illustrate that a staple can be inserted around the artery. The head of the staple can remain outside of the surface of the mucosal tissue. The staple arms can be bent around the artery, compressing and ligating the artery.

Figure 14:
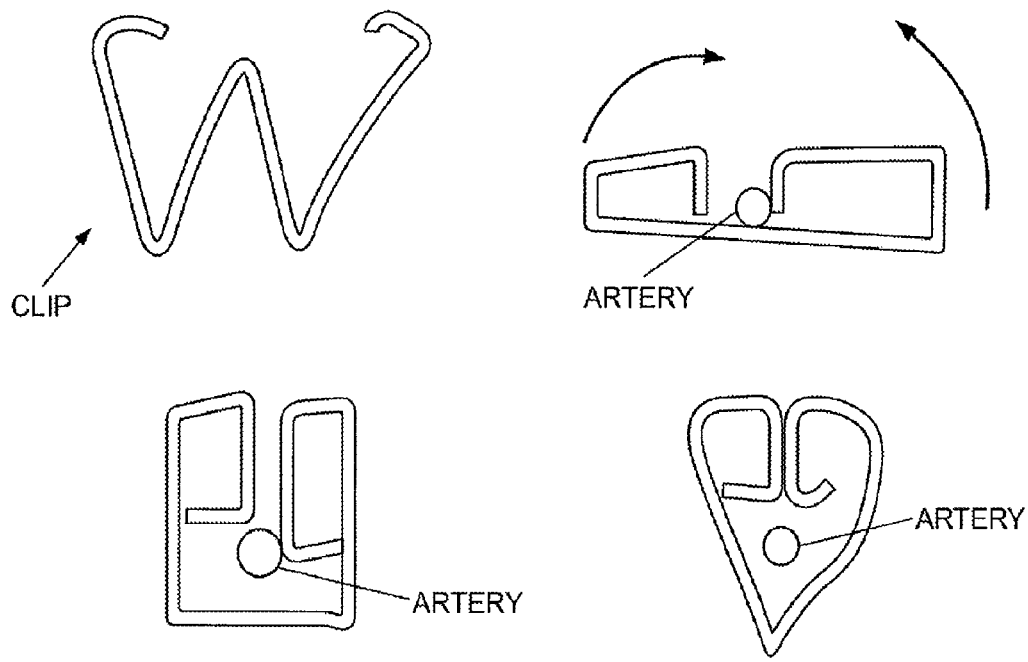
FIG. 14' shows an exemplary embodiment of a clip being bent and deformed towards its center to encompass and ligate an artery.

FIG. 14' illustrates a W-shaped clip being bent and deformed towards its center to encompass and ligate an artery.

Figure 15:
FIG. 15' illustrates variations of barbed needle clips that can be used to ligate an artery.

FIG. 15' illustrates three variations of barbed needle clips that can be used to ligate the artery. The barbs can prevent backing out once the clip is deployed in the tissue.

Figure 16A:
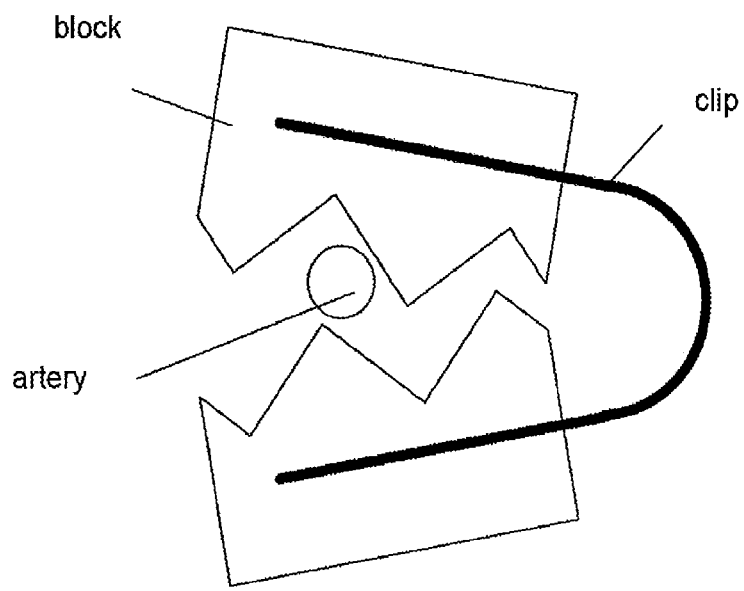
FIGS. 16A and 16B are front and oblique views, respectively, of the device with a Doppler-electrode-array.

FIGS. 16A' and 16B' illustrate a clip in an opened and closed configuration. The clip can be a Nitinol clip which remains closed in a relaxed configuration. The clip can have bioabsorbable toothed blocks at the ends of the clip arms. Once released from a deployment tool, the clip arms can angularly close and compress the artery between the bioabsorbable blocks, ligating the artery. The clip arms can be removed. The blocks can be bioabsorbed over time.

The devices and elements for performing HD and/or TOH can be located on the end of or along a flexible endoscope.

FIGS. 14A and 14B show a device that can ablate with ultrasound energy. The energy can be applied with a balloon catheter that can have an inflated balloon. The device can comprise an applicator and the balloon catheter for insertion into the anal canal for the purpose of ablating the hemorrhoidal arteries, such as the superior or middle hemorrhoidal arteries. The applicator can have a hollow core which can contain the deflated balloon catheter. The applicator can insert the balloon catheter into the anal cavity, minimizing the discomfort that may be caused when components of the catheter pass through the sensitive area below the dentate line.

FIGS. 14A and 14B illustrate that the balloon catheter can be comprised of a hollow shaft with an inflatable member, such as a balloon, at the distal end. The proximal end of the shaft can have an inflation port for inflation of the inflatable member and/or an injection port for injection of material through a distal port of the catheter. The device can have one or more ultrasound transducers, such as ultrasound crystals mounted to the radial exterior or interior of the external wall of the balloon. The ultrasound transducers can be high frequency ultrasound (HIFU) transducers. The ultrasound transducers can be located at one or more longitudinal lengths along the balloon. The ultrasound transducers can be aligned at one or more angles, with respect to the longitudinal axis of the balloon.

The inflatable member can be made of polyurethane, nylon or any number of polymeric materials. The shape of the inflatable member can be a single, cylindrical or spherical balloon. The balloon in an inflated configuration can obstruct the anal canal. The shaft of the balloon catheter can have gradations or markings, for example, to indicate the depth of insertion of the catheter into the anal canal, which in turn can result in the user knowing how far the inflatable balloon portion is inserted above the dentate line and in the region of interest to apply energy and collapse the hemorrhoidal arteries.

HIFU can be used to ablate the arteries concurrent or subsequent to Doppler ultrasound being used to locate and check for arterial flow.

FIGS. 14C and 14D illustrate that the ultrasound crystals can be mounted internal to the inflatable member on the shaft of the balloon catheter. The balloon can be filled with a liquid, for example saline solution or water. The liquid can transmit the ultrasound energy from the ultrasound transducers to the environment radially exterior to the balloon, such as mucosa and/or hemorrhoidal arteries.

Figure 16B:
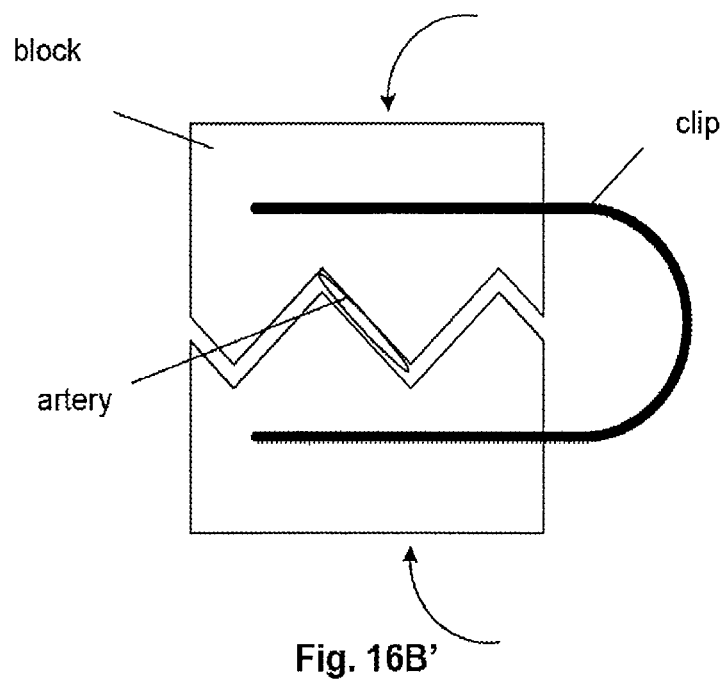

FIGS. 16A and 16B illustrate that the radiofrequency (RF) electrodes, or other ablation component, can be divided into an electrode-array controlled by an array of sensing components, such as Doppler ultrasound sensors. Each ablation-sensing pair can have an RF electrode located immediately adjacent to and/or within a Doppler sensor. The ablation-sensing pairs can be configured in an orthogonal grid, for example about eight pairs wide by about nine pairs long.

When a Doppler sensor in the array detects arterial flow, for example by detecting a pulsatile acoustic waveform, the RF electrode in the same ablation sensing pair (i.e., correlating with the position of the aforementioned, artery flow-detecting Doppler sensor) can be activated to ablate underlying tissue. The electrodes can ablate when located directly over the artery. The array can provide for a resolution for the ablation pattern corresponding to the density of the array.

The device can have a distal pad connected via a pivoting joint to a proximal handle, which is in turn connected to a central control system. The distal pad can have an array of ablation-sensing pairs. The distal pad can be a substrate for the ablation-sensing pairs. The distal pad can be made from a rigid material, such as a plastic or metal, or a resilient or non-resilient expandable balloon. The central control system can include a generator to generate the RF energy, circuitry and other electronics to generate and process Doppler signals, and a control circuit that can interpret Doppler signals to control which elements in the electrode array are turned on.

FIG. 16A illustrates that the pad can be substantially flat or planar. FIG. 16B illustrates that the pad can be a partial or complete cylinder (i.e., having a semi-circular or circular cross-section), and/or a partial arc (i.e., having a round cross-section, but not necessarily having a constant radius).

FIGS. 16C and 16D illustrate that the cylindrical or otherwise arc shape of the electrodes can cause the Doppler ultrasound energy to emanate from all points underneath the electrode array. The Doppler ultrasound can detect arteries which underlie the tissue placed under the distal pad.

The array of ultrasound elements can generate a virtual image of the arteries underlying the mucosa onto which the pad is placed. The central control system can select subsets of RF electrode elements to turn on, thus ablating only tissue underneath activated electrode elements.

Figure 9A:
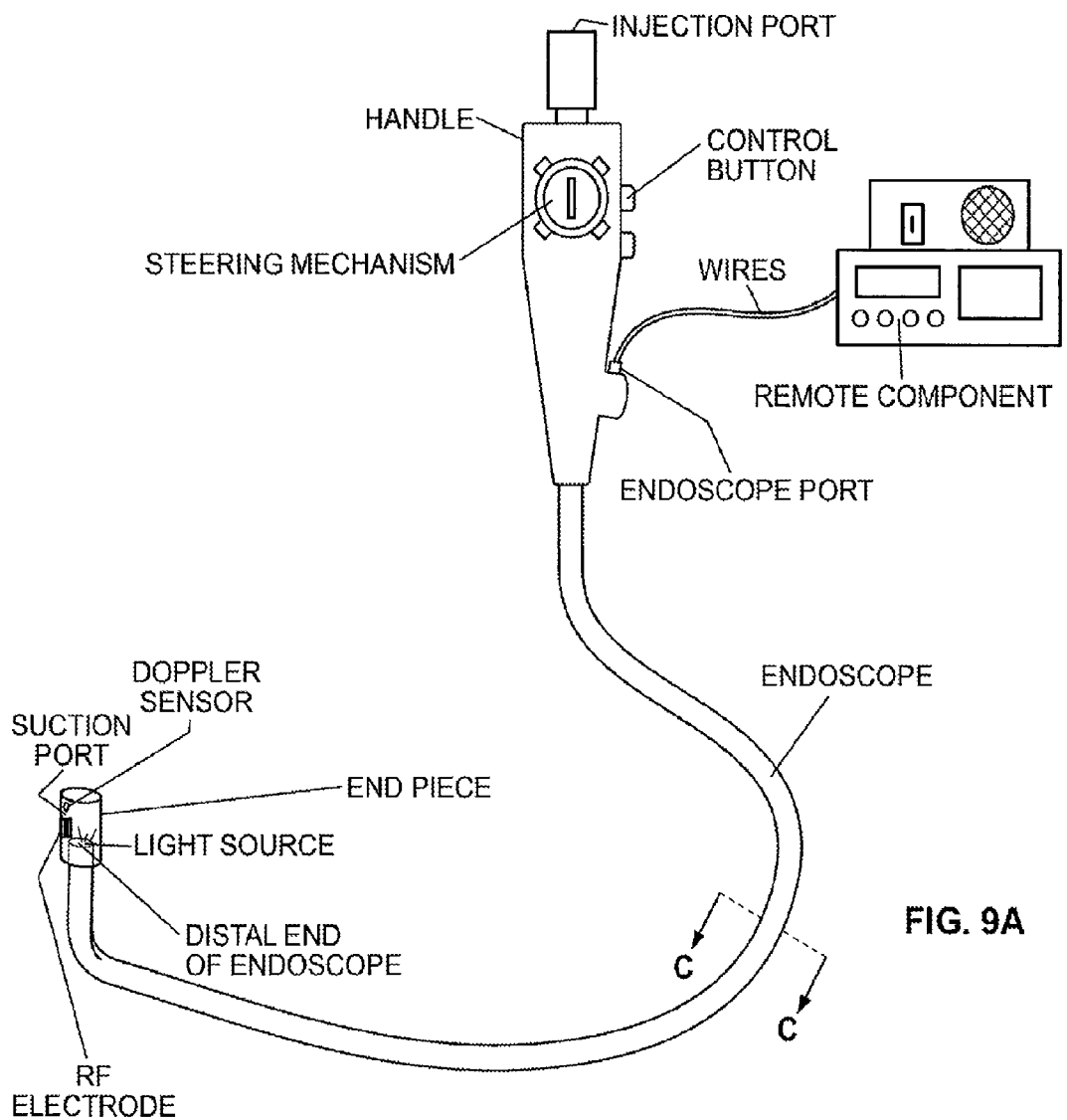
FIG. 9A illustrates a variation of the treatment device attached to video endoscope with a radio frequency electrode.

FIG. 9A illustrates an endoscopic device that can achieve HD and/or TOH via a combination of a Doppler sensor to detect the hemorrhoidal artery, and an RF electrode to ablate (e.g., heat-seal) the artery. The device can have a distal endpiece that can be fixedly or removably attached to the distal working end of an endoscope, and a remote component, such as a control box that is connected to the controls on the endoscope. The endpiece can be clipped, glued, welded, screwed, or snapped to the distal end of the endoscope. The endoscope can have an endoscope handle. The handle can have a steering mechanism that can control the angular deflection of the distal terminal tip of the endoscope and the endpiece. The endoscope, for example on the handle, can have an endoscope port. The RF electrode and wires connecting the electrode to the remote component can be slid through the endoscope port toward the distal end of the endoscope.

Figure 9B:
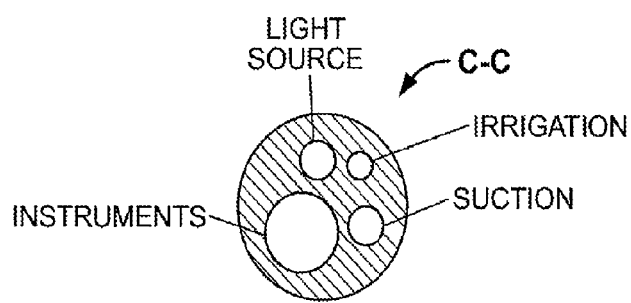
FIG. 9B illustrates a variation of cross-section C-C of FIG. 9A.

FIG. 9B illustrates that the endoscope can have lumen or channels for fluid irrigation, fluid aspiration, a light source, fiber optic camera or other visualization tools, and one or more instruments or tooling. The leads or wires for the ablation tool and/or sensor (e.g., Doppler sensor) can be slidably received in the instrument lumen. The light source can emit light at the distal end of the endoscope. The ablation tool can be one or more RF electrodes, other heat sources (e.g., electrical resistive heating coil or pad, Peltier junction), a freezing component (e.g., Peltier junction, cooling tube filled with circulating fluid at sub 0°), or combinations thereof. Although RF electrodes are described throughout, any of the alternative ablation components can be used with or in place of the RF electrodes.

The endpiece can have a Doppler sensor to locate the hemorrhoidal artery; a suction port that can grab, hold and evaginate the tissue containing the artery into the port, wherein the suction port is connected with and powered by the suction channel of the endoscope; an RF electrode(s) to heat the artery in order to seal the artery to prevent blood flow; or combinations thereof. The Doppler sensor, suction port, RF electrode(s), or combinations thereof, can be on the lateral side of the endpiece. The endpiece can be in data and energy communication with the control box, with leads, wires or tubing that can be contained in the working channels of the endoscope, and/or along the outer diameter of the endoscope.

Figure 9C:
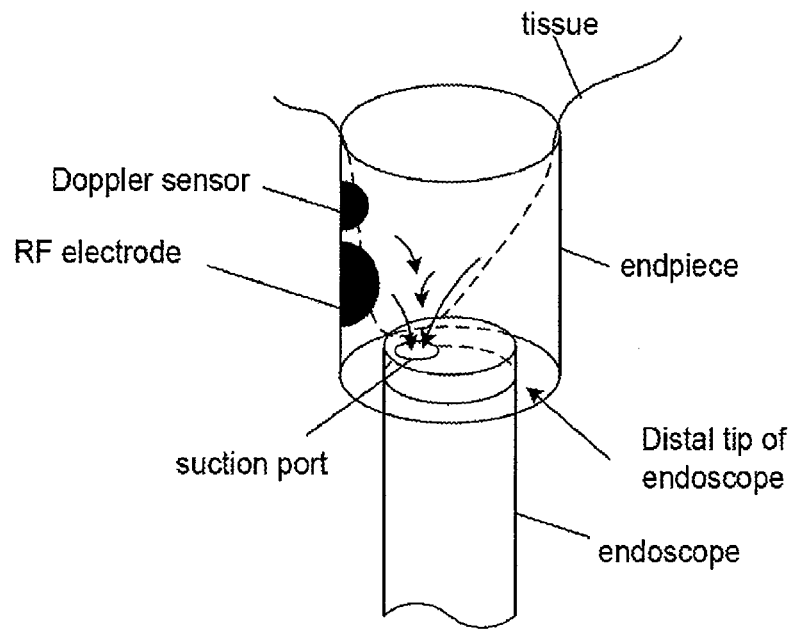
FIGS. 9C and 9D are close-up views of variations of the distal end of the endoscope and the endpiece suctioning tissue.
Figure 9D:
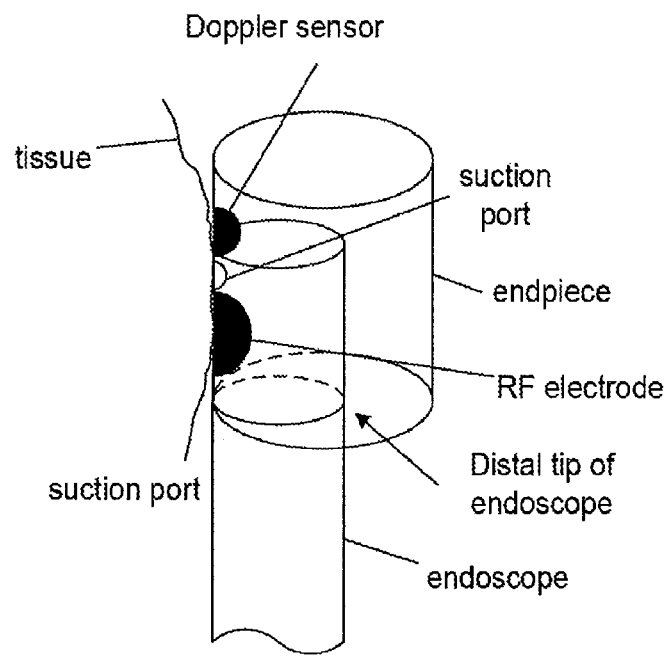

FIG. 9C illustrates that the suction port can apply suction, as shown by arrows, and draw tissue into the end piece through the open distal end of the endpiece. The suction port can be located on the distal terminal end of the endoscope.

The suction port can be positioned adjacent to the Doppler sensor and the RF electrode. The Doppler sensor and the RF electrode can be on the radially inner side of the wall of the endpiece. The tissue can be suctioned to be adjacent to and/or in contact with the Doppler sensor and the RF electrode. The endpiece can attach coaxially (i.e., with collinear longitudinal axes) with the endoscope.

FIG. 9B illustrates that the suction port can be on the lateral wall of the endpiece. The Doppler sensor and the RF electrode can be positioned immediately adjacent to the suction port. The suction port can apply suction to hold the tissue against the radial outside wall of the endpiece. The tissue can be adjacent to and/or in contact with the Doppler sensor and the RF electrode. The endpiece can attach off-axis to the endoscope, for example with the later wall of the endoscope aligned with the lateral wall of the endpiece. The endpiece can have a larger (as shown), smaller or same outer diameter as the endoscope.

The control box can have a Doppler processor which can receive a signal from the Doppler sensor positioned in the end piece and converts the signal into sound, thereby allowing the physician to hear the pulsatile flow of an artery via a speaker on the box and/or headphones. The control box can have an RF generator, which can produce the RF energy which is transmitted through the RF electrodes in the endpiece. The control box can have a computerized control system that will sense the Doppler signal to control the timing and intensity of the RF signal.

The physician can control the device via control buttons on the endoscope to control the two working channels and suction channel could be used to control the suction and RF; the physician could control the RF and suction with foot pedals; the RF & suction could be controlled via buttons on the box.

The Doppler sensor, suction port, and RF electrode can be on the lateral side of the endpiece, with visualization achieved via a mirror within the endpiece that allows the normally forward looking endoscope to look about 90° laterally. Alternatively, the endpiece could have a port on the tip that allows normal forward visualization through the endoscope. Alternatively, the mirror could be adjustable, thus allowing the user to look forward through the scope, until the scope is in place, at which point the mirror is adjusted so that the scope looks about 90° laterally.

Figure 10:
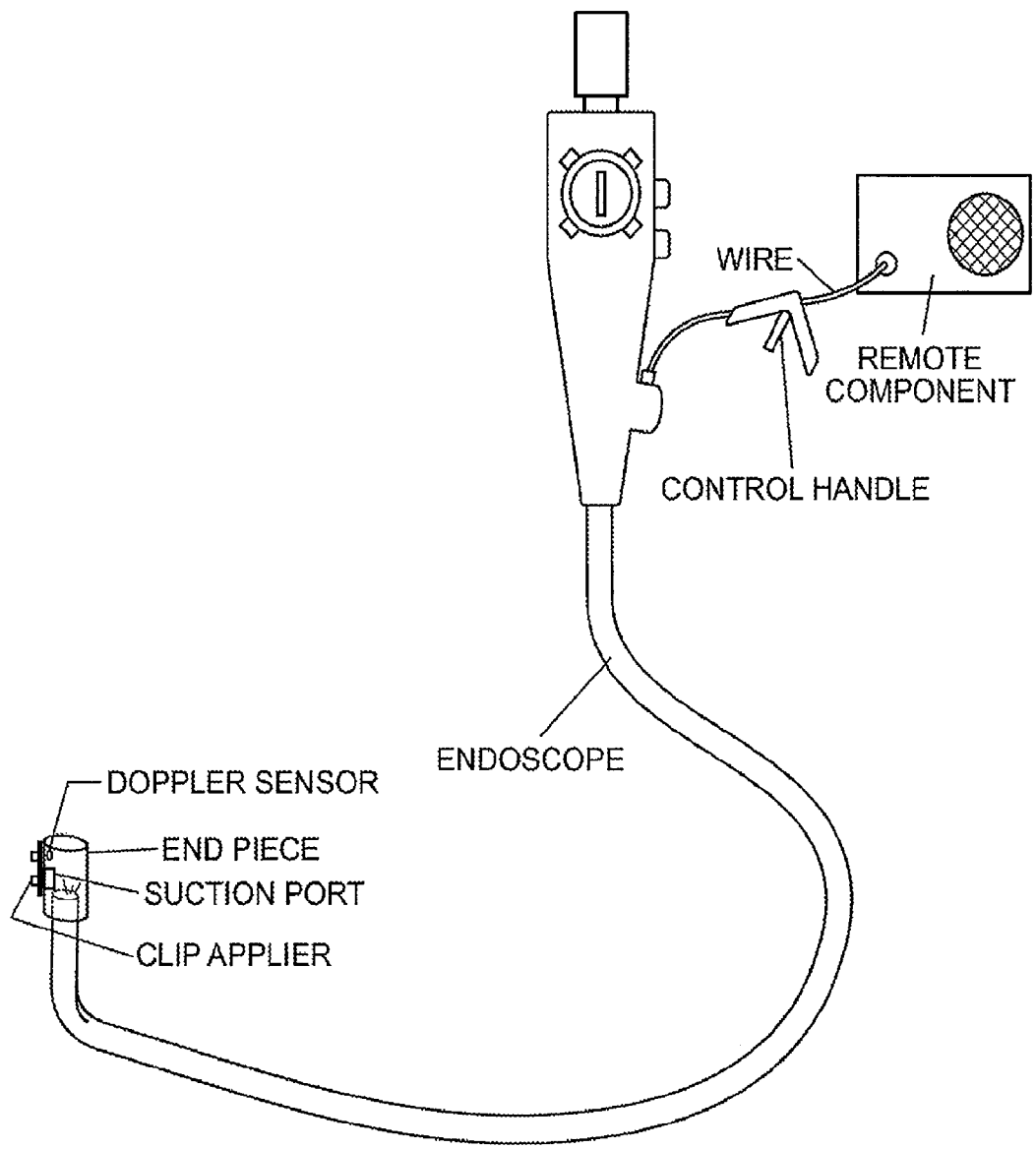
FIG. 10 illustrates a variation of the treatment device attached to a video endoscope using a clip.

FIG. 10 depicts another endoscope-based embodiment, which achieves HD and/or TOH by using mechanical devices to seal hemorrhoidal arteries and/or pexy hemorrhoids. The device can have an endpiece which is attached to the working end of the endoscope, and a control box that is connected to the controls on the endoscope.

The endpiece can have a Doppler sensor to locate the hemorrhoidal artery; a suction port that can evaginates the tissue containing the artery into the port; and any of a variety of embodiments to mechanically produce HD and/or TOH, for example the variations of FIGS. 3A through 3C, which include rubber band applicators, clip appliers, and staplers. The endpiece can communicate with the control box, with wires or tubing that either are contained in the working instrument channels of the endoscope, or along the outer diameter of the endoscope. A control handle can be attached to the wires. The control handle can be configured to release the mechanical sealing device, such as rubber bands, staples, clips or combinations thereof.

The control box can contain a Doppler processor which takes the signal from the Doppler sensor in the end piece, and converts it into sound, thereby allowing the physician to hear the pulsatile flow of an artery, via a speaker on the box or headphones. The device can have one or more components, such as actuators for example solenoids, can aid the mechanical force generation in the endpiece, and a computerized control system that can sense the Doppler signal to control mechanical components in the endpiece. The physician can control the device via the variation and elements described above for FIG. 9A. Visualization can be achieved via variations and elements similar to those described for FIG. 9A.

Method of Use

Figure 11A:
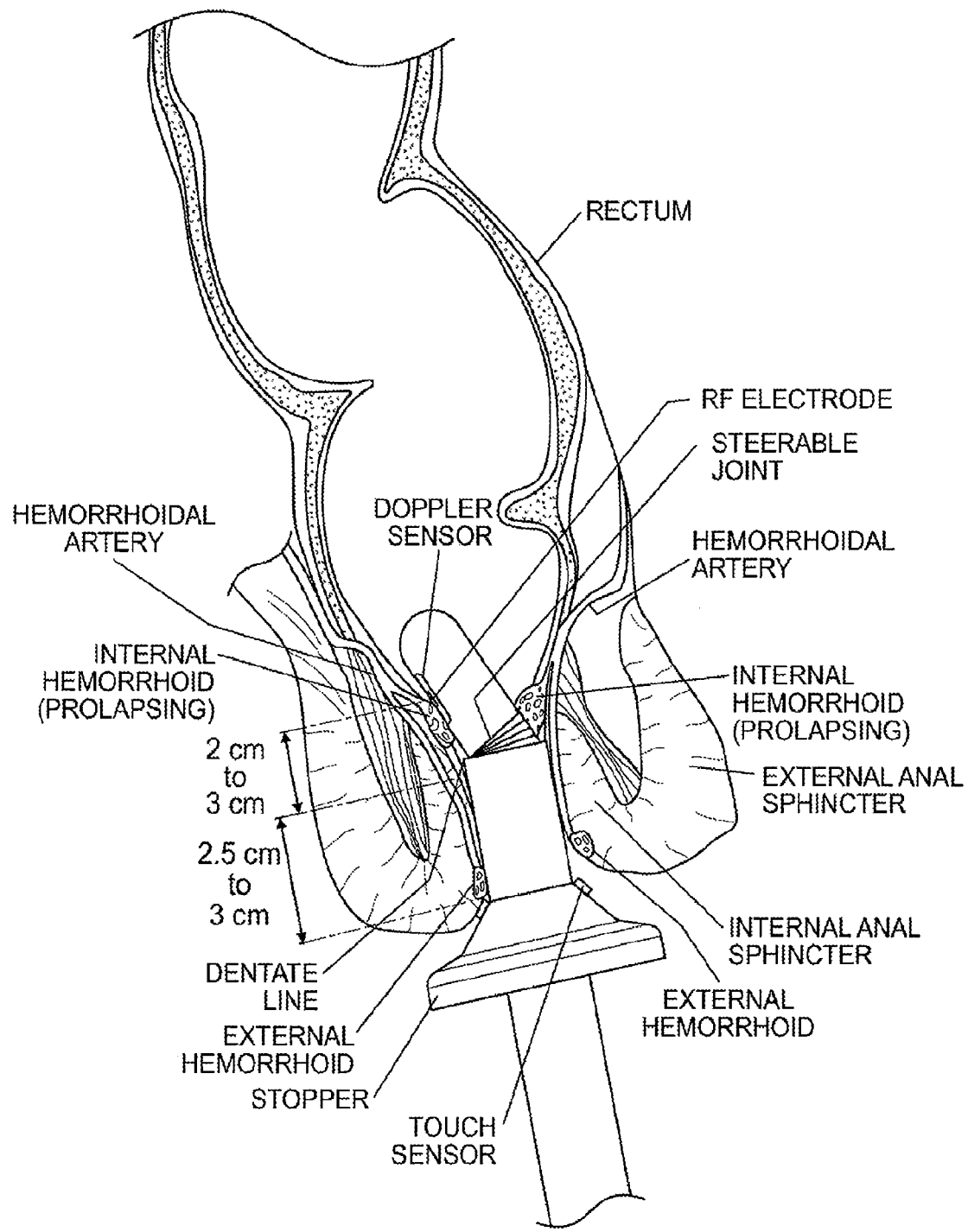
FIG. 11A is a side view of the hemorrhoid treatment device locating a superior hemorrhoidal artery above the dentate line and ligating said hemorrhoidal artery non-invasively with radio frequency energy.

As shown in FIG. 11A, the rectum has hemorrhoidal arteries, classified as superior, middle and inferior hemorrhoidal arteries. The hemorrhoidal arteries are also known as rectal arteries. The arteries targeted by the devices described herein are usually the longitudinal submucosal branches of the rectal arteries, also known as the superior hemorrhoidal arteries, and for simplicity, are often referred to as the hemorrhoidal arteries herein. The dentate line, superior/orad to which the mucosa does not register pain, is usually about 2-3 cm into the rectum past the entrance to the anal sphincter. (The anal sphincter can be classified as the internal anal sphincter and the external anal sphincter.) Hemorrhoids are located at the juncture between the hemorrhoidal arties and the veins. External hemorrhoids are located exterior to the anus. Internal hemorrhoids are located within the rectum.

Figure 11B:
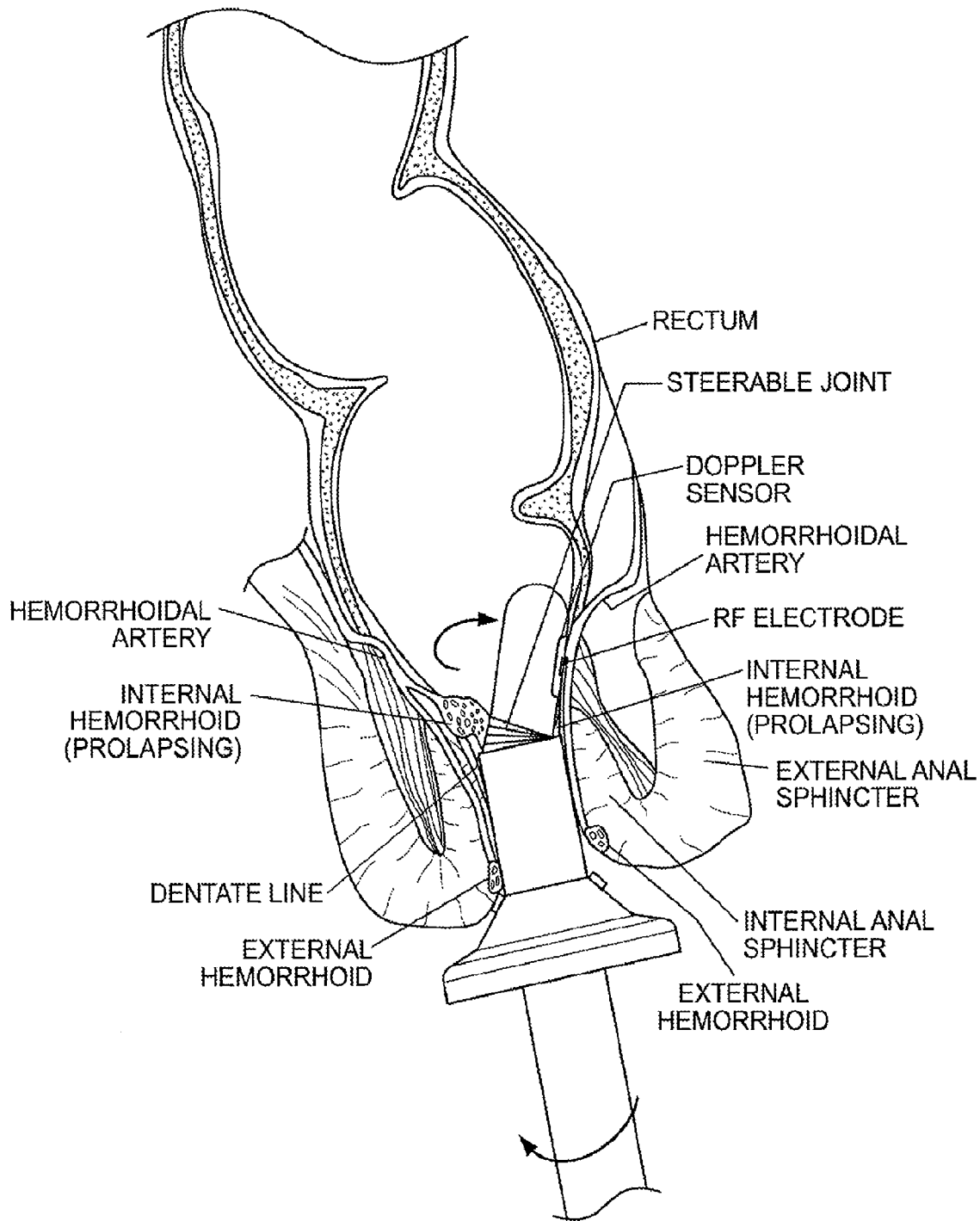
FIG. 11B is a side view of the hemorrhoid treatment device rotated about the anal canal/inferior rectum, locating and ligating another hemorrhoidal artery above the dentate line non-invasively.

FIGS. 11A and 11B illustrates the method of treating hemorrhoids with minimal or no pain. As shown in FIG. 11A, the device can be inserted into the anus until at least one of a pressure-sensing touch sensor attached to the distal end of the stopper is in contact with the external anus, or when the insertion stopper stops the device from being further inserted into the anus. The Doppler sensor and RF electrode can be about 2-3 cm above or superior to the dentate line at this part of the procedure. Next, the user/operator can articulate the steerable joint to enable the distal surface of the device to be in contact with the interior wall of the rectum. The device is then rotated until the Doppler transducer picks up signals of arterial flow beneath the rectum that the transducer is in contact with.

At this point, the device has successfully located a hemorrhoidal artery, such as a superior hemorrhoidal artery. Next, ablation energy is delivered through the electrode that is adjacent to the Doppler transducer to the hemorrhoidal artery to ligate or ablate the artery. For example, radiofrequency energy can be delivered to precisely increase the temperature of the hemorrhoidal artery to a temperature above 85 deg Celsius. Fibrotic closure of the artery or plexus occurs when subjected to heat above 85 degrees Celsius. As neighboring tissue surrounding the hemorrhoidal artery is mucosal or sub-mucosal tissue, any potential collateral injury (if any) due to the energy source may be healed with minimal inflammatory response or clinical complications. Thermal or ablative energy is delivered until the Doppler transducer does not pick up any signals.

At this point, the hemorrhoidal artery that is subjected to the thermal or ablative energy would be ligated, thereby stopping blood flow downstream from the ligated section to the enlarged and engorged hemorrhoidal plexus. This consequently over time will reduce the engorged hemorrhoidal plexus and definitively treat the prolapsed hemorrhoids downstream of the ligated hemorrhoidal artery.

Figure 11C:
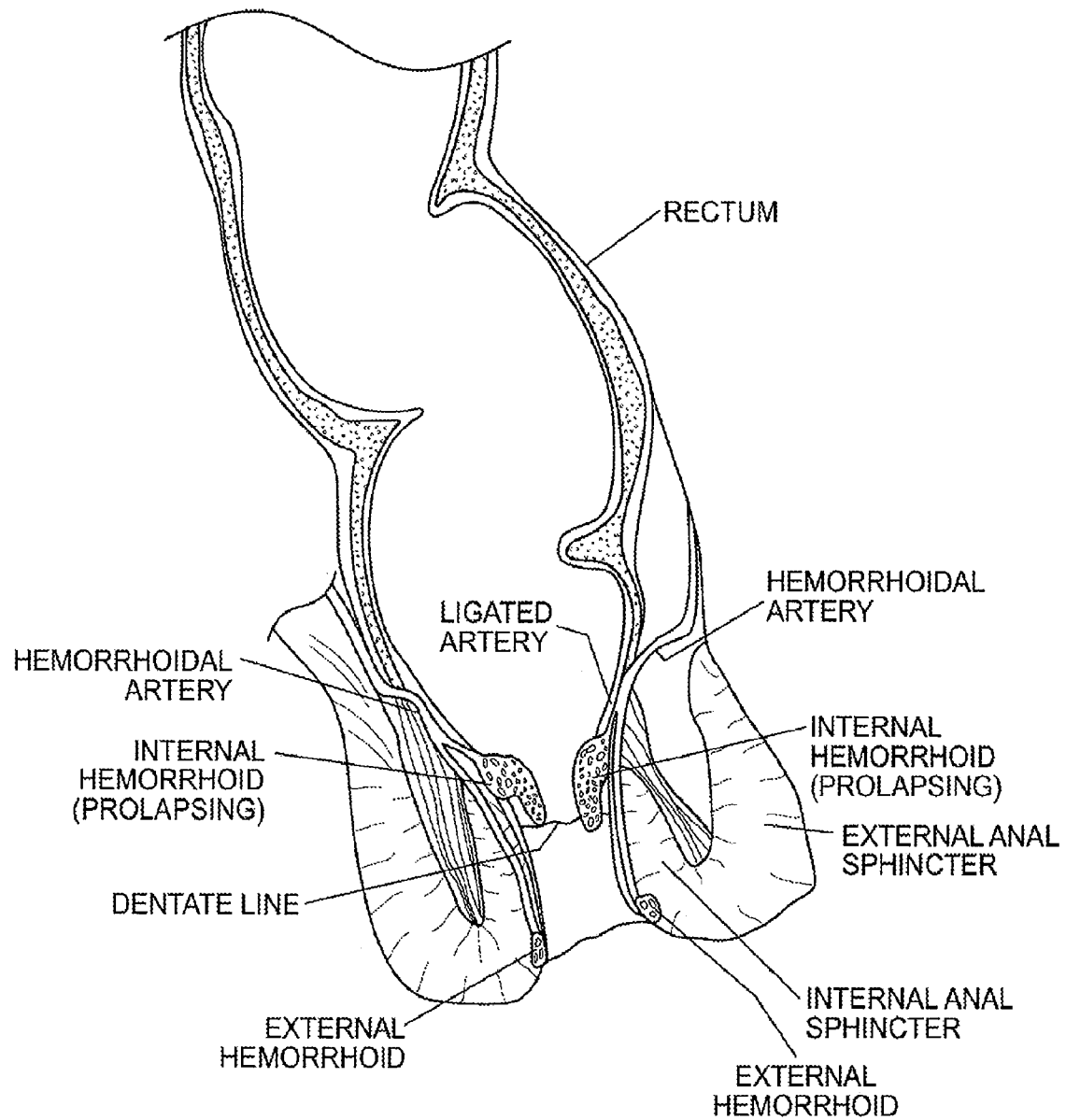
FIG. 11C is a cross sectional side view of the anus and rectum with hemorrhoidal arteries above the dentate line fully ligated and stopping blood flow to prolapsed hemorrhoid plexus downstream.

As shown in FIG. 11B, the procedure can then be repeated while slowly rotating, as shown by arrows, the device circumferentially for the fully 360 degrees until all hemorrhoidal arteries close to the surface of the interior rectal wall are ligated. There are often six and sometimes up to ten hemorrhoidal arteries (there is a natural variation within the population), any or all of which can be ligated. The user/operator can then perform a confirmation check by rotating the device for another 360 degrees to detect any blood flow detected by the Doppler sensor indicating any hemorrhoidal artery that might have been missed and not ligated previously. The confirmation check can be performed until the Doppler sensor detects no blood flow to the downstream engorged hemorrhoidal prolapsed plexi, as shown in FIG. 11C. The ligated artery will no longer deliver blood to the hemorrhoid.

Methods described in FIGS. 11A through 11C describe a rapid, convenient and simple way to perform minimally invasive, painless (or minimally painful) hemorrhoids treatment as both the hemorrhoidal artery detector, such as the Doppler transducer, and the artery ligation tool, such as the RF electrode, are built into a single device with no working channels required. No tool exchanges, such as passing suture and needles, laser coagulation device, or other energy ablation tools, through the working channel of an anoscope or a dilator with Doppler transducer sensors, is required to perform the treatment. Apparati and methods to access the anus and treat hemorrhoids that do not require a patient's anal canal to be dilated before said invention can be inserted are disclosed. The device and method herein minimize prolonged anal dilation, which has been known to be a potential cause of fecal incontinence and anal fissure.

The system illustrated in FIGS. 11A through 11C can comprise a control circuit which can automatically determine how long to keep activated the ablation energy source and the optimal power requirements, based on feedback from the artery and arterial flow sensor. As shown in FIG. 12, the system can begin by detecting (i.e., measuring) if arterial blood flow is detectable beneath the mucosa on which the ablating member sits. If blood flow is detected, the physician is alerted (e.g., with an acoustic signal through a speaker or headphones) to the presence of arterial blood flow, and the ablation component can be activated and ablation energy can be applied to the region of mucosa under which blood flow was detected. If blood flow is not detected, the physician is alerted to the absence of arterial blood flow (e.g., with an acoustic signal through a speaker or headphones different from the signal when blood flow is detected, or with the absence of an acoustic signal), and no ablation energy is applied. A loop continues in this manner until no blood flow is detected or a safety shutoff is activated.

The safety shut-off can be a timer mechanism in which ablation energy is shut off because the ablation energy has been supplied for a length of time meeting or exceeding a safety threshold, such as the threshold length of time that has been found to be safe. The safety shut-off can employ a sensor, such as an impedance sensor, which shuts off the ablation energy if the sensed variable (e.g., time, temperature, or combinations thereof) enters a range that is considered unsafe or undesirable. The safety shutoff can be a physician-operated over-ride switch, which the physician or operator can flip or otherwise activate at any time during the procedure.

The device illustrated in FIG. 13A is a variation of the device that can have an expandable member at the distal section. The expandable member can be inserted into a patient's anal canal while in a narrow profile so as to minimize or prevent the need for dilation of the anus.

Figure 13B:
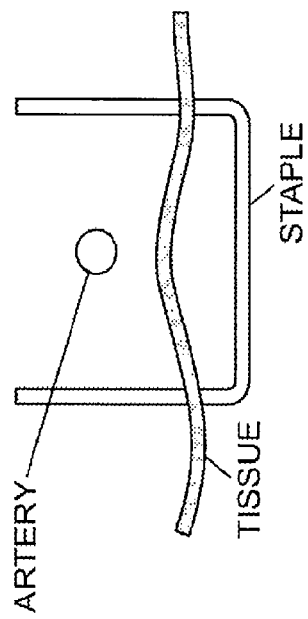
FIG. 13B is a side view of the same hemorrhoid treatment device the distal expandable basket fully deployed and in contact with the inner wall of the rectum above the dentate line.
Figure 13A:
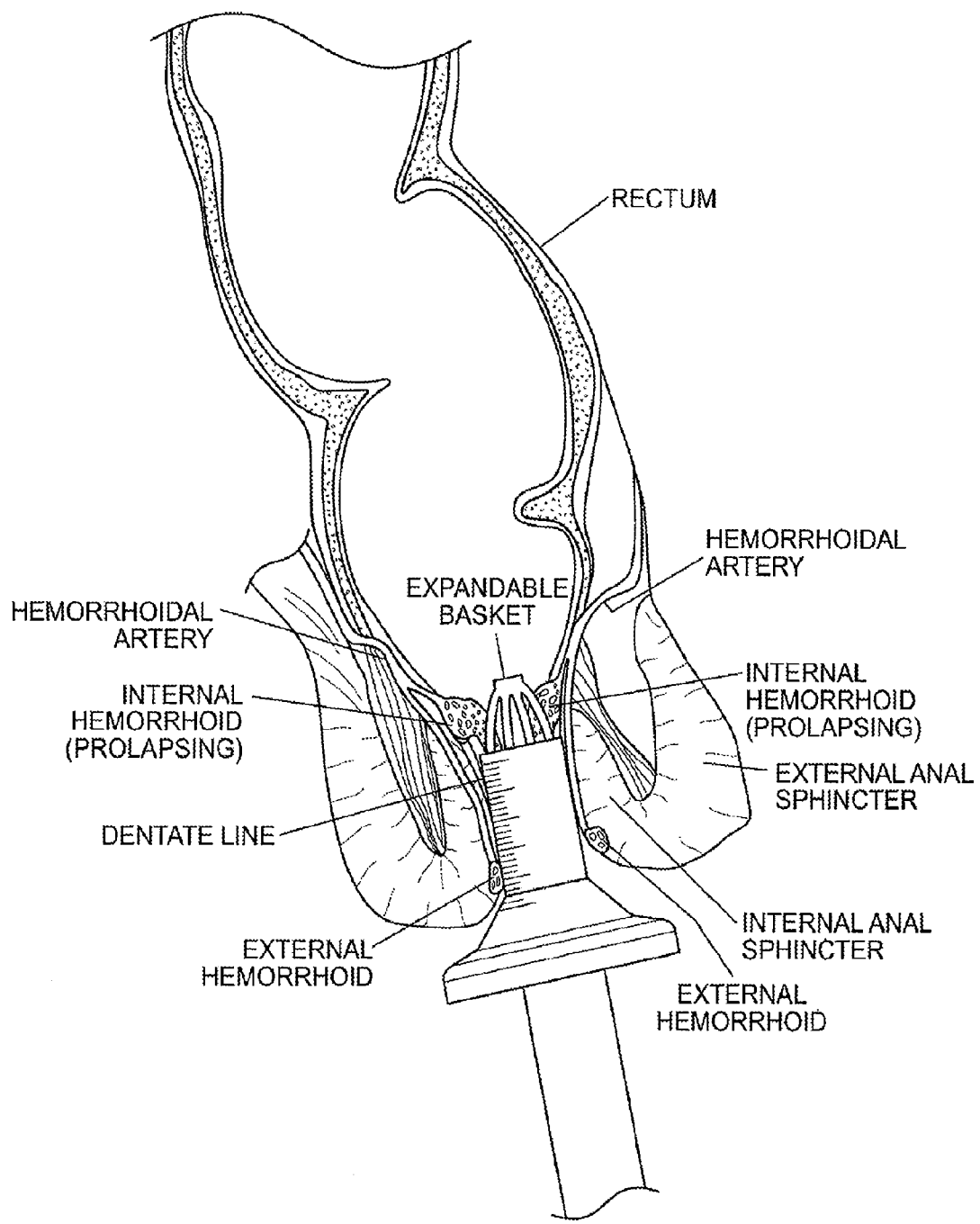
Figure 13B:
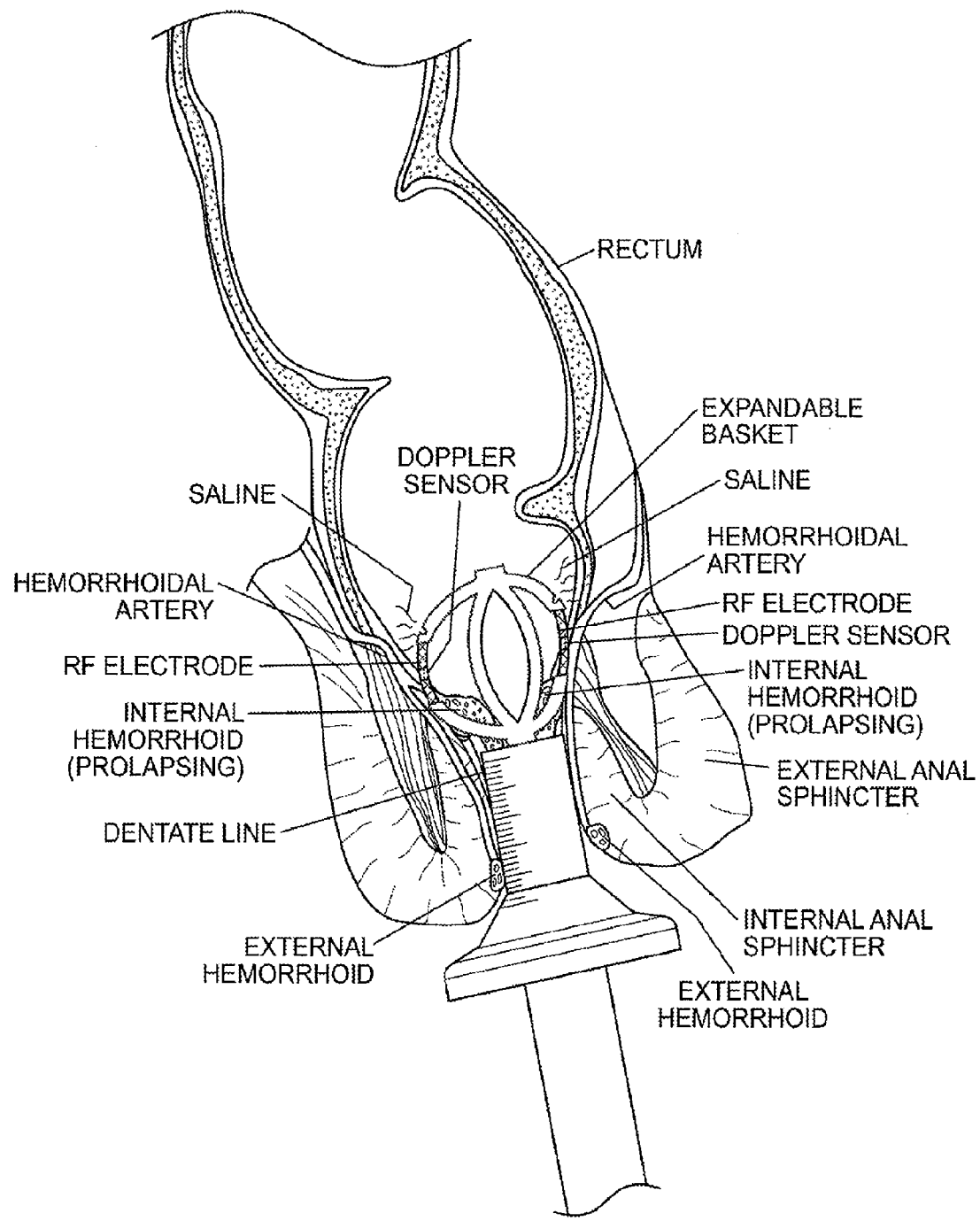

FIG. 13B illustrates that once the device is inserted to the specified length, a plunger on the proximal end is pushed, which opens the expandable unit at the distal end of the device inside the rectum. The expandable unit can be a basket, balloon, mesh, etc. The basket has several struts that expand such that it conforms to the rectal wall circumferentially. This provides support to keep the device in a fixed position once properly positioned. When the distal end is not completely expanded it can be rotated about its axis until the Doppler picks up signal so as to localize the hemorrhoidal arteries. One or more of the basket struts can have an irrigation port on the distal end to infuse cold saline to cool the tissue electrode interface. Proximal to the infusion port is the RF electrode, which ablates the hemorrhoidal artery. When the user locates the artery by Doppler, the expandable member is fully expanded and the saline irrigation and RF electrode are turned on at the same time. Ablation occurs until there is no more Doppler signal. The device can then be rotated until the Doppler picks up another artery, which will be ablated in a similar fashion. The procedure can be performed until no further arteries are located.

The expandable basket can be made out of heat-shaped metal such as Nitinol. The wires for the RF electrode and the Doppler transducer as well as the irrigation catheter is contained within a sheath surrounding the exterior of one or more of the basket struts. These components are then contained within body of the device and exit individually at the handle. The Doppler transducer is located beneath the RF transducer so that it can be used to determine that that the artery has been completely ablated. When there is no further flow as measured by the Doppler it will automatically turn off the RF transducer. The expandable member can be removed from and reinserted into the body of the device.

The device does not require anal dilation, and precisely allows for a more precise method to ablate tissue and spare surrounding structures. This will eliminate the dangers of suturing the internal anal sphincter, which can cause severe spasm and pain and can lead to fecal incontinence. The expandable member allows for insertion of a small diameter device that conforms to the rectal wall and keeps the device in the proper location.

Figure 15A:
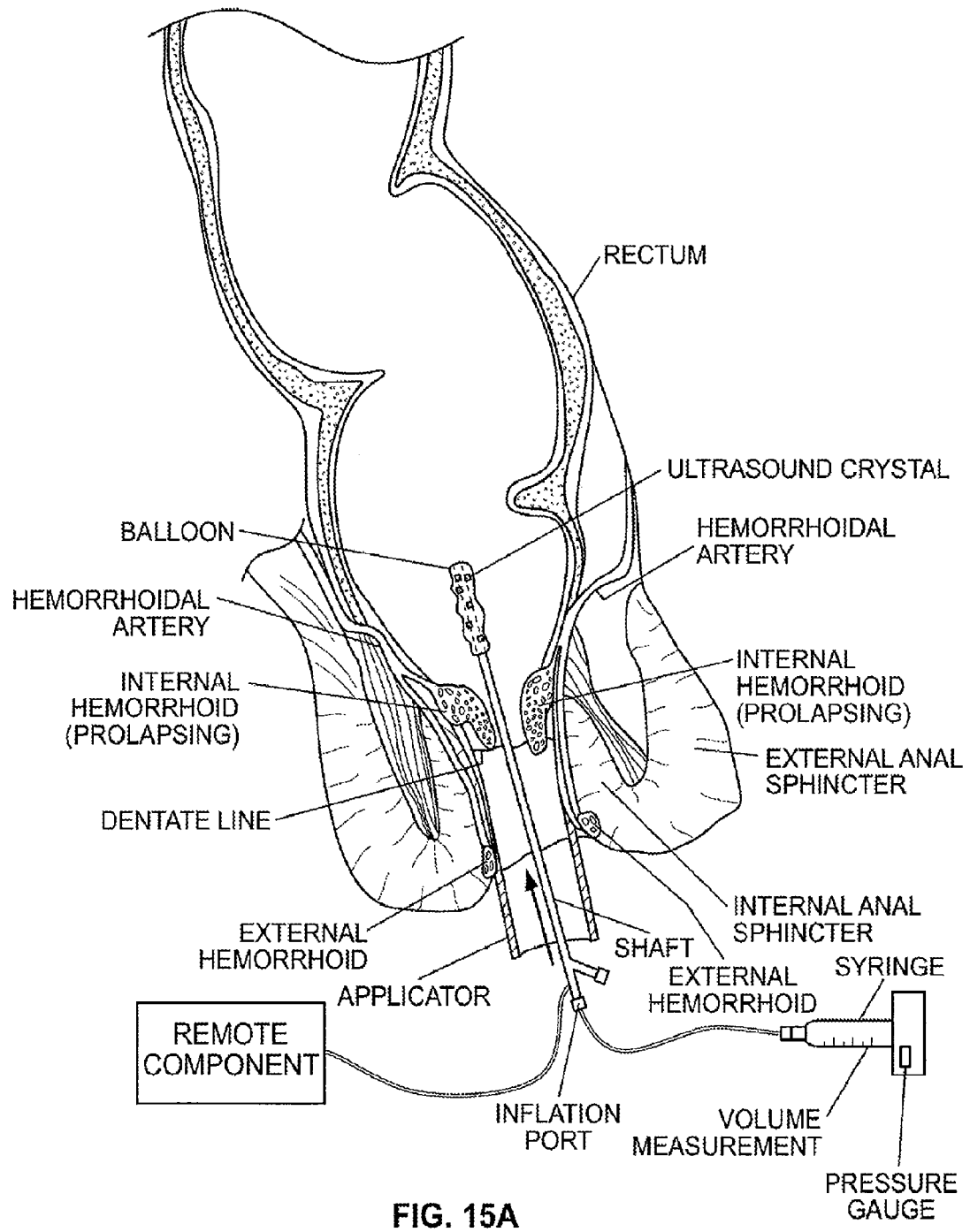
FIG. 15A illustrates a variation of a method for insertion of the deflated balloon catheter into the rectum through the applicator.

FIG. 15A illustrates that the catheter can be inserted, as shown by arrow, through an applicator into a region of interest in the rectum. The applicator can be rigid and placed in the anus. For example, the applicator can be a disposable hollow cylinder similar to a tampon applicator, with the catheter running through the lumen of the applicator. The applicator can dilate the anus. The applicator is not required. The distal end of the catheter can have a balloon. The balloon can be deflated when placed through the anus. The balloon can have ultrasound crystals, for example on the radially outer surface of the balloon wall. Other artery sealing technologies described herein (e.g., radiofrequency electrodes, sclerosant delivery needles, etc) could be on the outer surface of the balloon wall as well. The inflation port can be in fluid communication with a syringe. The syringe can have demarcated volume measurements and can have a pressure gauge that can indicate (e.g., digitally) the pressure of fluid delivery from the syringe.

Figure 15B:
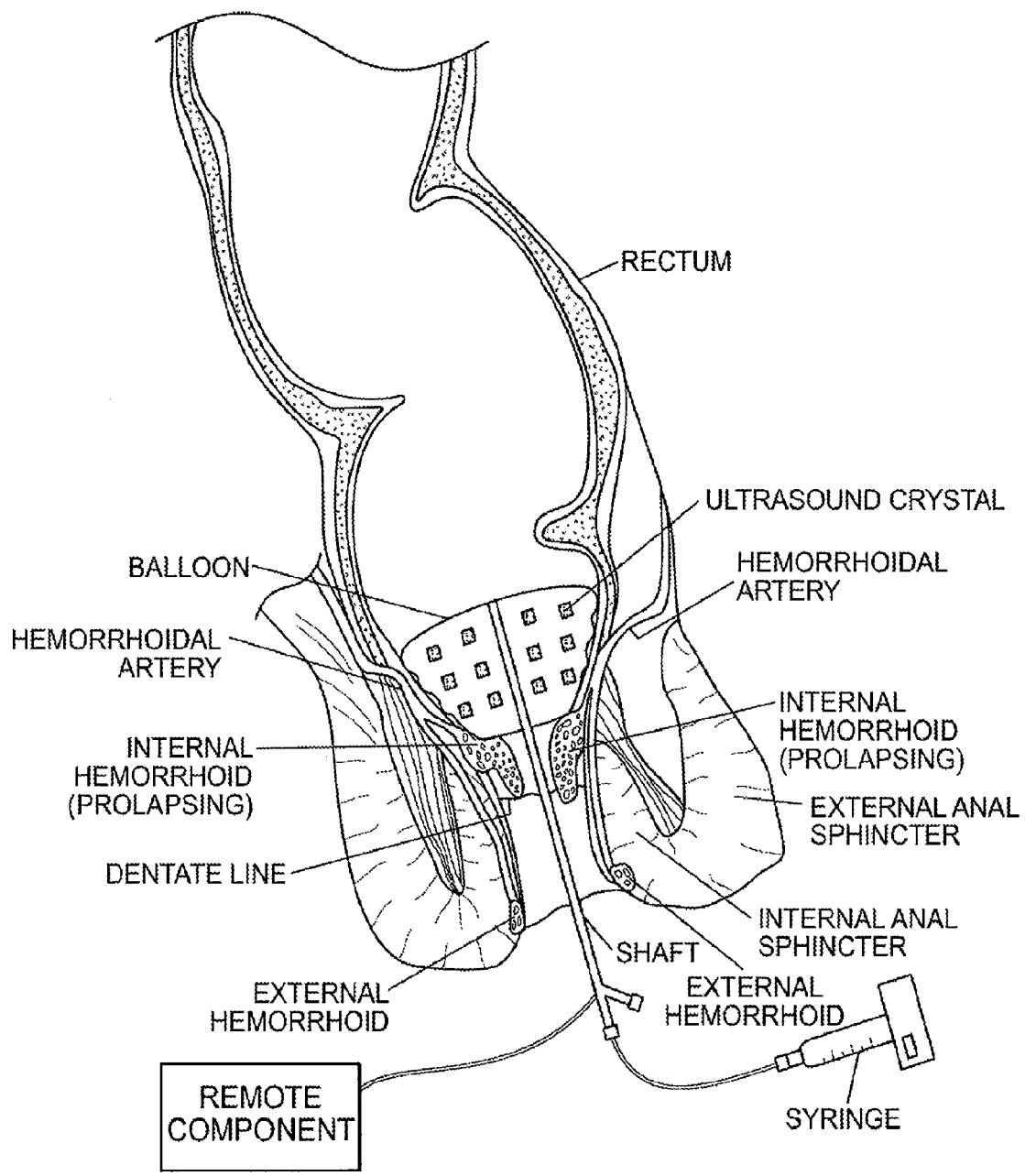
FIG. 15B illustrates a variation of a method for inflation of the balloon catheter using a pressure and/or volume-controlled syringe.

FIG. 15B illustrates that once the catheter has been inserted into the region of interest, the balloon can be inflated using the syringe that can register pressure and/or volume readings. The balloon can be inflated with saline, contrast medium or other liquid materials, or gas such as air, oxygen, or carbon dioxide. The balloon can be inflated until there is a sudden increase in pressure, indicating that the balloon is in contact with the walls of the anal canal. The user can then activate the ultrasound, or other artery-sealing modality, which applies energy through the walls of the rectum, thereby collapsing the hemorrhoidal artery supply that lies beneath.

Figure 15C:
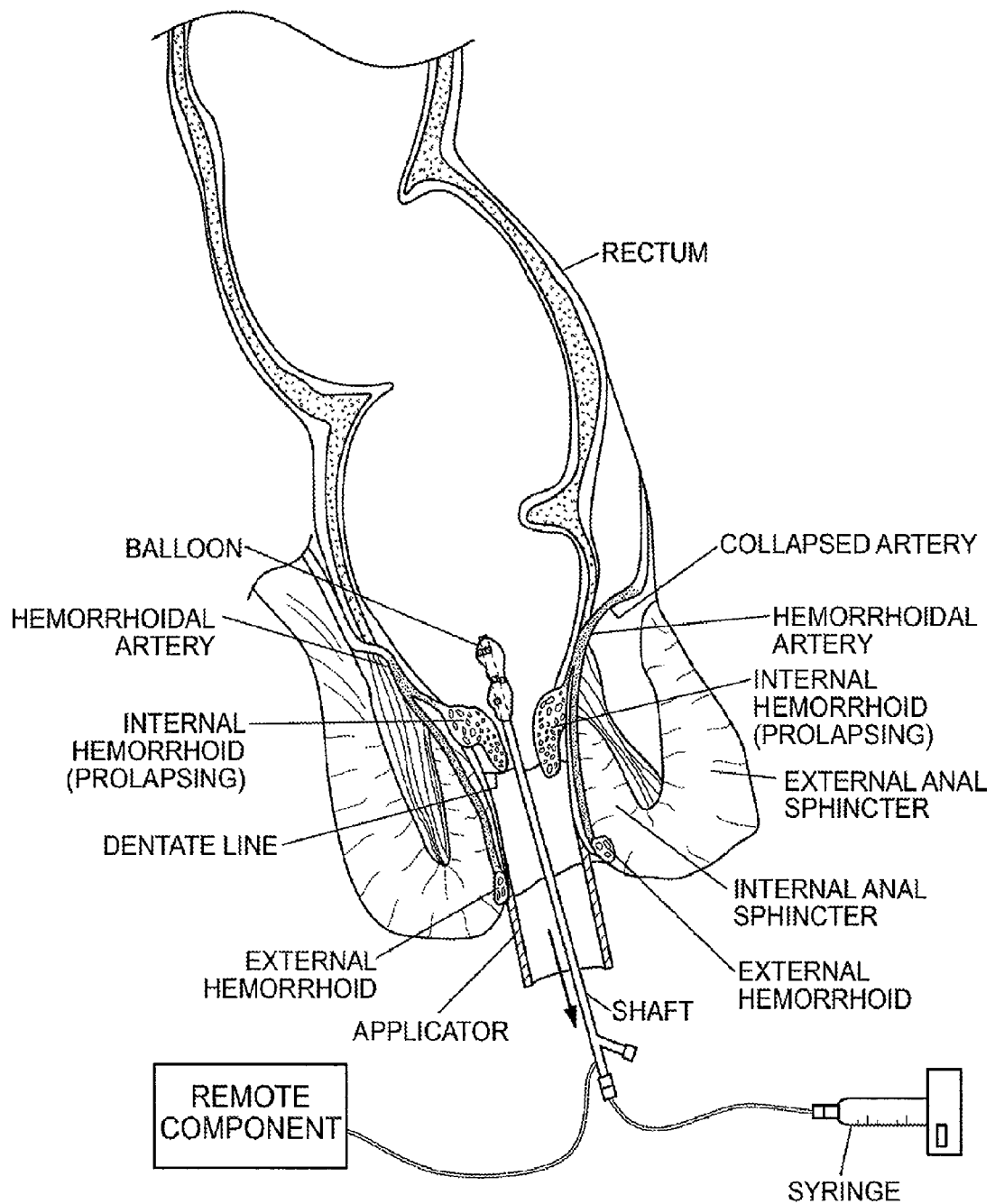
FIG. 15C illustrates a variation of a method for removal of a deflated balloon catheter with hemorrhoidal arteries in a collapsed state.

FIG. 15C illustrates that the catheter can then be deflated using the syringe and removed from the anus through the applicator. The user can then remove the applicator from the anal canal.

Figure 17:
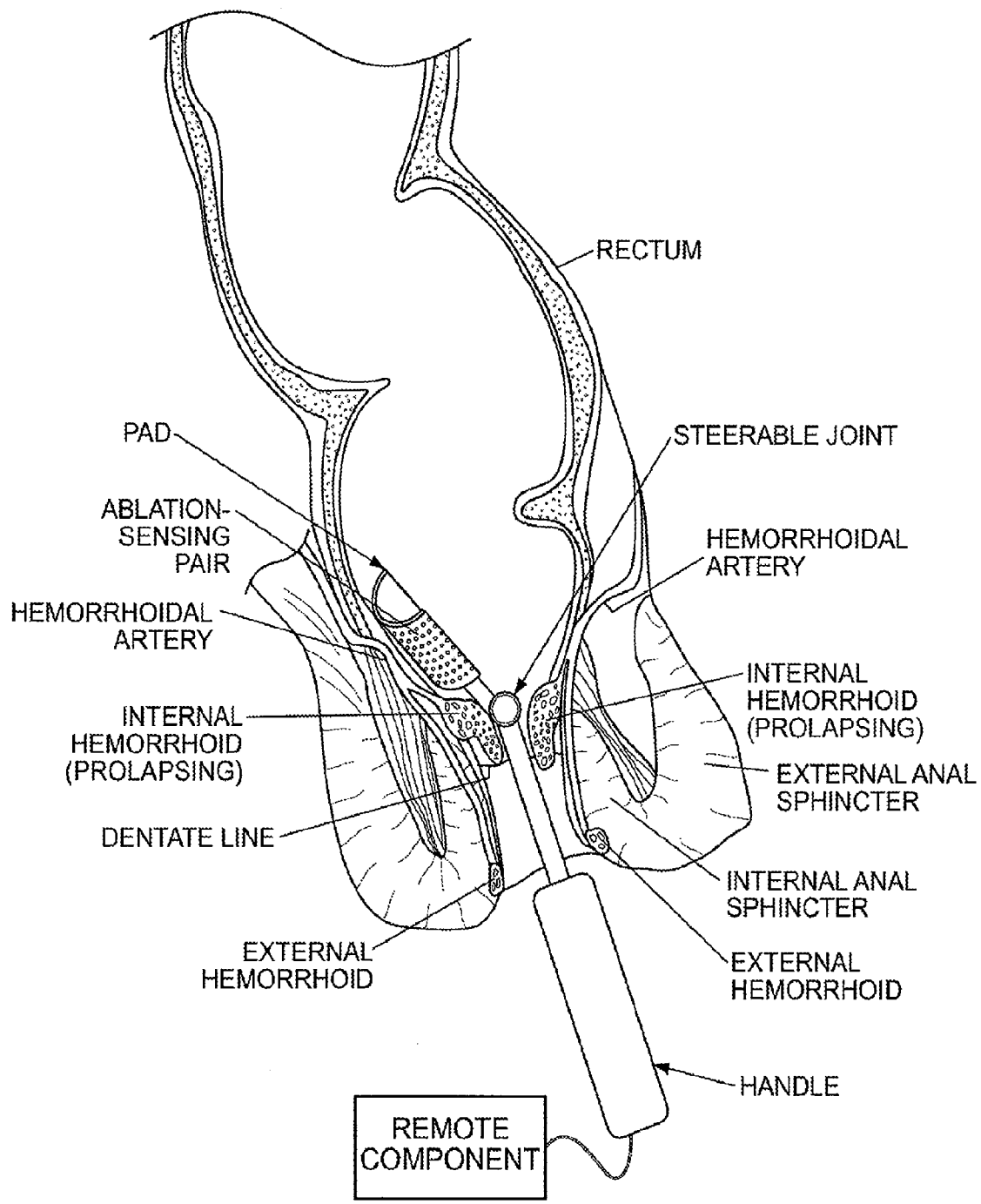
FIG. 17 illustrates a method for insertion of the Doppler-RF-Electrode-Array device into the anus, placing the pad onto mucosa above the dentate line.
Figure 18A:
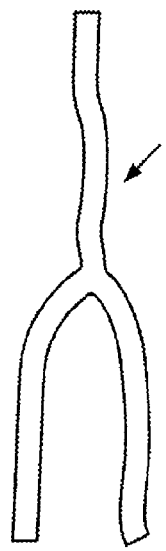
FIG. 18A is a rear view of a branching hemorrhoidal artery.
Figure 18B:
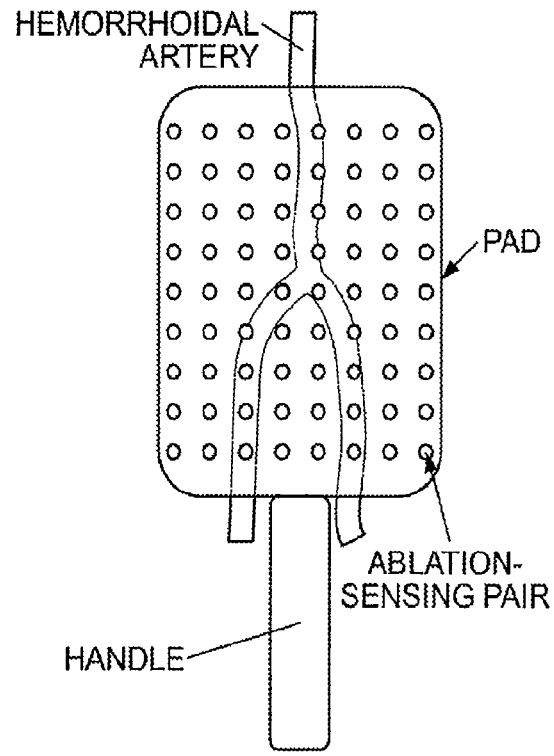
FIG. 18B is a rear view of the Doppler-RF-Electrode-Array being placed on top of mucosa overlying the branching hemorrhoidal artery of FIG. 18A.
Figure 18C:
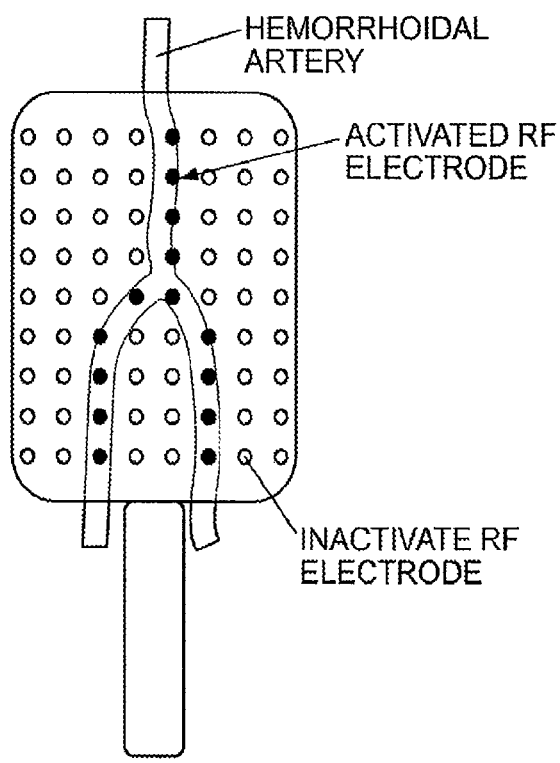
FIG. 18C is a rear view of a variation of a method for ablating the artery of FIG. 18A by activating a subset of the RF electrode elements in the electrode array.
Figure 18D:
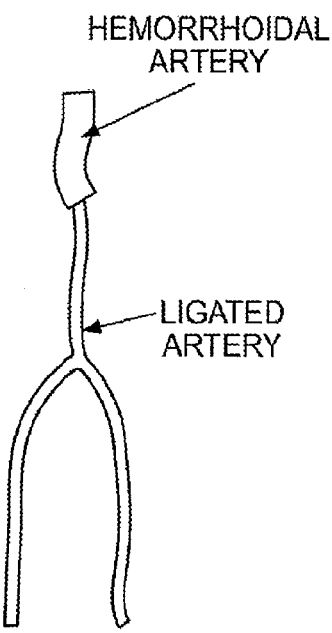
FIG. 18D is a rear view of the ablated hemorrhoidal artery of FIG. 18A.

FIG. 17 illustrates that the distal pad of an artery sealing device can be inserted into the rectum. The pad can have an array of ablation-sensing pairs. The pad can be placed firmly on the mucosa of a first region in the rectum, with firm placement aided by the pivoting steerable joint between the distal pad and handle. The Doppler element array then can creates a virtual image of the arteries underlying the mucosa onto which the pad is placed (shown in FIGS. 18A and 18B). The virtual image of the artery geometry is sent to the central control system (e.g., in the remote component), which can then activate only the RF electrode elements which overlie an artery. FIG. 18C illustrates that the RF electrodes overlying arteries are activated RF electrodes and the RF electrodes overlying non-arterial tissue are inactive RF electrodes. The RF energy emanating from each activated RF electrode can ablate underlying arteries, producing coagulation, collapse, scarring, and cessation of blood flow through the affected artery segments. FIG. 18D illustrates that the hemorrhoidal artery can be ligated where treated by the RF electrodes, but not elsewhere. Likewise, tissue surrounding the artery can be substantially unaffected by the ablation. The device can then rotated along its long axis repeatedly so that the pad comes into contact with a 360-degree ring of mucosa, ablating most or all arteries in a ring of mucosa above the dentate line. The ablation-sensing pairs can remain active as the pad is rotated. If desired, ablation can occur concurrent with the rotation of the pad along the mucosa. The Doppler-RF Electrode-Array device can minimize or completely prevent substantial collateral damage by only emitting RF energy directly on top of arteries.

The Doppler array can create a virtual image of the underlying arteries. The Doppler array can be an array of Doppler ultrasound elements directed perpendicularly to the distal pad surface. The Doppler array can also be fewer Doppler ultrasound elements directed at an acute angle to the distal pad surface, with the entire plane of the ultrasound signal providing Doppler information, as in the operation of transthroacic ultrasound images of the blood flows in the heart. The Doppler array can also be smaller set of ultrasound elements which move or pivot periodically to survey more surface area.

Said distal pad's array of RF electrode elements can be a unipolar RF ablation lead with a grounding pad placed on a remote site on the patient. Alternatively, each RF electrode, or pixel, can be bipolar itself, containing both a positive and negative lead within the element. Alternatively, the adjacent RF electrodes within the array can alternate between positive and negative leads.

The distal pad can be a cylinder so that a complete, 360-degree ring of mucosa is simultaneously contacted by the pad. Said 360-degree-ring distal pad can be radially expandable to press the surface of the pad flush against the mucosa.

Figure 19A:
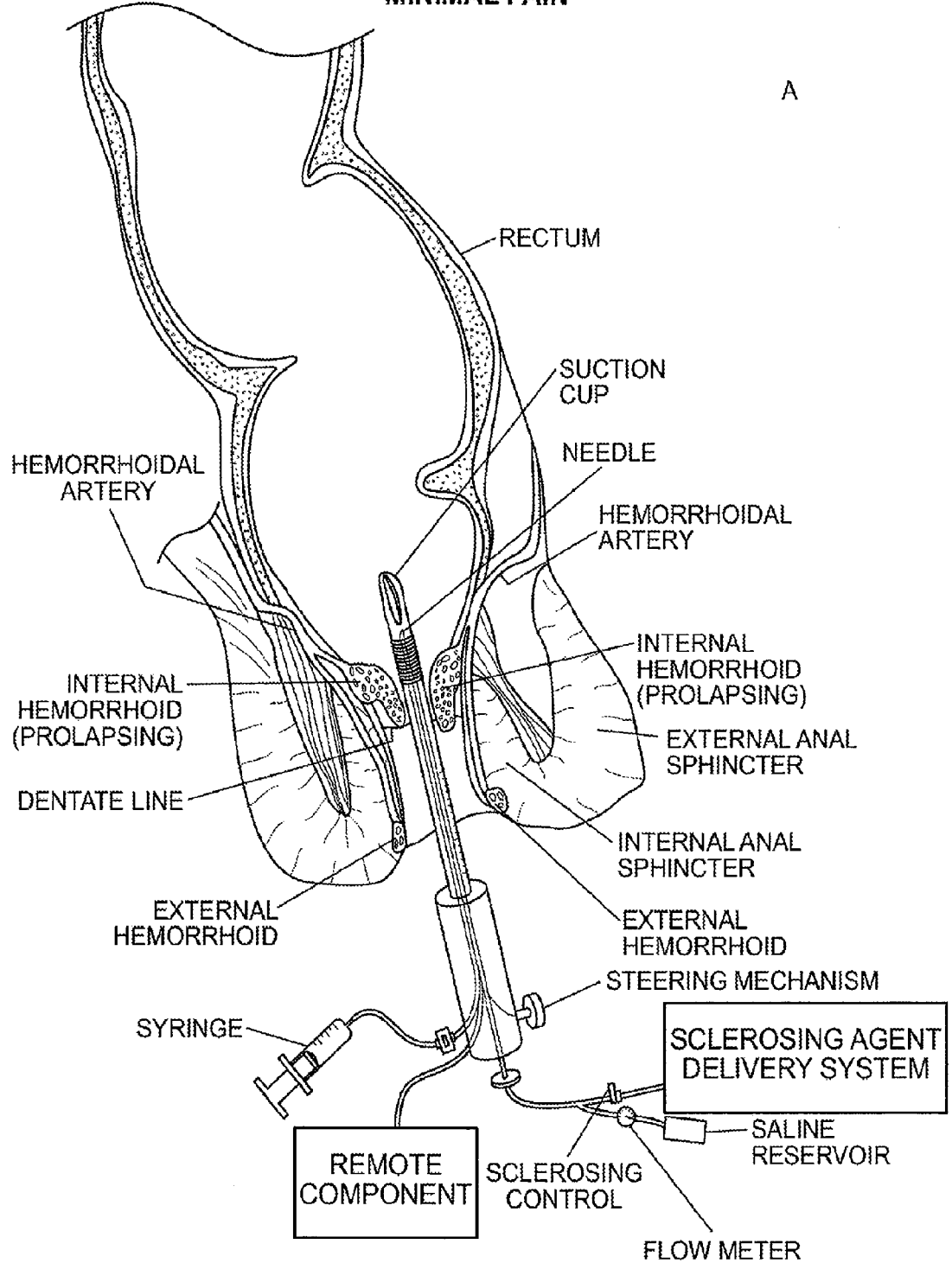
FIG. 19A is a side view of the hemorrhoid treatment device that utilizes steam energy inserted through the anus without requiring dilation of the anus.

FIG. 19A illustrates that the device can emit steam as the energy source, a sclerosing agent for hemorrhoidal artery ligation (e.g., as opposed to RF). The steam can be delivered into or adjacent to the artery and used to ablate the artery. Alternatively, instead of steam or in combination with steam, the sclerosing agent can be alcohol such as ethanol, phenol, methanol, isopropyl alcohol, butanol, ethylene glycol; aldehydes such as formaldehyde; acids, such as hydrochloric acid, hydrofluoric acid, acetic acid, sulfuric acid; strongly alkaline (base) materials such as urea, lye, hydrogen perchlorate; quinine, urea hydrochloride, hypertonic salt solution, vegetable oil, or combinations thereof. The sclerosing agent can be delivered into or adjacent to the target artery. The distal section of the device can comprise a collapsible suction cup attached to an articulating joint with a needle protected inside the collapsed or contracted suction cup. The distal edge of the suction cup can have a Doppler sensor. A sclerosing agent delivery system, such as a sclerosing agent reservoir and pump can be in controllable fluid communication with the needle. The sclerosing agent delivery system can be replaced with or used in conjunction with a steam generator in regulated fluid communication with the needle. A sclerosing control can regulate the sclerosing agent delivered to the needle. A saline reservoir (e.g., bag) can also be in fluid communication with the needle. A flow meter can measure and regulate the delivery of saline.

Figure 19B:
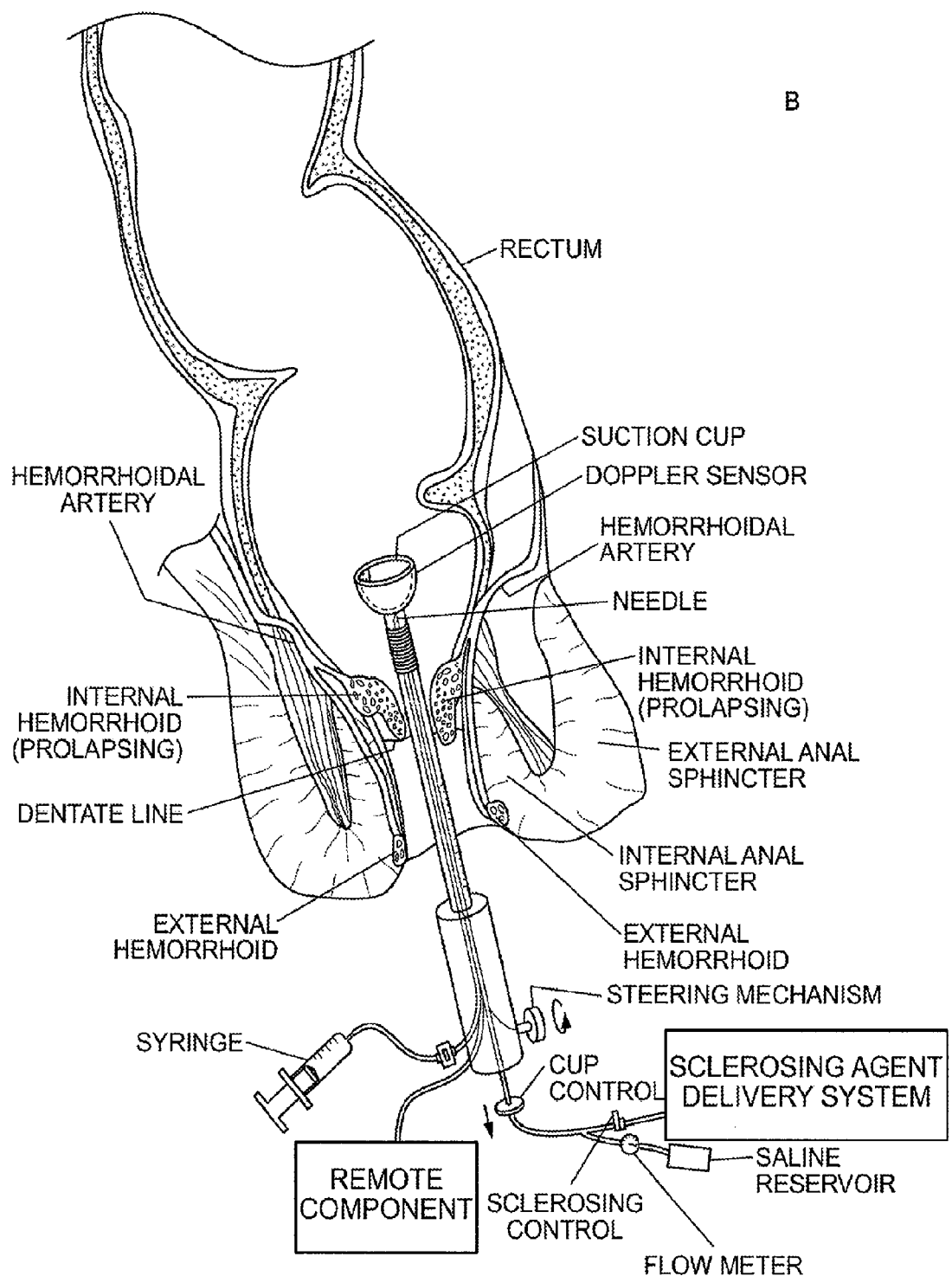
FIG. 19B is a side view of the hemorrhoid treatment device that utilizes steam energy with the suction cup deployed.

FIG. 19B illustrates that the device can be inserted into the patient's rectum to a specified length. The suction cup can be mechanically connected to a cup control, such as a knob. The cup control can then be pulled, as shown by arrow, or otherwise manipulated to open or expand the collapsed or contracted suction cup. The steering mechanism can be manipulated (e.g., rotated—as shown by arrow—pulled, pushed, levered) to angularly articulate or rotate the suction cup.

Figure 19C:
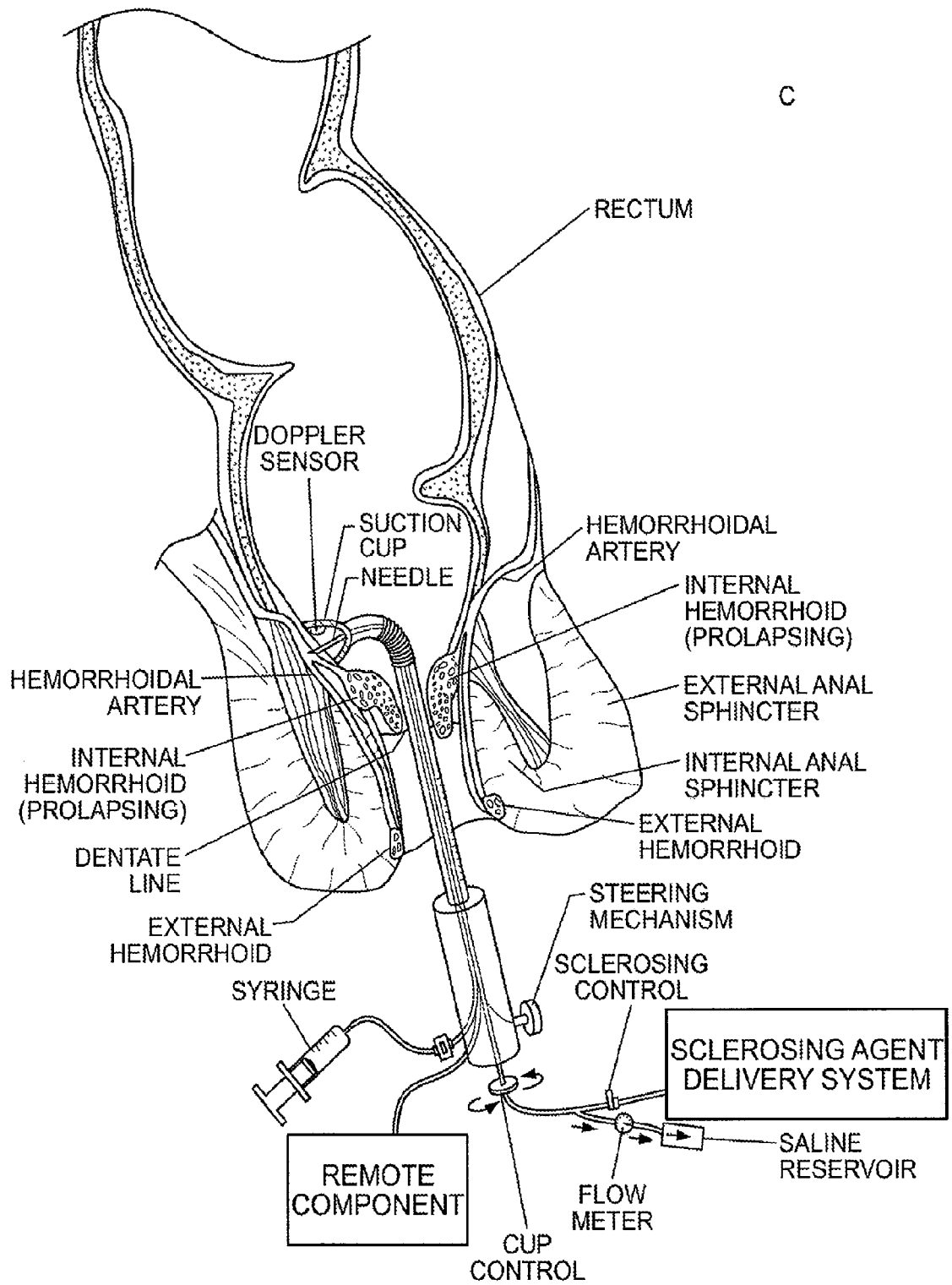
FIG. 19C is side view of the hemorrhoid treatment device utilizing steam energy to ligate superior hemorrhoidal arteries with suction cup providing stabilization during the treatment.

FIG. 19C illustrates that the articulating lever at the proximal end of the device can be turned to actuate the articulating joint at the distal end of the device, thereby directing the suction cup toward the target tissue. The Doppler sensor can be located radially inside the suction cup, and can locate the hemorrhoidal arteries. The wires for the Doppler transducer wires run the length of the interior of the device and exit at the proximal end where they can be connected to a remote component and/or speakers or headphones. Once the distal end of the device is in the correct location, suction is applied to hold it in place against the tissue. Suction is applied through a hole located inside the suction cup connected to anon-collapsible tubing that runs the length of the interior of the device and exits at the proximal end of the device. This tubing is connected to a vacuum source, such as a syringe.

The needle, heretofore being protected from the tissue, can then be slowly advanced into or adjacent to the hemorrhoidal artery by turning or otherwise operating the cup control at the proximal end of the device. The needle can be connected to a lumen, channel or tubing running along the interior of the device throughout the length of the handle and exiting at the proximal end where the tubing can be attached to a flow meter running to a low-pressure saline (or empty) reservoir or bag. The flow meter can regulate the blood flow to the saline reservoir and/or the saline flow from the saline reservoir to the needle. For example the blood flow to the needle can occur only once the needle tip is inside the artery, indicating that the needle is in position to deliver steam and/or sclerosing agent(s) into the artery. The tubing can also be connected to a sclerosing agent delivery system and/or steam generator, which can be turned on once the needle tip is in the artery by a sclerosing control (e.g., a button) located on the tubing. The sclerosing agent or steam can thereby be injected into or adjacent to the artery, optionally in combination with the saline (the flow meter can have a pump), causing thermal damage and collapse.

When the Doppler sensor stops reading arterial flow, the steam can be automatically turned off, for example for safety. The suction can then be removed from the suction cup, releasing the suction cup from the rectal mucosa, and the device can then be rotated around the circumference of the rectum and all hemorrhoidal arteries can be ablated in a similar fashion. When no further arteries are located by the Doppler sensor, the articulating joint can be put back into the original configuration (e.g., coaxially aligned with the handle) and the device can be removed from the rectum.

The device can be made with a multi-lumen polymer extrusion, such that the tubes are wires are contained with the interior of the device and exit individually at the proximal end. The articulating joint can be made from pull wires and pinned links or laser cut extrusions that is connected to the articulating lever. The Doppler is located inside the suction cup so that it can measure arterial flow at the same time as the steam is injected, thereby allowing a feedback mechanism to stop steam injection when flow has ceased. The suction cup can be rotated about the entire circumference of the rectum when suction is relieved.

The device allows for precise ablation of the hemorrhoidal arteries with little to no damage to surrounding structures. The device can avoid or minimize damaging the internal anal sphincter, which causes severe spasm and pain and can lead to fecal incontinence. Similarly, it does not cut or remove any tissue, thereby will lead to significantly less and potentially no post-operative pain.

Figure 19D:
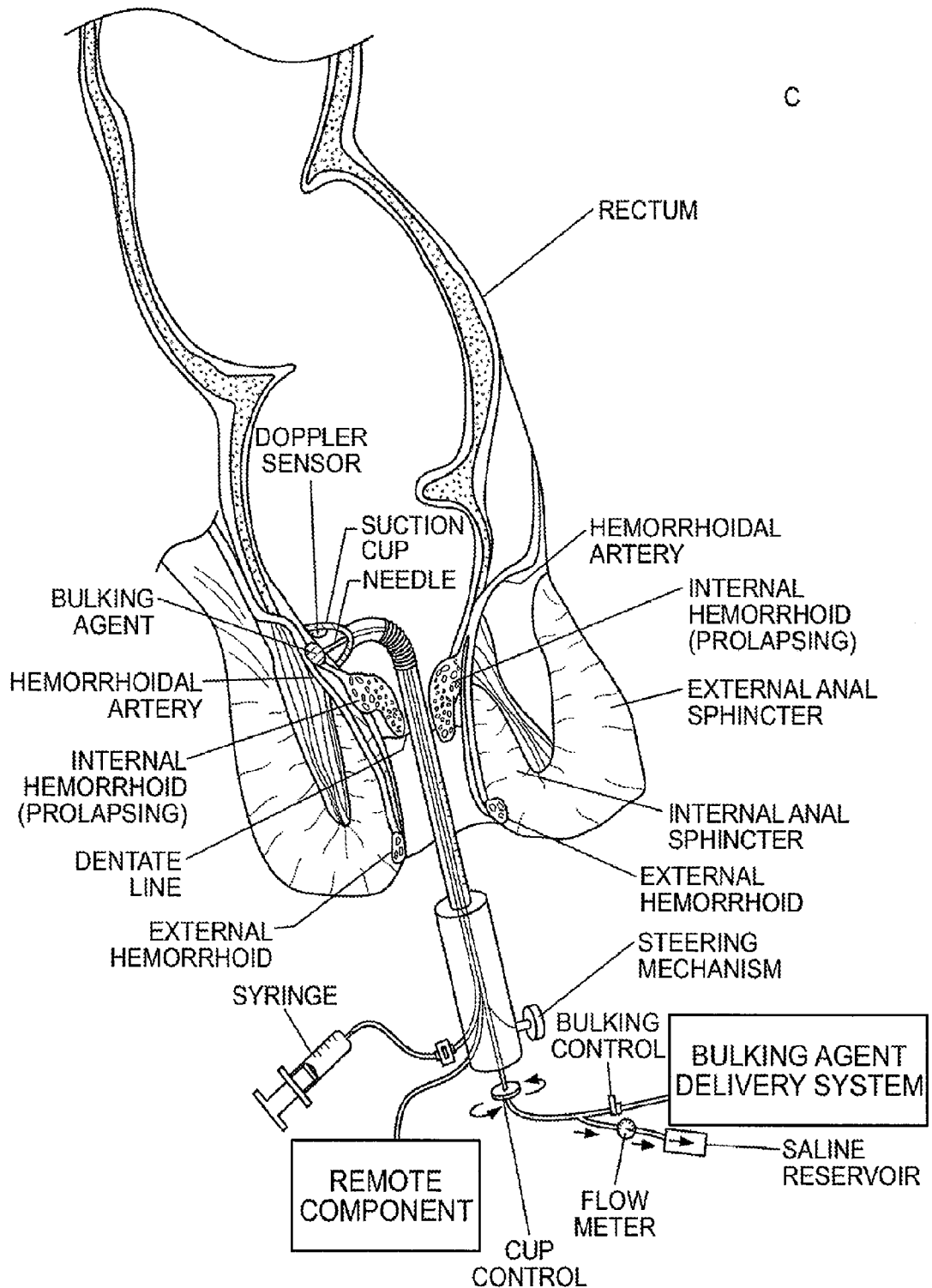
FIG. 19D illustrates a method of using the hemorrhoid treatment device for injecting a bulking agent to tamponade the hemorrhoidal arteries.

FIG. 19D illustrates that a bulking agent can be injected or a bulking device can be implanted adjacent to the hemorrhoidal artery. FIG. 19D illustrates that the device can be configured to tamponade the hemorrhoidal artery by delivering a bulking or tamponading agent below the surface of the mucosal tissue and adjacent to the hemorrhoidal artery. The bulking or tamponading agent can be delivered by the bulking agent delivery system. The flow of bulking agent can be controlled by the bulking control, for example a valve. The bulking agent can be a bolus of hardening or otherwise curing polymer or other material or device described herein. The bulking agent can be exposed to curing energy (e.g., IR energy) after being injected or implanted. The bulking agent can compress or tamponade the hemorrhoidal artery.

Figure 20:
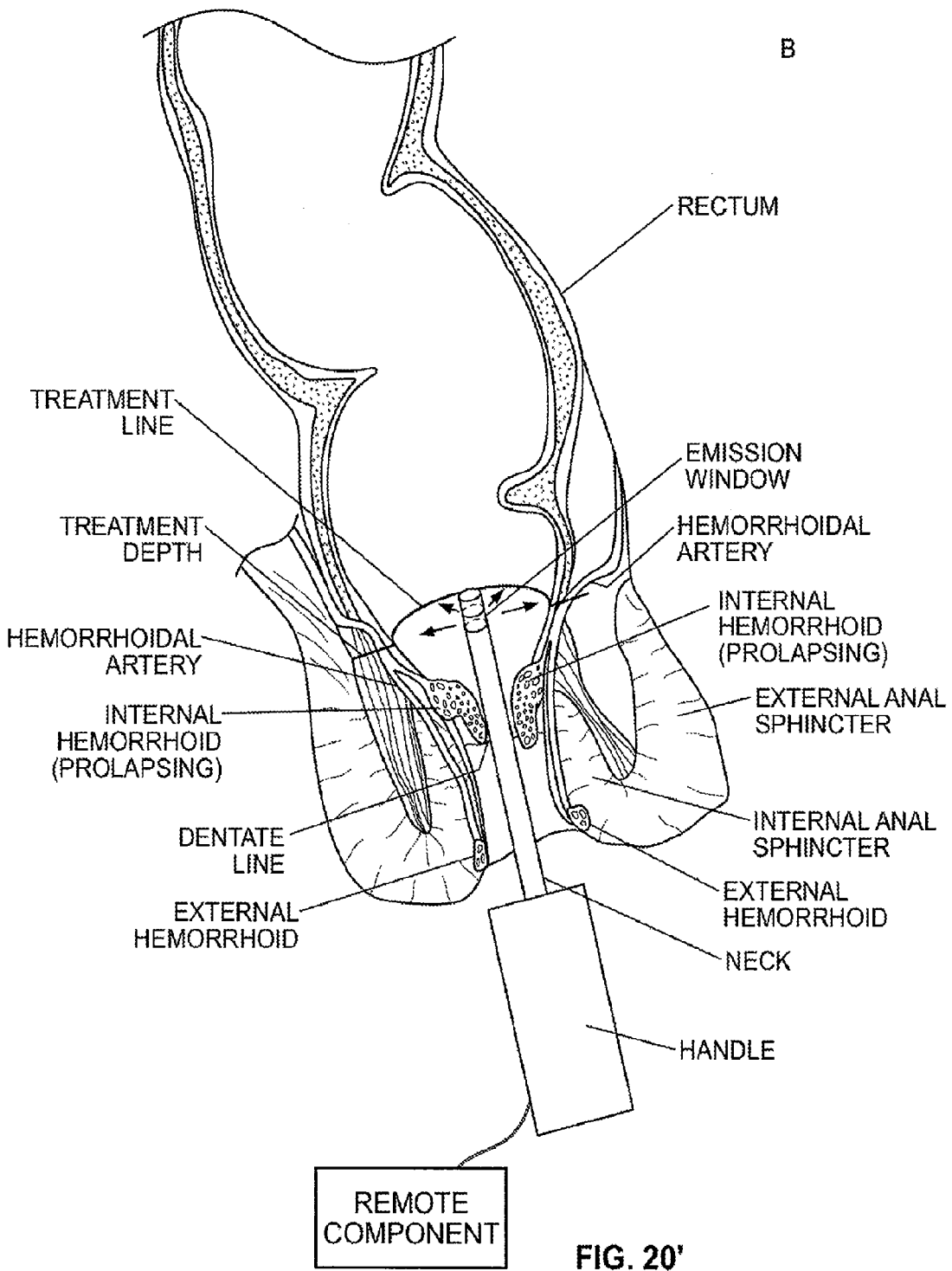
FIG. 20' illustrates a variation of the hemorrhoid treatment device emitting infrared radiation in a circular pattern in the rectum.

FIG. 20' illustrates that the distal end of the device can have an emission window. The emission window can located around part or all of the lateral surface of the device. For example, the emission window can be located around part of or the entire circumference of the device. The device can have an infrared radiation transducer inside of the emissions window.

When the emissions window is orad to the dentate line, the infrared transducer can emit infrared (IR) energy in some or all (e.g., 360°) angles, as shown by arrows, out from the emissions window. For example, IR energy can be emitted in a circular plane perpendicular to the longitudinal axis of the neck at the emissions window.

The IR energy can be received treat a treatment line around part or all of the perimeter or circumference of the mucosal tissue surface of the rectum at the level of the emission window. The IR energy can transmit into the tissue underlying the mucosal tissue surface. The IR energy can reach a treatment depth, for example deep enough to transmit energy to some or all of the hemorrhoidal arteries.

The IR energy can induce blood clotting and/or ablation of vessels. The IR energy can cause substantially concurrent ligation of all the hemorrhoidal arteries in the rectum with a single, uninterrupted delivery of energy. The energy delivered can be IR energy, RF energy, HIFU energy, thermal energy, electro-cautery energy (i.e., plasma), or combinations thereof. The energy can be delivered from the basket, balloon, or any other variation shown herein.

The device can have a stopper on the neck and/or handle. The stopped can prevent the terminal distal end of the device from advancing more than about 8 cm into the rectum. The stopper can have a radius configured to abut the outside of the anus. The length from the stopper to the emission window can be from about 4 cm to about 6 cm.

FIGS. 20A through 24B illustrate achieving TOH using tools and methods described herein.

Figure 20A:
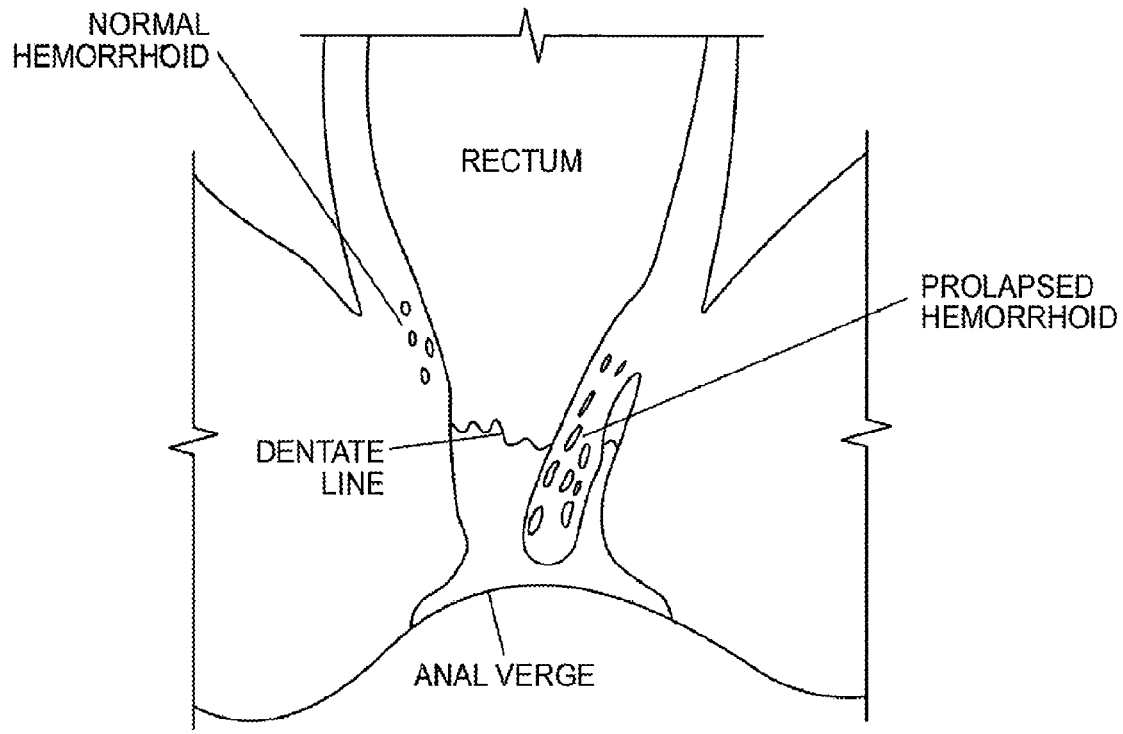
FIGS. 20A and 20B illustrate a prolapsed hemorrhoid and a pexied hemorrhoid, respectively.
Figure 20B:
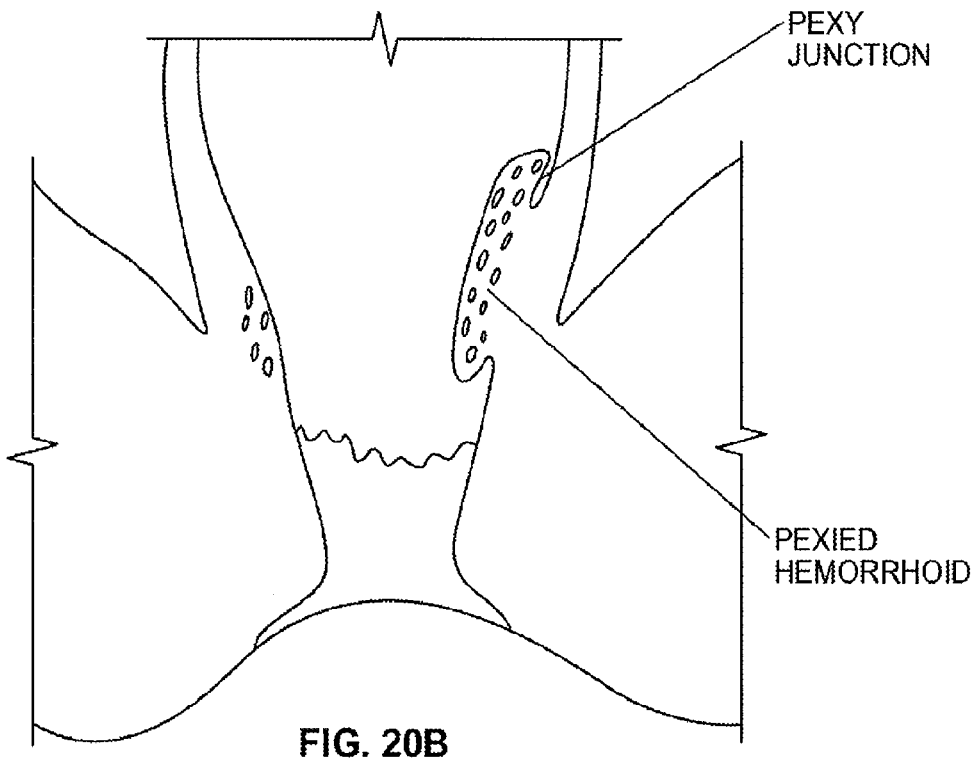

FIG. 20A shows typical normal hemorrhoids and prolapsed hemorrhoids. The device can pexy (i.e., lift and secure) the hemorrhoids so that the hemorrhoids are higher in the anorectal canal and no longer prolapsed, as shown in FIG. 20B. The pexied hemorrhoid can be less obstructive of the rectum and reduce symptoms. The pexied hemorrhoid can be attached to the rectal wall at a pexy junction. The device can pexy with any of the devices described herein, either those with a wand or those on the end of a flexible endoscope.

Figures 21A, 21B, 22A, 22B:
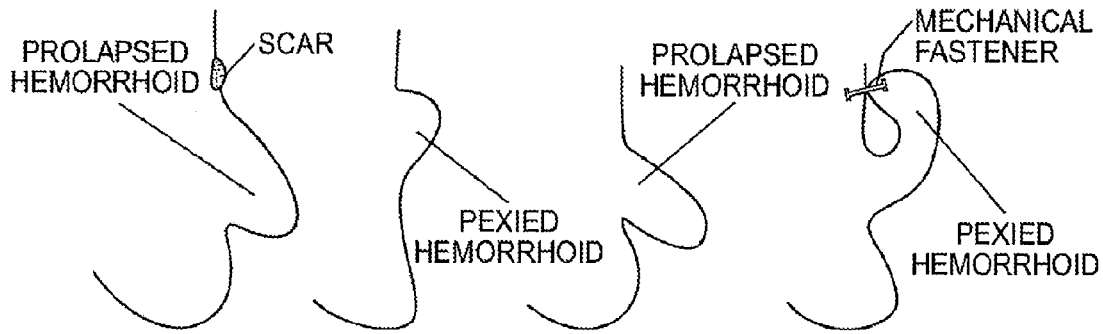
FIGS. 21A and 21B illustrate a variation of a method of hemorrhoid treatment by pexying by scarring.
FIGS. 22A and 22B illustrate a variation of a method of hemorrhoid treatment by pexying with a mechanical fastener.

FIG. 21A illustrates that the device can be used to create a scar in the anorectal canal proximal to (above) the hemorrhoid. The tissue of the scar can shrink, pulling up the hemorrhoid, as shown in FIG. 21B. The scar can be created with ablation, such as with RF energy, rubberbanding the mucosa, injecting sclerosant, cryo (cold), or other energy sources. The size of the scar can correlate to the size of the prolapsed.

FIG. 22A illustrates a prolapsed hemorrhoid. FIG. 22B illustrates that a mechanical fastener can be used to attach the hemorrhoid to the proximal inner diameter of the anorectal canal. The mechanical fasteners could include clips, tacks, brads, and staples, suturing devices, or combinations thereof.

Figures 23A, 23B, 24A, 24B:
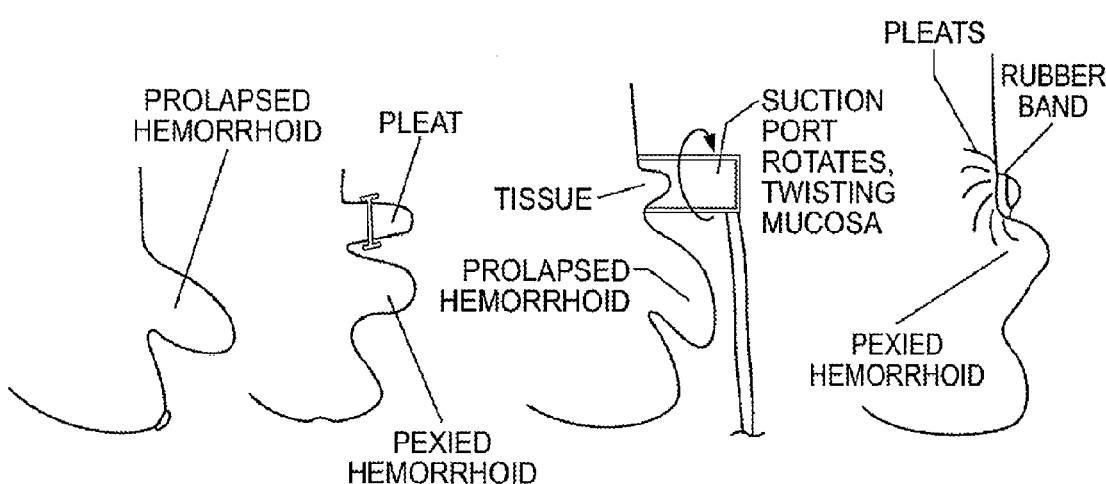
FIGS. 23A and 23B illustrate a variation of a method of hemorrhoid treatment by pexying with a pleat.
FIGS. 24A and 24B illustrate a variation of a method of hemorrhoid treatment by pexying with a pleat.
Figures 24A, 24B:
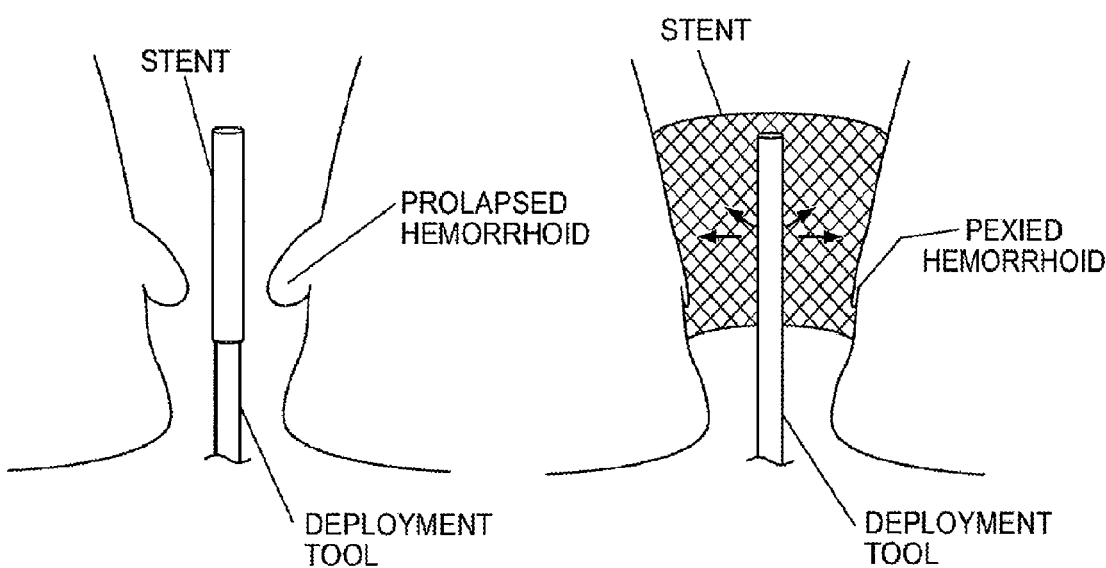

FIG. 23A illustrates a prolapsed hemorrhoid. FIG. 23B illustrates that a tissue fold or pleat above the hemorrhoid can be formed to pull the hemorrhoid up, as shown in FIG. 22B. This tissue fold could be created using the clip applier, stapler, or any mechanical coupling elements described herein or combinations thereof.

FIG. 24A illustrates that the mucosa tissue above the hemorrhoid can be twisted. The tissue can be sucked into a suction port. The suction port can then rotate about the longitudinal axis through the middle of the opening of the suction port. FIG. 24B illustrates that a rubber band can be placed over the twisted mucosa to hold it in place. The twisted tissue can form pleats. A scar will form that can hold the twisted mucosa in place over the long term. Other clips herein can be used in addition to or in lieu of the rubber band.

FIG. 24A' illustrates that an expandable stent can be mounted on a deployment tool, such as a catheter. The stent can be a wireframe or mesh scaffold. The stent can be self-expandable (i.e., elastically biased to in an expanded configuration, but restrained in a contracted configuration on the deployment tool), and restrained by a sheath on the deployment tool. The stent can be balloon-expandable (i.e., plastically deformable from a contracted configuration to an expanded configuration) and mounted on a balloon in the deployment tool. The stent can be inserted into the rectum adjacent to the prolapsed hemorrhoid.

FIG. 24B' illustrates that the stent can be radially expanded in the rectum. The stent can be radially expanded, as shown by arrows, for example by removing a restraining sheath over the stent and/or inflating a balloon onto which the stent is mounted. The expanded stent can compress the hemorrhoids radially outward. All of the pexied hemorrhoids around the circumference of the rectum can be concurrently pexied by a single stent.

Figures 25A, 25B, 25C:
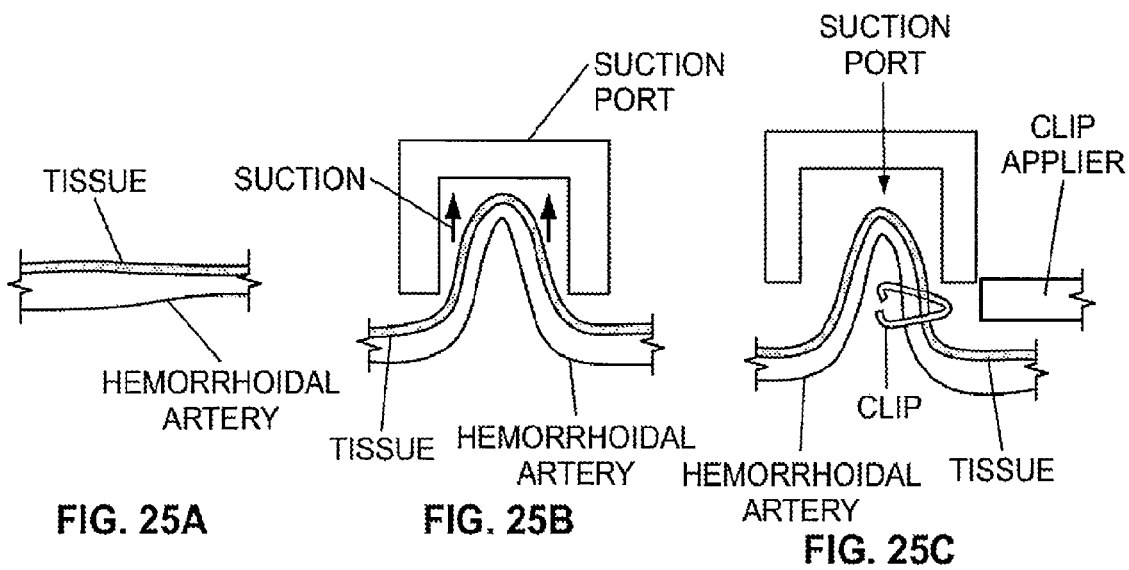
FIGS. 25A through 25C illustrate a variation of a method for using a clip.
Figures 25A, 25B:
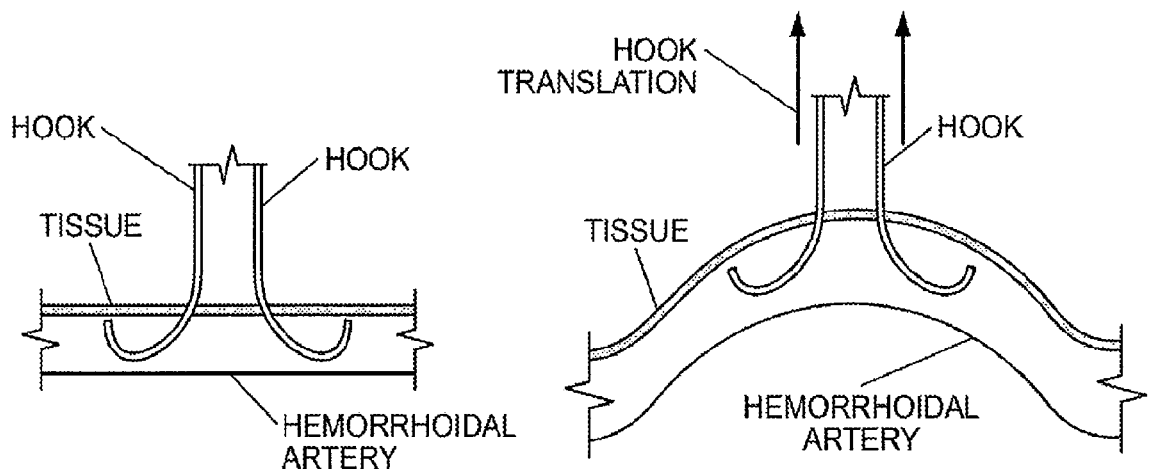

FIG. 25A illustrates the surface of the mucosal tissue covering a hemorrhoidal artery. FIG. 25B illustrates that the suction port can apply suction to draw up and hold the mucosal tissue in place, forming a tissue mound. FIG. 25C illustrates that the clip applier can then apply a clip to the resulting tissue mound, thereby clamping off the hemorrhoidal artery that runs through the tissue mound. The clip does not go completely across the mucosa, since clipping across the full diameter of the tissue mound would cause the mound to necrose. The clip can be applied such that the long axis of the clip is perpendicular to the long-axis of the tissue mound. However, the clip can also be applied at any angle with respect to the long-axis of the tissue mound; for example, the clip can be applied parallel to the tissue mound's long-axis, and at the tissue-mound's peak.

Figure 25:
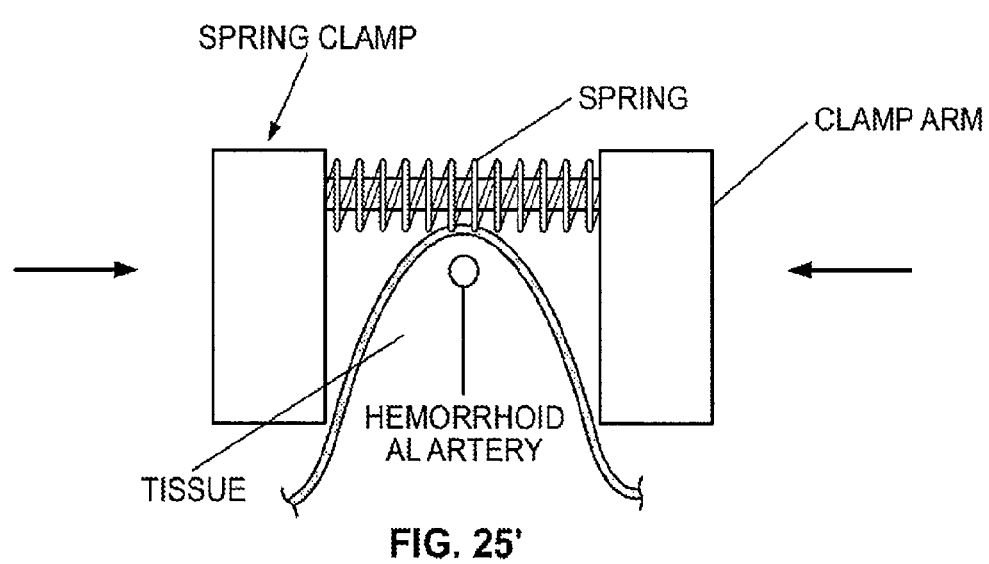
FIG. 25' illustrates a method of placing a spring clamp across a tissue mound.

FIG. 25A' illustrates that one, two or more hooks can be attached to the mucosal tissue. FIG. 25B' illustrates that the hooks can be translated away from the surface of the mucosal tissue, raising the tissue and the hemorrhoidal artery in a tissue mound. A clip can then be applied partially or completely across the tissue mound as shown in FIG. 25C. FIG. 25' illustrates that a spring clamp can be placed across the tissue. The spring clamp can have opposing clamp arm and a spring connected to both clamp arms. The spring clamp can be extended and placed on the tissue. The spring can then contract and compress the tissue, as shown by arrows. A clip can then be applied to the tissue mound as shown in FIG. 25C.

Figure 26A:
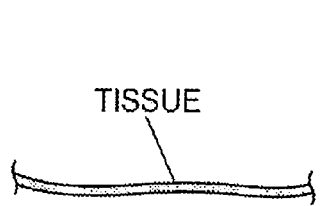
FIGS. 26A through 26E illustrate a variation of a method for using a clip.
Figure 26B:
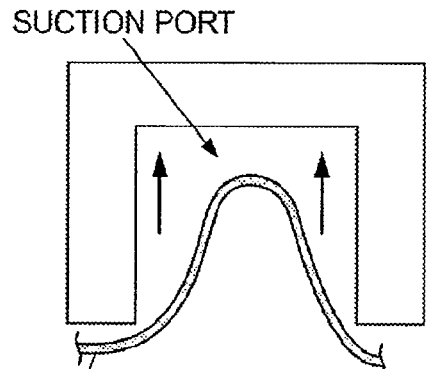
Figure 26C:
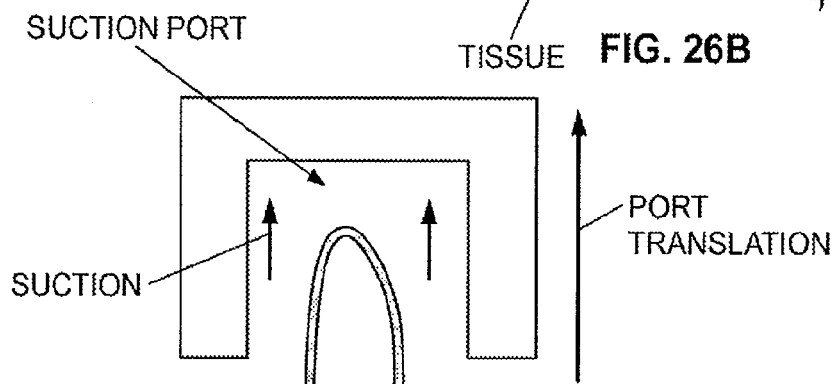
Figure 26D:
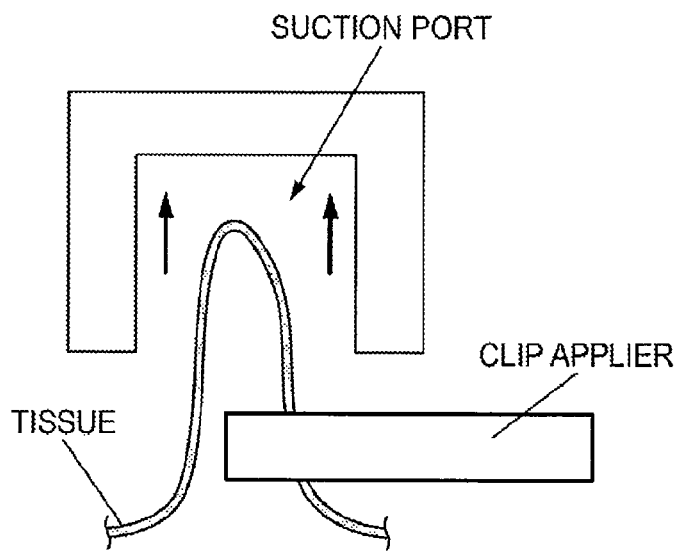
Figure 26E:
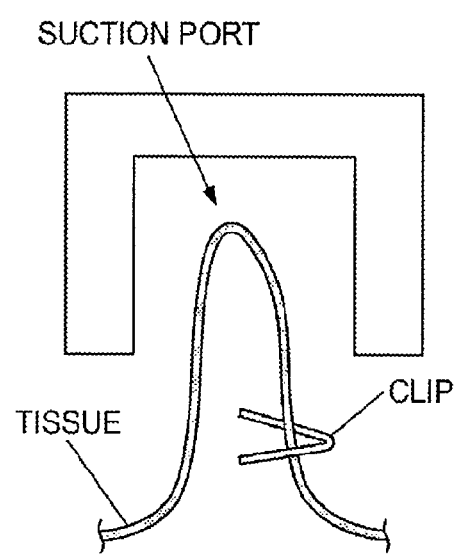

FIG. 26A illustrates that the mucosal surface can be substantially flat before the suction port applies a vacuum or suction. FIGS. 26A through 26E illustrate a similar device to the device shown in FIGS. 25B and 25C, but the device in FIGS. 26B through 26E demonstrates that after the suction port grabs hold of the mucosa by the application of suction, as shown by arrows, the suction port can be translated, as shown by arrow, and elevated away from the mucosal surface, in order to lengthen the exposed neck of the tissue mound, and provide room for the clip applier to apply a clip across the exposed neck of the tissue mound (the hemorrhoidal artery is not shown). The clip can compress and ligate the hemorrhoidal artery.

FIG. 28 illustrates that a clip can pierce the mucosal tissue and surround the hemorrhoidal artery. The clip can be compressed (going from an "open" U-shape to a "closed" I-shape), thus compressing and collapsing the artery.

The clip can pierce the mucosa in a variety of ways. For example, the clip can be inside a jaw that is sharp and pierces the mucosa. The clip tips can be sharp, and exposed beyond the jaws. This clipping mechanism can be combined with any of a variety of mechanisms for holding the mucosa in place, such as vacuum suction, hooks, chemical adhesive, or combinations thereof.

FIG. 29A illustrates a C-shaped staple that pierces the mucosa so that it surrounds the hemorrhoidal artery, and is then further compressed to form an O-shape, thus compressing and collapsing the artery. There can be an anvil at the end of the stapler (shown as two prongs receding up from the image that hold the staple base in place). In order to over-drive the staple into the smallest O-shape possible, a second pliers-like mechanism can be used. FIG. 29B illustrates the staple deployed around an artery.

The ligation mechanism could be, for example, a clip, staple, automatic suture, band, energy delivery, radiation delivery, sclerosant, tamponading agent, embolizing agent, and/or drug(s). Additional features could include a fixation component (e.g. mucosal fixation), method to navigate around the bulk of the tissue (e.g. hemorrhoid), method to lift the tissue (e.g. hemorrhoid), the use of bio-absorbable materials, features to reduce pain, features to prevent prolapse (e.g. primary or recurrent prolapse), and other methods to block flow (e.g. blood flow) through a vessel. Additionally, various medical applications for this device are described.

For example, mechanical ligation devices can include clips. Clips for ligating vessels cause compression of the vessel and terminate flow through the vessel where the clip is applied. Clips for this purpose can come is various forms, such as: clips with two or more prongs, clips with sharp tips so that they pierce tissue and then clamp (for example a clip that pierces the tissue, clamps around a vessel, and is buried under the tissue), clips that clamp externally around a mound of tissue and thereby clamp underlying vessels, clips that approach the vessel parallel (0 degrees) to the long axis of the vessel (or tissue) or clips that approach the vessel perpendicular (90 degrees) to the vessel. The clip could approach and/or ligate the vessel at any orientation (0-90 degrees) with respect to the long axis of the vessel and still occlude flow. Clips could have different length prongs. The clips could have barbs on the prongs. The clips could have teeth on the prongs, for example, alligator teeth prongs (show figure). The clips could be made wholly or partially of bio-absorbable (resorbable) materials, such as described below. The clips could be made such that they are biased closed and held open until deployment (e.g. Nitinol clips). The clips could be compressed to close around the vessel (or tissue). The clips could start in different shapes, such as V-shaped clips, W-shaped clips, etc. The clips could be combined with other mechanisms included here, such as clips to localize radiation, sclerosing agents, drug delivery, energy delivery, or to pexy (i.e. lift) tissue.

The clips could be introduced through a flexible or rigid endoscope. Examples of clips that are introduced through endoscopes include, the InScope™ Multi-Clip Applier (IN-SCOPE, A Division of Ethicon Endo-Surgery, Inc.), the Resolution™ Hemostasis Clipping Device (Boston Scientific Corporation), the Endoscopic Multi-Fire Clip Applier (Syntheon, LLC), the Rotatable Clip Fixing Device HX-5/6-1 (Olympus Optical Co., Ltd.), the Long Clip HX-600-090L (Olympus Medical Systems Corporation), the QuickClip2, HX-201LR-135 & HX-201UR-135 (Olympus Medical Systems Corporation), the QuickClip2 Long, HX-201LR-135L & HX-201UR-135L (Olympus Medical Systems Corporation), the TriClip Endoscopic Clipping Device (Wilson-Cook Medical Inc., Winston-Salem, N.C.), however, these clips are inadequate for intended purpose as they typically require numerous clips to adequately occlude a vessel.

The clips could include any combination of the above variations, for example a clip that is biased open (e.g. using Nitinol) that has a bio-absorbable housing around the prongs that have alligator teeth. This could, for example, allow the clip to fall out of the tissue as the bio-absorbable housings dissolve in the tissue.

Mechanical ligation devices can include staples. Staples for ligating vessels cause compression of the vessel and terminate flow through the vessel where the staple is applied. Staples for this purpose can come in various forms, such as: staplers with or without an anvil, staples that over close (i.e. over compress tissue), staples with barbs, staples that pierce the tissue (e.g. staples that pierce the tissue, clamp around a vessel, and are buried under the tissue), staples at that wholly or partially made from bio-absorbable (resorbable) materials (for example bio-absorbable prongs, or more specifically, bio-absorbable prongs that pierce the tissue), staples that have different length prongs, staples that have teeth (e.g. teeth on the prongs, e.g. alligator teeth), staples that are bias closed (e.g. Nitinol), staples that pexy (i.e. lift up) tissue (e.g. to perform a mucopexy or hemorrhoidopexy), staples that localize other therapies (e.g. radiation, sclerosing agents, drug delivery, or energy delivery). There could be one or more staples deployed at a time such as, one or more rows of staples, such as anastomosis staplers (e.g. bowel anastomosis staplers, vascular anastomosis staplers, or airway anastomosis staplers), or staplers for the PPH procedure (procedure for prolapsed hemorrhoids), closure staplers (for example bowel closure staplers or vascular closure staplers), or staplers to close tissue (e.g. skin). The staples could start in different shapes, such as C-shaped staples, D-shaped staples, M-shaped staples, W-shaped staples, etc.

The staples could include any combination of the above variations, for example a staple that is biased open (e.g. using Nitinol) that has a bio-absorbable housing around the prongs that have alligator teeth. This could, for example, allow the staple to fall out of the tissue as the bio-absorbable housings dissolve in the tissue.

The vessels (e.g. hemorrhoidal arteries) can be sealed by automatically placing sutures to ligate the vessels (e.g. arteries). Automatic suturing ligation can include the placement of sutures, suture-like materials around and/or near the vessel (e.g. hemorrhoidal artery) in order to compress the vessel (e.g. artery), and the placement of the suture or mechanical ligation device is automated in that it does not require all the steps of hand-suturing tissue as usually performed by a physician. For example, the device could have at its working end a miniature sewing machine, that with the press of a button places one or more loops of suture through the tissue (e.g. mucosa) and around the vessel (e.g. hemorrhoidal arteries), thereby squeezing shut the vessels (e.g. arteries). Automatic suturing ligation devices could include components that pass the suture through the tissue, devices that tie or bring together or seal the ends of the suture, and devices that both pass suture through tissue and bring together the ends of the suture.

There are various components and methods by which one can pass the suture through the tissue (e.g. mucosa) and around the vessel (e.g. hemorrhoidal arteries). For example, the device can pass a needle beneath a mound of tissue containing the vessel (e.g. hemorrhoidal artery).

Figure 30A:
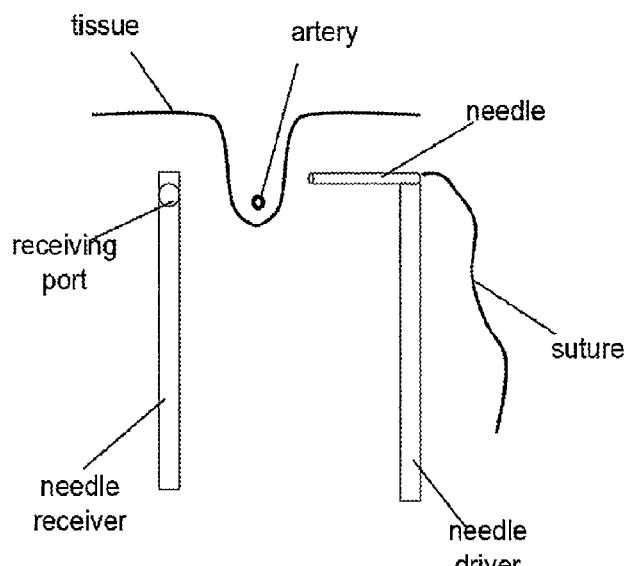

FIG. 30A shows the mound of tissue surrounded by the two arms of the device. One arm is the needle driver holding the needle that enters the tissue roughly perpendicular to the long axis of the mound of tissue. The needle is attached to a suture at the end opposite its tissue-piercing end. The other device arm is the needle receiver which can grab the needle once the needle emerges from the other side of the tissue mound.

Figure 30B:
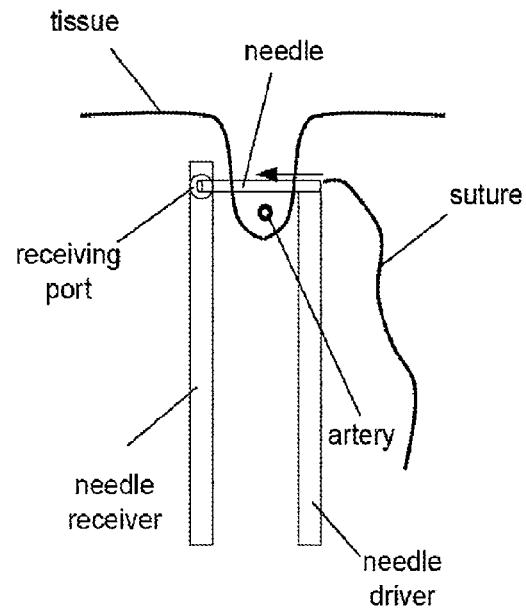
Figure 30C:
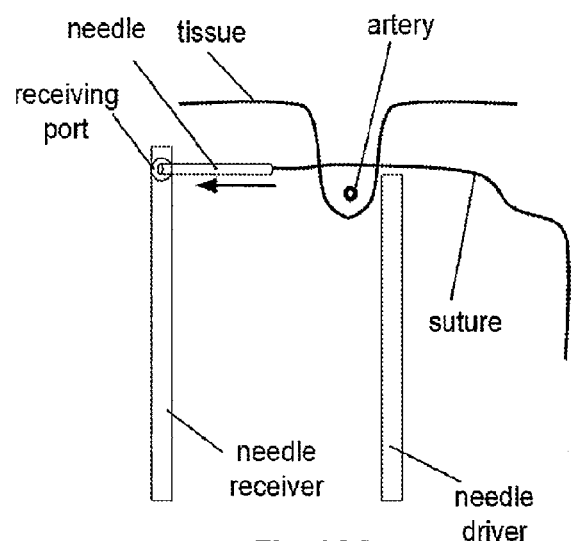
Figure 30D:
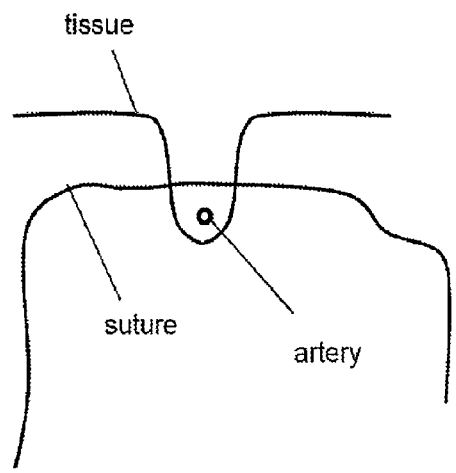

FIG. 30B shows the needle driver moving towards the tissue mound so that the needle punctures the tissue mound, and engages the needle receiver on the opposite side of the mound. The needle receiver holds onto the end (or near the end) of the needle, while the needle driver disengages the needle (lets it go). The two arms, especially the needle receiver, are then withdrawn away from the tissue mound, as shown in FIG. 30C. The suture then lies deep to the artery, with its free ends hanging out well above the mucosal surface as shown in FIG. 30D. The free ends of the suture can then be crossed over each other, tied, and thus apply pressure to compress the artery, sealing off its blood flow and ligating the artery.

The devices shown in FIG. 31A through 31D can have several variations. The needle can be straight or curved. The suture can have barbs on it. The needle driver and needle receiver arms can hold and release the needle using a variety of mechanisms: forceps, tweezers, clamps, magnets, adhesives, or combinations thereof. The free ends of the suture can be re-passed through the tissue multiple times, crossed over multiple times, and tied together or locked together using any of the mechanisms described below.

The suturing device shown in FIG. 31A can place sutures to form what surgeons call a "figure-of-eight" stitch. The device has two arms that are joined at their proximal ends by a flexible joint. On the distal ends of each arm can be a needle containing suture (diagrammed as a shaft with a cone on it), and a receiving port to grab the needle.

The needle is shown in FIG. 31B: The needle is similar in mechanism to a harpoon. The tip of the needle is a cone, with the base of the cone attached to a suture. The suture runs through a hollow cylindrical shaft that is joined to the cone such that the cone can disengage the shaft at a time determined by the device and/or operator.

Figure 31E:
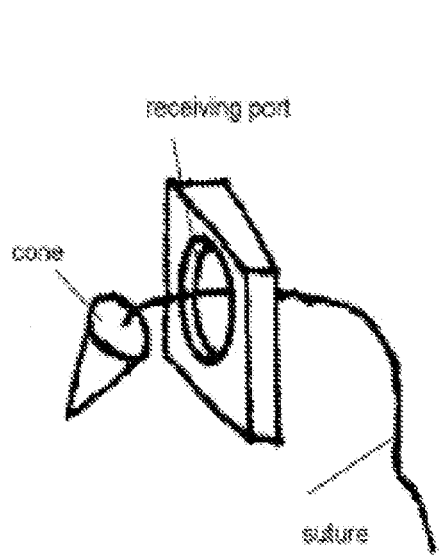

FIG. 31C shows the needle moving towards the receiving port. In FIG. 31D, the needle has passed through the receiving port. At this stage, the cone of the needle becomes disengaged from the hollow cylindrical shaft. The cylindrical shaft can be withdrawn over the suture that is attached to the cone. Then, as shown in FIG. 31E, the cone of the needle is now on the opposite side of the receiving port.

Figure 31F:
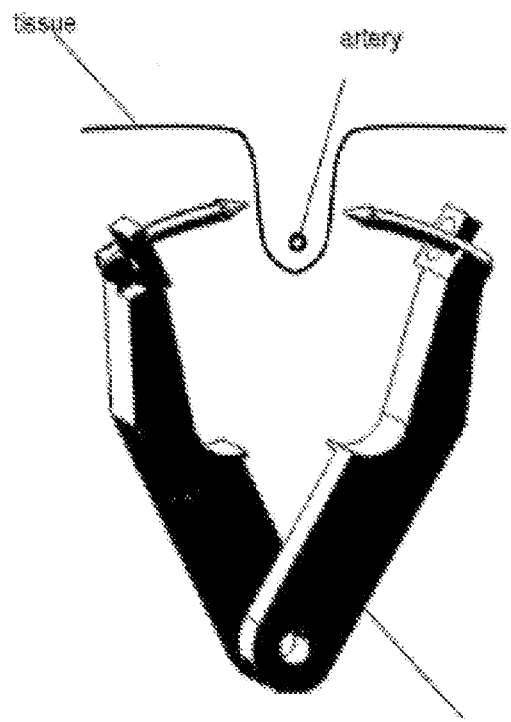
Figure 31G:
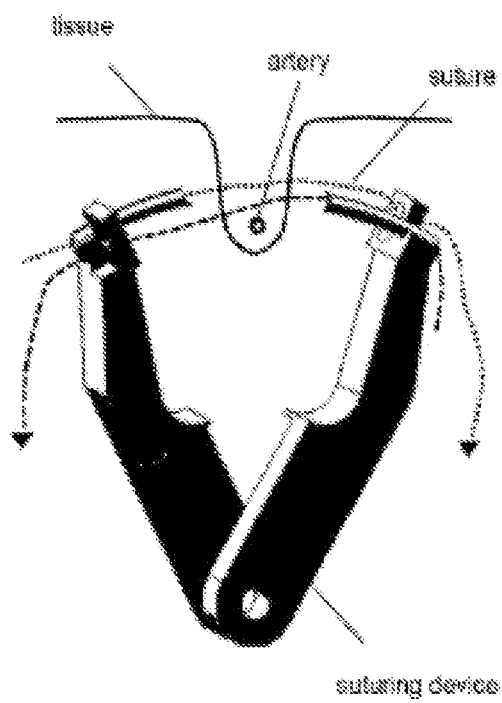

FIG. 31F illustrates that during the treatment procedure (e.g. hemorrhoids treatment procedure), a mound of tissue containing the vessel (e.g. hemorrhoidal artery) is placed between the distal ends of the two arms. The flexible joint at the proximal end of the two arms is narrowed, bringing together the two distal ends (squeezing the device shut). This squeezing causes the needles to pass through the tissue, deep to the vessel (e.g. artery).

Figure 31H:
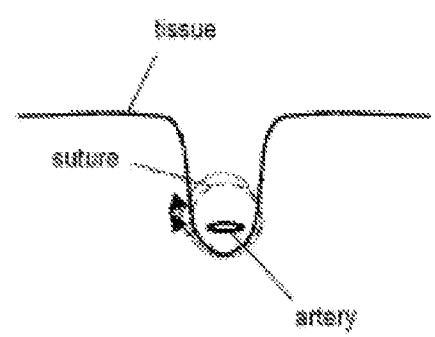

After the cones emerge from the other side of a tissue mound, the cones enter the receiving ports, and disengage, as shown in FIGS. 31B through 31E. This leaves two sutures having passed through the tissue. If the two coned ends are now joined (through a lock-and-key mechanism, hand tied, etc), this leaves a single continuous line of suture that has been passed deep to the artery, in a pattern that surgeons call a "figure-of-eight stitch." The free ends of the suture (hanging out the back ends of each shaft) can then be tied together, completing a figure-of-eight stitch, as shown in FIG. 31H. The sutures can emerge from openings in the side of each receiving port.

Other methods of tying the ends of the suture can be used; such as tying the cone ends to the free ends first. There are also numerous methods by which the cone of the needle can become disengaged from the needle shaft, such as forceps-like grabber that grabs the needle tip, a magnet, etc.

The device shown in FIG. 32A uses a helical needle (e.g., corkscrew-shaped needle) to drive a helical line of sutures around an artery. One end (e.g., distal end) of the helical needle is the tissue-piercing end. The opposite end (e.g., proximal end) of the helical needle is attached to a suture, which runs through a hollow cylindrical shaft called the needle driver. The needle is attached to the hollow cylindrical shaft in a manner that allows the needle to become disengaged at the desired time. The helical needle is placed next to the mucosal surface, and is rotated on its long axis so that it drives a helical path through the tissue, as shown in FIG. 32B.

The helical needle can be positioned so that the hemorrhoidal artery runs through the helix's lumen. The tissue-piercing end of the needle can then be grabbed by a needle receiver arm, while the needle driver becomes disengaged from the helical needle, as shown in FIG. 32C.

The needle receiver arm rotates the needle out of the tissue, leaving two free ends of suture on either side of a segment of suture that makes a helical path through the tissue, as shown in FIG. 32D.

FIG. 32E illustrates that the suture could be attached to the needle near the distal tip (i.e., the tissue-piercing end) of the needle. The receiving arm can engage the suture, and the needle driver can reverse the direction of rotation to withdraw the needle before the entire needle exits the tissue. Additionally, the suture could be attached to needle through mechanisms that do not involve a hollow cylindrical shaft with the suture running through it; for example, the suture could run next to the cylindrical shaft.

Once the suture is pulled through the path, the two free ends of the suture can be tightened and tied, compressing and ligating the artery.

There are various components that can tie or bring together or seal the free ends of the suture. For example, the suture free ends could be hand-tied. The free ends of the suture could be tied to small weights or hooks so that it would be easy for the device or operator to grab them.

The suture free ends could be tied via a zip-tie mechanism. FIG. 33A shows an example of a zip-tie device. The suture has been passed through the mound of tissue so that it is deep to the vessel (e.g. hemorrhoidal artery). The free end of the suture is then passed through the eyelet of the zip-tie, as shown in FIG. 33B. This can form a lasso. The zip-tie eyelet is designed such that the free end of the suture can move through the eyelet in only one direction. Therefore, once the free end is passed through the eyelet, pulling on the free end of the suture tightens the lasso loop, and pressure within the lasso loop is unable to cause the free end to move the other direction within the eyelet. Thus, once the free end is passed through the eyelet, pulling on the free end tightens the lasso loop in a manner that does not allow the lasso loop to be loosened. A variety of embodiments can accomplish this one-way locking zip-tie mechanism: For example, similar to plastic zip-ties for commercial goods, the free end of the suture can have barbs on it, and the eyelet can have a ratchet that only allows the barbs to move in one direction through the eyelet. Alternatively, the suture can have no barbs but the zip-tie eyelet can be selectively tightened around the suture which passes through it, such that once the lasso is tightened to a sufficient level, the zip-tie eyelet can be tightened so that the suture cannot move through it anymore.

Figure 34A:
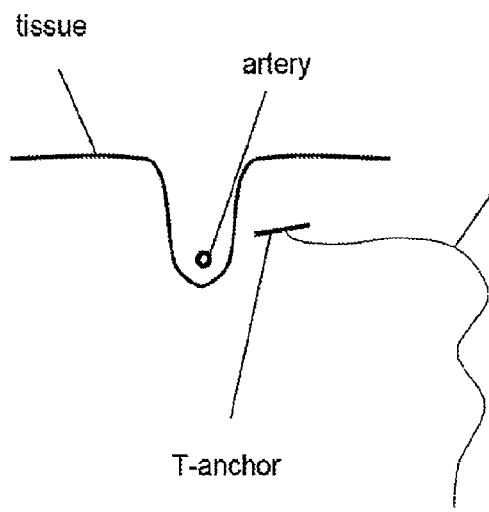
Figure 34B:
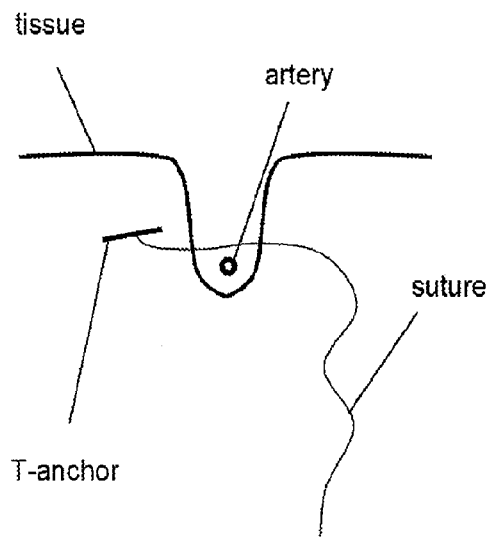
Figure 34C:
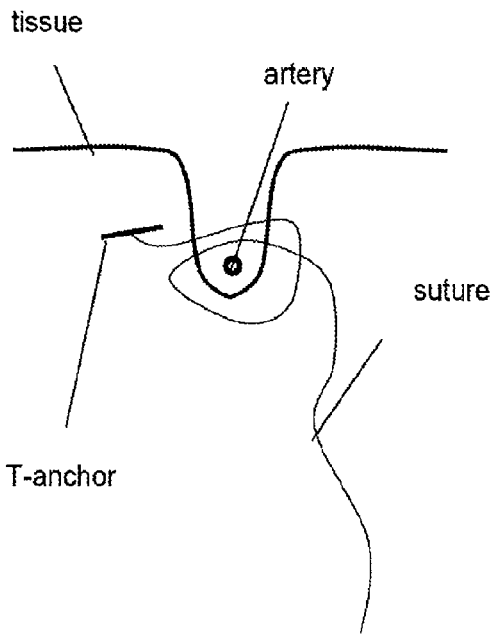
Figure 34D:
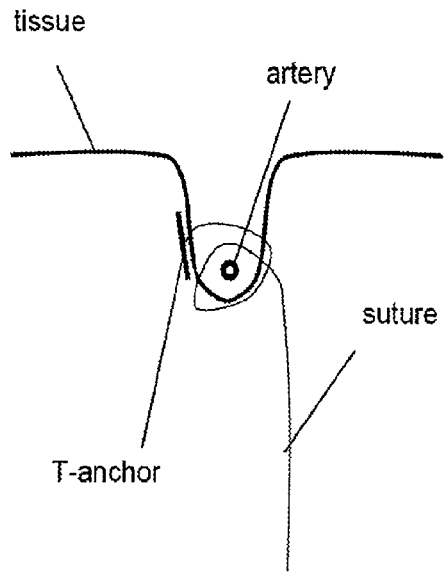
Figure 34E:
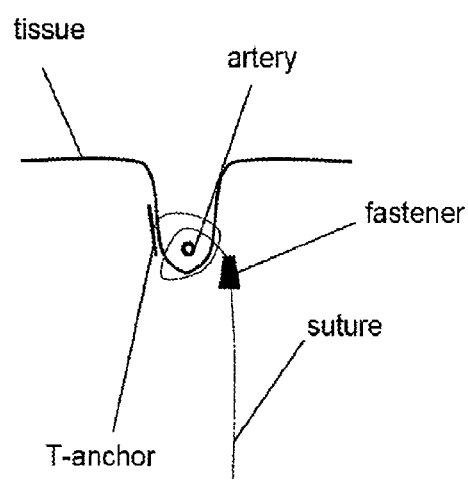

At least one end of the suture can be a T-anchor integrated with the suture or pledget slidably attached to the suture. The T-anchor functions similarly to T-anchors on plastic clothing tags. For our treatment device (e.g. hemorrhoids treatment device), the T-anchor can be a bar that has a suture attached near the middle of the bar. One or both ends of the T-anchor can be sharp so that the T-anchor can pierce through tissue if the sharp tip is presented so that the bar is perpendicular to the mucosal surface. FIG. 34A shows the T-anchor positioned next to a mound of tissue with the vessel (e.g. hemorrhoidal artery) running through the tissue mound. The T-anchor is pushed through the mound of tissue so that the T-anchor emerges on the opposite side of the tissue mound, as shown in FIG. 34B. This can ensure that the suture runs deep to the vessel (e.g. artery). The suture can then be looped around the tissue mound and passed through the tissue again so that the suture forms a loop around the vessel (e.g. artery), as shown in FIG. 34C. The T-anchor can then change its angle with respect to the suture, as shown in FIG. 34D. The T-anchor can then lie with its flat side parallel to the tissue (e.g. mucosal surface). When the suture is tightened, the T-anchor is pressed more firmly against the tissue (e.g. mucosal surface). Then a sliding fastener/clamp can be applied to the free end of suture, as shown in FIG. 34E. This fastener can be pushed along the free end of suture until it fits tightly against the tissue (e.g. mucosal surface), thus tightening the suture loop, and preventing the suture loop from loosening. The sliding fastener/clamp can then be locked in place onto the suture position on which it resides. The T-anchor can have several variations. For example, the T-anchor's bar could be a disc, or could be attached to the suture after looping the suture around the vessel (e.g. artery).

The suture free ends can be sealed together with a twist-tie mechanism. The suture free ends can be sealed together by heating them until they become sealed (e.g. melting the ends together). The suture free ends can be sealed together with a lock-and-key mechanism. This can take various forms, such as that similar to a snap on a coat, the sealing part of a Ziploc plastic bag, or combinations thereof.

The suture used in the automatic suturing ligation devices can have barbs (similar to Quill SRS by Angiotech Pharmaceuticals) that only allow it to be passed through tissue in one direction, can excrete or be coated with an adhesive, so that it can hold tightly within the tissue it passes through, can be absorbent of water, such that the suture diameter expands in tissue, with the resulting increased pressure holding the suture within the tissue, or combinations thereof.

Additionally other mechanical mechanisms to occlude flow through a vessel, include, but are not limited to, a tight-fitting band (e.g. rubberband) that squeezes the tissue captured inside it sufficiently to occlude flow, a small clamp around the vessel (e.g. clamp locked in place, e.g. a clamp that is locked in place with a ratchet mechanism, by a latch, or by magnets), magnets that squeeze the tissue between them (e.g. rare earth magnets), a tourniquet mechanism (e.g. a suction cup that creates high pressure between the tissue that is suctioned and can stay in place for several weeks, or twisting tissue to kink the vessel). Additionally, any of the mechanisms could include barbs to provide additional purchase of the tissue and keep the device in place for the desired length of time. Examples include a barbed clip, barbed staple or barbed suture (e.g. Quill SRS by Angiotech Pharmaceuticals). For example, barbs could be used for sutures to secure them in place without requiring knots.

The vessels (e.g. hemorrhoidal arteries) can be sealed by delivering a variety of types of energy to/around the vessel (e.g. hemorrhoidal arteries). For example, radiofrequency energy can be delivered to the vessel, thereby heating the tissue locally, causing the vessel walls to shrink and seal to each other, and thereby occlude blood flow. Various embodiments of an energy-deploying device are depicted in FIGS. 2A, 14A, and elsewhere herein.

Many types of energy can be applied to seal the vessels (e.g. hemorrhoidal arteries), including: radiofrequency electrical energy, bipolar or unipolar diathermy, direct-current electrotherapy. direct heat from a conducting element. For example, a wire/filament can be heated and placed on/near the vessel (e.g. hemorrhoidal artery) or overlying tissue (e.g. mucosa), Cryo (tissue can be cooled to a low enough temperature that it causes tissue damage, and vessel thrombosis), phototherapy, such as with infrared light. For example, infrared light penetrates tissue and heats the underlying structures, causing inflammation and vessel thrombosis. Additional wavelengths of photons can be used, such as ultraviolet. Laser energy can be used, such as photons delivered via a laser to have similar effects as non-laser-based phototherapy. Ultrasound energy can be used, for example HIFU (high frequency ultrasound). Argon beam coagulator energy can be used. Radioactive sources, for example in low dosage, can be used. Combinations of any energy sources listed herein can also be used.

Another embodiment could include a mechanism to occlude flow through the vessel by causing sufficient damage to the vessel through the use of radiation. The radiation can create an area of inflammation that can lead to scaring and necrosis (i.e. death of tissues) that could eliminate flow through the vessels that are targeted. The radiation can several forms such as external beam radiotherapy, stereotactic radiation (e.g. Cyberknife or Gamma Knife), virtual simulation, 3-dimensional conformal radiotherapy, and intensity-modulated radiotherapy, particle therapy, radioisotope therapy (RIT), brachytherapy, or radioimmunotherapy.

Historically, the three main divisions of radiotherapy are external beam radiotherapy (EBRT or XBRT) or teletherapy, brachytherapy or sealed source radiotherapy, and systemic radioisotope therapy or unsealed source radiotherapy. The differences relate to the position of the radiation source; external is outside the body, brachytherapy uses sealed radioactive sources placed precisely in the area under treatment, and systemic radioisotopes are given by infusion or oral ingestion. Brachytherapy can use temporary or permanent placement of radioactive sources. The temporary sources are usually placed by a technique called afterloading. In afterloading a hollow tube or applicator is placed surgically in the organ to be treated, and the sources are loaded into the applicator after the applicator is implanted. This minimizes radiation exposure to health care personnel. Particle therapy is a special case of external beam radiotherapy where the particles are protons or heavier ions. Intraoperative radiotherapy is a special type of radiotherapy that is delivered immediately after surgical removal of the tissue (e.g. vessel, lesion, or cancer). This method has been employed in breast cancer (TARGeted Introperative radioTherapy), brain tumors and rectal cancers.

The radiation source could be from external beam radiotherapy; more specifically it could be from conventional external beam radiotherapy (2DXRT), which is delivered via two-dimensional beams using linear accelerator machines. 2DXRT mainly consists of a single beam of radiation delivered to the patient from several directions: often front or back, and both sides. The word "conventional" refers to the way the treatment is planned or simulated on a specially calibrated diagnostic x-ray machine known as a simulator because it recreates the linear accelerator actions (or sometimes by eye), and to the usually well-established arrangements of the radiation beams to achieve a desired plan. The aim of simulation is to accurately target or localize the volume that is to be treated. This technique is well established and is generally quick and reliable. The worry is that some high-dose treatments may be limited by the radiation toxicity capacity of healthy tissues that lay close to the target (e.g. tissue, vessel, or tumor) volume. An example of this problem is seen in radiation of the prostate gland, where the sensitivity of the adjacent rectum limited the dose that could be safely prescribed using 2DXRT planning to such an extent that tumor control may not be easily achievable. Prior to the invention of the CT, physicians and physicists had limited knowledge about the true radiation dosage delivered to both cancerous and healthy tissue. For this reason, 3-dimensional conformal radiotherapy is becoming the standard treatment for a number of sites (e.g. for tissues, vessels, or tumors). The radiation source could be from stereotactic radiation. Stereotactic radiation is a specialized type of external beam radiation therapy that uses focused radiation beams targeting a well-defined location (e.g. tissue, vessel, or tumor) using extremely detailed imaging scans. Radiation oncologists perform stereotactic treatments, often with the help of a neurosurgeon for tumors in the brain or spine. There are two types of stereotactic radiation. Stereotactic radiosurgery (SRS) is when doctors use a single or several stereotactic radiation treatments, typically for the brain or spine. Stereotactic body radiation therapy (SBRT) refers to one or several stereotactic radiation treatments with the body, such as the lungs. A potential advantage to stereotactic treatments are they deliver the right amount of radiation to the specific location of interest (e.g. tissues, vessels, or cancer) in a shorter amount of time than traditional treatments, which can often take six to 11 weeks. Additionally, treatments are given with extreme accuracy, which should limit the effect of the radiation on healthy tissues. One potential issue with stereotactic treatments is that they are usually only suitable for small volumes of tissues (e.g. vessels or tumors). Stereotactic treatments can be confusing because many hospitals call the treatments by the name of the manufacturer rather than calling it SRS or SBRT. Brand names for these treatments include Axesse, Cyberknife, Gamma Knife, Novalis, Primatom, Synergy, X-Knife, TomoTherapy and Trilogy. This list changes as equipment manufacturers continue to develop new, specialized technologies (e.g. to treat tissues, vessels, or cancers).

The radiation could be from virtual simulation, 3-dimensional conformal radiotherapy, and intensity-modulated radiotherapy. The planning of radiotherapy treatment has been revolutionized by the ability to delineate the tissue of interest (e.g. vessels or tumors) and adjacent normal structures in three dimensions using specialized CT and/or MRI scanners and planning software. Virtual simulation, the most basic form of planning, allows more accurate placement of radiation beams than is possible using conventional X-rays, where soft-tissue structures are often difficult to assess and normal tissues difficult to protect. An enhancement of virtual simulation is 3-Dimensional Conformal Radiotherapy (3DCRT), in which the profile of each radiation beam is shaped to fit the profile of the target from a beam's eye view (BEV) using a multileaf collimator (MLC) and a variable number of beams. When the treatment volume conforms to the shape of the tissue of interest (e.g. vessel, lesion, or tumor), the relative toxicity of radiation to the surrounding normal tissues is reduced, allowing a higher dose of radiation to be delivered to the tissue of interest than conventional techniques would allow. Intensity-modulated radiation therapy (IMRT) is an advanced type of high-precision radiation that is the next generation of 3DCRT. IMRT also improves the ability to conform the treatment volume to concave shapes, for example when the tissue of interest (e.g. vessel, lesion, or tumor) is wrapped around a vulnerable structure such as the spinal cord or a major organ or blood vessel. Computer-controlled x-ray accelerators distribute precise radiation doses to region of interest (e.g. vessel, lesion, malignant tumors, or specific areas within a tumor).

The pattern of radiation delivery is determined using highly-tailored computing applications to perform optimization and treatment simulation (Treatment Planning). The radiation dose is consistent with the 3-D shape of the tumor by controlling, or modulating, the radiation beam's intensity. The radiation dose intensity is elevated near the gross tumor volume while radiation among the neighboring normal tissue is decreased or avoided completely. The customized radiation dose is intended to maximize the dose to the region of interest (e.g. tissue, vessel, lesion, or tumor) while simultaneously protecting the surrounding normal tissue. This may result in better targeting, lessened side effects, and improved treatment outcomes than even 3DCRT. 3DCRT is still used extensively for many body sites but the use of IMRT is growing in more complicated body sites such as CNS, head and neck, prostate, breast and lung. Currently, IMRT is limited by its need for additional time from experienced medical personnel. This is because currently, physicians must manually delineate the regions of interest (e.g. tissues, vessels, lesions, or tumors) one CT image at a time through the entire disease site, which can take much longer than 3DCRT preparation. Then, medical physicists and dosimetrists must be engaged to create a viable treatment plan. Also, the IMRT technology has only been used commercially since the late 1990s even at the most advanced cancer centers, so radiation oncologists who did not learn it as part of their residency program must find additional sources of education before implementing IMRT. Proof of improved benefit from either of these two techniques over conventional radiotherapy (2DXRT) is growing for many tissue sites, but the ability to reduce toxicity is generally accepted. Both techniques enable dose escalation, potentially increasing usefulness. Overconfidence in the accuracy of imaging may increase the chance of missing lesions that are invisible on the planning scans (and therefore not included in the treatment plan) or that move between or during a treatment (for example, due to respiration or inadequate patient immobilization). New techniques are being developed to better control this uncertainty—for example, real-time imaging combined with real-time adjustment of the therapeutic beams. This new technology is called image-guided radiation therapy (IGRT) or four-dimensional radiotherapy. The radiation could be from particle therapy. In particle therapy (aka proton therapy), energetic ionizing particles (protons or carbon ions) are directed at the target tissues (e.g. vessel, lesion, or tumor). The dose increases while the particle penetrates the tissue, up to a maximum (the Bragg peak) that occurs near the end of the particle's range, and it then drops to (almost) zero. The advantage of this energy deposition profile is that less energy is deposited into the healthy tissue surrounding the target tissue.

The radiation could be from radioisotope therapy (RIT). Systemic radioisotope therapy is a form of targeted therapy. Targeting can be due to the chemical properties of the isotope such as radioiodine which is specifically absorbed by the thyroid gland a thousand-fold better than other bodily organs. Targeting can also be achieved by attaching the radioisotope to another molecule or antibody to guide it to the target tissue. The radioisotopes are delivered through infusion (into the bloodstream) or ingestion. Examples are the infusion of metaiodobenzylguanidine (MIBG) to treat neuroblastoma, of oral iodine-131 to treat thyroid cancer or thyrotoxicosis, and of hormone-bound lutetium-177 and yttrium-90 to treat neuroendocrine tumors (peptide receptor radionuclide therapy). Another example is the injection of radioactive glass or resin microspheres into the hepatic artery to radioembolize liver tumors or liver metastases; and this method could be used for example to target any tissue of interest (e.g. hemorrhoidal arteries). Other isotopes commonly used (for example in the treatment of bone metastasis) are strontium-89 and samarium (153Sm) lexidronam.

The radiation could be delivered by the technique of radio-immunotherapy. In 2002, the United States Food and Drug Administration (FDA) approved ibritumomab tiuxetan (Zevalin), which is an anti-CD20 monoclonal antibody conjugated to yttrium-90. In 2003, the FDA approved the tositumomab/iodine (131I) tositumomab regimen (Bexxar), which is a combination of an iodine-131 labeled and an unlabeled anti-CD20 monoclonal antibody. These medications were the first agents of what is known as radioimmunotherapy, and they were approved for the treatment of refractory non-Hodgkins lymphoma. Using this technique, radioactive molecules are delivered through the bloodstream attached to antibodies to the targeted tissue of interest (e.g. vessels, lesions, or tumors). To localize a specific region of interest that does not have a unique antigen, a foreign or unique antigen could be placed in the region of interest (for example by injection).

The radiation could be delivered by the technique known as brachytherapy. Brachytherapy (also known as internal radiotherapy, sealed source radiotherapy, curietherapy or endocurietherapy) is a form of radiotherapy where a radiation source is placed inside or next to the area requiring treatment. Brachytherapy is commonly used as an effective treatment for cervical, prostate, breast, and skin cancer and can also be used to treat tissues (e.g. vessels, lesions, or tumors) in many other body sites. Brachytherapy can be used alone or in combination with other therapies such as surgery, external beam radiotherapy (EBRT) and chemotherapy. In contrast to EBRT, brachytherapy involves the precise placement of radiation sources directly at the site of the region of interest (e.g. tissue, vessel, lesion, or tumor). A key feature of brachytherapy is that the irradiation only affects a very localized area around the radiation sources. Exposure to radiation of healthy tissues further away from the sources is therefore reduced. In addition, if the patient moves or if there is any movement of the region of interest (e.g. tissue, vessel, lesion, or tumor) within the body during treatment, the radiation sources retain their correct position in relation to the region of interest. These characteristics of brachytherapy provide advantages over EBRT—the region of interest can be treated with very high doses of localized radiation, while reducing the probability of unnecessary damage to surrounding healthy tissues. A course of brachytherapy can be completed in less time than other radiotherapy techniques. This can help reduce the chance of surviving cells dividing and growing in the intervals between each radiotherapy dose. Patients typically have to make fewer visits to the radiotherapy clinic compared with EBRT, and the treatment is often performed on an outpatient basis. This makes treatment accessible and convenient for many patients. These features of brachytherapy reflect that most patients are able to tolerate the brachytherapy procedure very well. In addition, brachytherapy is associated with a low risk of serious adverse side effects. Brachytherapy could also be delivered by electronic brachytherapy, which involves placement of miniature low energy x-ray tube sources into a pre-positioned applicator within body cavities (e.g. tissue, vessel, lesion, or tumor) to rapidly deliver high doses to target tissues while maintaining low doses to distant non-target tissues. The commonly used radiation sources (radionuclides) for brachytherapy are: Caesium-137 (137Cs), Cobalt-60 (60Co), Iridium-192 (192Ir), Iodine-125 (125I), Palladium-103 (103Pd), Ruthenium-106 (106Ru).

Radiation therapy can be combined with other mechanisms described here, such as with a mechanical closure device (e.g. clips, staple, suture, etc.) to localize the radiotherapy (e.g. clip with brachytherapy) to the region of interest.

Another way to occlude flow through a vessel (e.g. blood flow in the hemorrhoidal arteries) is to deliver sclerosing agents into or nearby the vessel (e.g. hemorrhoidal arteries). Sclerosing agents are substances that cause tissue irritation, leading to local thrombosis, inflammation, and variable tissue necrosis, fibrosis, and contraction. Sclerosing agents have for many years been injected into the hemorrhoid itself (i.e., the hemorrhoidal cushion or vascular plexus within the hemorrhoid). However, delivering the sclerosing agent in a targeted manner into/around the hemorrhoidal arteries can be more effective, less painful, and produce less collateral damage.

There are many sclerosing agents, including: powders, detergents, acids and bases, boiling water, hypertonic saline, hypertonic glucose, talc, acetic acid, alcohols (e.g., ethanol, isopropanol, methanol, etc), bleomycin, OK-432, Ethibloc, sodium tetradecyl sulfate, phenol oil, vegetable oil, quinine, urea hydrochloride, monoethanolamine oleate, polidocanol, invert sugar, calcium dobesilate, and several other irritating agents and mixtures thereof.

There are various possible methods to deliver the sclerosing agent in order to occlude flow in the vessel (e.g. blood flow in the hemorrhoidal arteries) (in no particular order): 1) Delivery via needles. The sclerosing agent can be directly injected into the lumen of the vessel. One method of direct injection could use a Doppler ultrasound sensor to locate the vessel (e.g. artery), suction to hold the overlying tissue (e.g. mucosa) in place, Doppler to estimate the depth below the surface (e.g. mucosal surface), and moving the needle forward until the tip lies within the vessel lumen. Such a system would be similar to that diagrammed in FIG. 19C. A similar system could be used to deliver the needle tip so that it is within a few millimeters of the vessel (e.g. artery), as sclerosants can occlude the vessel without being placed directly into the vessel's lumen. Additionally, the needle may inject without the use of Doppler guidance or suction to hold the tissue (e.g. mucosa) in place. Multiple needles could be used to simultaneously target multiple vessels (e.g. arteries), or simply to inject enough sclerosant in the vicinity of the vessels (e.g. arteries) to ensure all vessels are sealed off 2) Topical delivery of the sclerosant applied to the overlying tissue (e.g. mucosa). The sclerosant could be held in place by mixing the sclerosant with any of various materials that adhere to the tissue (e.g. mucosa), such as petroleum jelly, cyanoacrylate, etc. 3) Needle-free transmucosal delivery. A variety of needle-free transdermal systems are available for the delivery of drugs transcutaneously. A similar approach can be used on the tissue (e.g. mucosa) overlying the vessel(s) (e.g. hemorrhoidal arteries). The needle-free delivery systems include high-velocity streams of fluid that penetrate the skin/mucosa (e.g. using piezoelectric actuators), creation of micropores on the mucosa (e.g. using electric current), and many more. 4) A suppository pill that is placed into the rectum and elutes the sclerosant.

Another way to occlude flow through a vessel (e.g blood flow in the hemorrhoidal arteries) is to tamponade the vessel (e.g. hemorrhoidal arteries) with chemicals delivered below the tissue (e.g. mucosa), which increase the pressure around the vessel (e.g. hemorrhoidal arteries). For example, a solution of silicone microbeads could be delivered beneath the tissue (e.g. mucosa) at a high enough volume that the pressure in the low tissue layers (e.g. submucosal tissue) increases, since the tissue surface (e.g mucosal surface) can only expand a fixed amount. This increased submucosal pressure could tamponade the vessel(s) (e.g. hemorrhoidal arteries) compressing them sufficiently to occlude flow (e.g. blood flow) and/or induce thrombosis.

Tamponading agents could include: all sclerosing agents as above, saline solutions, bio-compatible injectable bulking agents such as those used in procedures to ameliorate urinary incontinence (carbon-coated microbeads, autologous fat, teflon paste, collagen, silicone elastomer), cyanoacrylate, heterologous tissues (fat, etc) that cause tamponade and/or cause an inflammatory reaction, and similar agents that can remain in the tissue (e.g. submucosa) for a few days. Tamponading agents can be delivered using any of the methods described above for sclerosing agents.

Another embodiment could include a mechanism to occlude flow through the vessel by purposely putting a blocker into the vessel either from a proximal or distal location or directly at the desired location. The blocker could travel spontaneously to the desired location due to the flow within the vessel or the blocker could be placed directly at the desired location by a device such as a wire or catheter that could travel internally in the vessel. The blocker could be expanded to a sufficient size once it was a the desired location, such as, by a balloon that is inflated or by a absorbent material that when put in contact with liquid (such as liquid with a vessel) expands to a larger desired size, or it could be expanded in a larger caliber vessel and moved to a smaller caliber vessel such that it occluded flow past the blocker. The blocker could be an embolizing agent that is introduced (for example by a needle or catheter) into the vessel at a location that is proximal (with orientation to flow) to the desired site of occlusion. The blocker could, for example, be inserted into the vessel directly through the rectum or through a catheter in, for example, the femoral artery). The blocker could be an embolizing agent made out of various compounds, including, but not limited to, liquid embolic agents (these are used for ateriovenous malformations (AVMs). These agents are able to flow through complex vascular structures so the surgeon does not need to target his catheter to every single vessel.), nbca (n-butyle-2-cyanoacrylate) (This agent is a permanent rapidly acting liquid that will polymerize immediately on contact with ions, aka superglue. It also has an exothermic reaction that destroys the vessel wall. Since the polymerization is so rapid, it requires skill of the surgeon when using. During the procedure, the surgeon must flush the catheter before and after injecting the nbca or the agent will polymerize within the catheter. Also the catheter must be withdrawn quickly or it will be stuck to the vessel. Oil can be mixed with nbca to slow the rate of polymerization.), ethiodol (This is made from iodine and poppyseed oil, and is a highly viscous agent. It is usually used for chemembolizations, especially for hepatomas. This is because these types of tumors have a characteristic of absorbing iodine. Half life is 5 days so it only temporarily embolizes vessels.), sclerosing agents (These will harden the endothelial lining of vessels. They have been around for a long time and need more time to react than the liquid embolic agents. Therefore, they are less appropriate for high flow vessels or large vessels.), ethanol (This permanent agent is very good for treating AVMs. The alcohol does need some time to denaturize proteins of the endothelium and activate the coagulation system which causes a blood clot. Therefore, some surgeons will use a balloon occlusion catheter to stop the blood flow and allow time for ethanol to work. The disadvantage of this is that it is toxic to the system in large quantities and may cause compartment syndrome, and additionally, the injections are painful.), ethanolamine oleate (This permanent agent is used for sclerosing esophageal varices. It is made of 2% benzyl alcohol so it is less painful than ethanol. However, it does cause hemolysis and renal failure in large doses.), sotradecol (This agent is used for superficial lower extremity varicose veins. It has been around for a very long time and is a proven remedy. However, it does cause hyperpigmentation of the region in 30% of patients. It is less painful than ethanol.), particulate embolic agents (These agents are typically used for precapillary arterioles or small arteries. These are also very good for AVMs deep within the body. The disadvantage is that they are not easily targeted in the vessel. None of these are radioopaque so it makes radiologic imaging difficult to see them unless they were soaked in contrast prior to injection.), gelfoam (This agent temporarily occludes vessels for 5 weeks. They work by absorbing liquid and plugging up the vessel. These are water insoluble gelatin so the particles may travel distally and occlude smaller capillaries. A way to localize the injection of gelfoam is to make a gelfoam sandwich. A coil is placed at a precise location, then gelfoam is injected and lodged into the coil.), polyvinyl alcohol (PVA) (These are permanent agents. They are tiny balls 50-1200 micrometers in size. The particles are not meant to mechanically occlude a vessel. Instead they cause an inflammatory reaction. They have a tendency to clump together since the balls are not perfectly round. The clump can separate a few days later failing as an embolic agent.), acrylic gelatin microspheres (This is a superior form of permanent particulate embolic agent. They are similar to PVA but they are perfectly round, thus they do not clump together. The balls are fragile so they may crack inside small catheters.), mechanical occlusion devices (These fit in all vessels, and have the advantage of accuracy of location as they are deployed exactly where the catheter ends.), coils (These are often used for ateriovenous fistulas (AVFs), aneurysms, or trauma. They are very good for fast flowing vessels because they immediately clot the vessel. They are usually made from platinum or stainless steel, and they induce clot because of the dacron wool tails around the wire. The coil itself will not cause mechanical occlusion. Because it is made of metal, it is easily seen in radiographic images. The disadvantage is that large coils can disrupt the radiographic image. The coil may also lose its shape if the catheter is kinked. There is a small risk of dislodging from the deployed location.), and/or a detachable balloon (These are used to treat AVFs and aneurysms. These balloons are simply implanted in a target vessel then filled with saline through a one-way valve. The blood stops and endothelium grows around the balloon until the vessel fibroses. The balloon may be hypertonic relative to blood and cause the balloon to rupture and fail, or the balloon may be hypotonic and cause the balloon to shrink and migrate somewhere else.)

The vessel(s) (e.g. hemorrhoidal arteries) can be sealed by locally delivering a variety of drugs. These drugs can work by any of the following actions: induce intra-arterial coagulation, induce contraction or spasm of the arterial wall, etc. These drugs can include Fibrin, Thrombin, Alpha-1-adrenergic agonists such as phenylephrine, Epinephrine, Prostacyclin pathway inhibitors, Nitric oxide pathway inhibitors, 5-HT pathway activators, TXA-2 pathway activators, Calcium channel activators, Ethanol, Interferon, Cocaine, Amphetamine, Ergot derivatives (e.g., ergotamine). These drugs can be delivered via any of the mechanisms described for sclerosing agents above.

In any of the processes used to seal the vessel (e.g. hemorrhoidal artery), it may be advantageous to hold the overlying tissue (e.g. mucosa) in place during the procedure (hereafter referred to as "mucosal fixation"). For example, in FIG. 19C, a suction cup is used to hold the mucosa in place while a needle is delivered into the hemorrhoidal artery to seal it with steam. In this case, mucosal fixation is provided by a vacuum created in a suction cup that prevents the mucosal and vessel (e.g. hemorrhoidal artery) from moving out of position during placement of the needle. Mucosal fixation is useful because the mucosa is slippery, billowy, and elastic, and because the underlying vessel (e.g. hemorrhoidal artery) is able to move around under the mucosal surface.

Mucosal fixation techniques include (in no particular order): 1) Suction of the tissue surface (e.g. mucosal surface) with a suction cup that creates a vacuum between the suction cup and tissue surface (e.g. mucosal surface). Our tests suggest that the port size on the suction cup that works well is a circular (or elliptical) port that has a diameter of 0.5-3 cm, or more narrowly 0.5-2 cm, or more narrowly 0.5-1 cm. 2) A port that is shaped such that the mucosal evaginates into the port. For example, a port that is conically-shaped would cause the compliant mucosa to form a cone shape that might not slip away as easily. The port artery sealing mechanism (e.g. RF) could be positioned near/in the port. 3) Movable hooks to grab the mucosa. These hooks could be shaped like curved suture needles, have barbs, serrated edges, have adhesive on them, and more. The hooks can be retractable, steerable, and more. 4) Pressing against the tissue (e.g. mucosa) firmly with a force orthogonal to the plane of the tissue surface (e.g. mucosal surface). Pressing against the tissue (e.g. mucosal wall) could be done by having the operator press against, for example, the rectal wall with the device, or having an actuating mechanism on the device which allows the device to create its own force against the rectal wall. 5) An adhesive. Adhesives include tissue glue (e.g. cyanoacrylate), dry materials that wick up moisture from the mucosa (e.g. Whatman filter paper), and more. These adhesives could be selectively inactivated (e.g. applying a jet of water to the Whatman filter paper).

In order for a device (e.g. transanal device) to seal a vessel (e.g. the hemorrhoidal arteries), it could be useful to have a feature of the device that allows the vessel-sealing end of the device to easily navigate around a bulk of tissue (e.g. the bulk of the hemorrhoid). Many hemorrhoids are very large and bulky, and external pressure on the hemorrhoid can cause pain. Therefore, it can be difficult to insert a device into the anus of a conscious patient without causing pain.

To minimize the amount of pressure exerted on the hemorrhoid and anus by inserting this device, there are various features that can be included. One method is to have the vessel-sealing end of the device (e.g. the region of the device with the clip-applier or vessel-sealing energy source) distal to a bend/angle in the device. For example, FIG. 1A shows a device with an angled bend between the handle and vessel-sealing ends of the device. The angle between these two ends can be a fixed angle, with the angle (between the two arms) approximately 90 to 180 degrees, more narrowly [135 to 170 degrees], more narrowly [135 to 165 degrees], for example [150 to 165 degrees].

This bend/angle can be adjustable (having similar angle ranges to those listed for fixed angle). The angle can be adjusted either with a dial/slider on the device, by having the operator hand-bend a malleable joint, etc. This angle can be adjusted before and/or during the treatment procedure (e.g. hemorrhoids treatment procedure). The internal mechanism for controlling the bend could include pulling on a guidewire that lies in an internal shaft of the device and that is inserted into the vessel-sealing end of the device.

There can be multiple bends/angles between the handle and vessel-sealing ends of the device.

Another method is to place between the handle and vessel-sealing end of the device a shaft that is curved. The curvature of this shaft can be any series of smooth curves. The exact curvature can be selected based on actual tissue measurements (e.g. hemorrhoid measurements) in humans. For example, the curvature could just be a smooth curve taking the angles mentioned above for a fixed angle/bend. This curved shaft can be malleable, so the operator can inspect a patient's anus and hemorrhoids and pre-bend the shaft so that it will easily arc around the patient's hemorrhoids without exerting much pressure on the hemorrhoids.

FIGS. 35A through 35C shows a method for pexying prolapsed tissue (e.g. hemorrhoids) using a support attachment, especially after vessels (e.g. hemorrhoidal arteries) are ligated. Said support attachment consists of an adhesive ring member on the proximal circumferential end of the support attachment. Distal to the adhesive ring member is an elastic tubular member that wraps around and supports the prolapsed hemorrhoid. The elastic tubular member can be constructed from elastomeric membrane such as polyurethane, latex, or can be a mesh made from the same materials. Said tubular member in its un-stretched configuration will be of smaller volume and longitudinal length as compared to the tissue of interest (e.g. prolapsed hemorrhoids).

The support attachment can be deployed from an endoscope or a handheld device similar to the embodiment described in FIG. 3. The adhesive circumference proximal end, when deployed, will adhere to the anal wall around the base of the tissue (e.g. prolapsed hemorrhoid). Said tissue (e.g. prolapsed hemorrhoid) will be compactly wrapped and supported by the tubular elastic member as shown in FIG. S6-B. Additionally, the tubular elastic member applies pressure on the tissue (e.g. prolapsed hemorrhoid) proximally toward the anal wall and will promote the tissue (e.g. prolapsed hemorrhoids) to retract, as shown in FIG. S6-C. Said support attachment is particularly useful in promoting recovery especially after vessel closure (e.g. hemorrhoidal Dearterialization) is performed by inventions disclosed in this application. Recovery is promoted because the tissue (e.g.

prolapsed hemorrhoids) when pexy-ed in place will reduce strain to the vessel(s) (e.g. hemorrhoidal vasculature) and/or supporting tissues (e.g. hemorrhoidal supporting muscles) during strain on the tissue, for example, during a bowel movement, consequently preventing further damage and worsening of the condition. Disclosed support attachment can also be used as a stand-alone (instead of a post-op) treatment if desired by the physician.

FIG. 36A through 36C shows a variation of a support attachment (e.g. hemorrhoids support attachment). Instead of an adhesive and elastic tubular member as described in FIG. 35A through 35C, a shape-memory coil, constructed from shape memory wires such as Nitinol, can be attached to the tissue (e.g. prolapsed hemorrhoid(s)). The shape-memory support coil is pre-heated and shaped into a spiral coil that will be able to attach itself through axial pressure (pinching motion) to the tissue (e.g. prolapsed hemorrhoids). As the coil is configured to remain flat (FIG. 36A) in its un-stretched position, the coil when applied to the tissue (e.g. a prolapsed hemorrhoid) is able to guide and promote the tissue (e.g. prolapsed hemorrhoid) to retract proximally towards the wall (e.g. anal wall). Similar to the support attachment in FIGS. 35B and 35C, the shape-memory support coil will promote recovery and can be deployed from an endoscope or a handheld device as described in FIG. 3, after procedure (e.g. hemorrhoidal dearterialization procedure) is performed, or as a stand-alone treatment as desired by the physician. The axial pressure (pinching effect) generated by the shape-memory support coil will provide additional forces to ligate vessels (e.g. arteries) feeding the tissue (e.g. prolapsed hemorrhoid).

Any of the above embodiments (e.g. clip, staple, rubberband, suture, etc.) could be made wholly or partially out of bio-absorbable (resorbable) materials. Bio-absorbable materials slowly degrade inside the body. Examples of bio-absorbable materials that could be used include, but are not limited to: ethenylbenzene (e.g. Lactomer™ absorbable copolymer, e.g. Poly Surgiclip™ by Covidien), catgut (plain or chormic), polyglycolic acid (e.g. Dexon), polyglactin (e.g. Vicryl), polydioxanone (PDS) (e.g. ABSOLOK EXTRA Single Clip by Ethicon), polyglyconate (e.g. Maxon), or Purasorb (by Purac Biomaterials).

An additional feature that could be included with any of the previously described embodiments could be a method to decrease any pain or discomfort. Different methods that could be used to minimize pain include, but are not limited to, cooling the tissues of interest, a pudendal nerve block (e.g. an injection, plug, or implant), an epidural or spinal block, or using local anesthetics to the tissues of interest such as esters (e.g. Procaine, Benzocaine, Chloroprocaine, Cocaine, Cyclomethycaine, Dimethocaine/Larocaine, Propoxycaine, Procaine/Novocaine, Proparacaine, or Tetracaine/Amethocaine), amides (e.g. Lidocaine, Articaine, Bupivacaine, Cinchocaine/Dibucaine, Etidocaine, Levobupivacaine, Lidocaine/Lignocaine, Mepivacaine, Piperocaine, Prilocaine, Ropivacaine, or Trimecaine), combinations (e.g. Lidocaine/prilocaine (EMLA)), or natural local anesthetics (e.g. Saxitoxin or Tetrodotoxin). Other methods to decrease pain in the region of interest include injection of botox (as anti-spasmodic), an implantable anesthetic or anesthetic delivery device, anti-inflammatory drugs (e.g. Tylenol or NSAIDs), injection of a toxin (e.g. spider venom) to digest the area of the nerve, destruction of the nerves by radiofrequency ablation, electricity, ice, or capsacin, injection of the painkiller used by mosquitoes, a stimulation probe to build tolerance, reducing pain receptors (e.g. anti-opiate or Narcan), or injection of a collagen cross link in the tissue (e.g. to push nerves away from tissue edge).

An additional feature that could be included with any of the previously described embodiments could be a method to prevent prolapse. This could be a sleeve around the anus to prevent or reduce shearing forces. The sleeve could be held in place, for example, by a device fixed to the pelvic inlet. Alternatively, it could be lubricating stool and the rectal wall, fiber for softer stool, nitroglycerin, or creating a second skin over the hemorrhoid.

An additional feature that could be included with any of the previously described embodiments could be a method to prevent recurrent prolapse (protrusion of tissue, for example, prolapse of hemorrhoids). The method to prevent recurrence of prolapse could be to either strengthen the tissues (e.g. with electro-stimulation or injection of a strengthening agent, more specifically a sclerosing agent), or by fixation of the tissue (e.g. by using a band (e.g. rubberband), stent, glue, or adhesive.

An additional feature that could be included with any of the previously described embodiments could be a method to tack the tissue of interest (e.g. hemorrhoid) in place by inverting and stapling or clipping the tissue (e.g. hemorrhoid) upwards, creating tissue fold to reduce tissue redundancy (e.g. by suturing tissue upwards), inserting an implant in the tissue to reduce redundancy, using liposuction tools to reduce tissue redundancy and pull up or tighten the tissue of interest (e.g. hemorrhoids), creating new suspensory ligaments, or injecting a sheet under the tissue (e.g. mucosa) to tighten the tissue.

An additional feature that could be included with any of the previously described embodiments could be a method to correct an engorged plexus (e.g. hemorrhoid or hemorrhoidal plexus). This could be achieved by injecting a cross-linking agent, using heat (e.g. steam) to tighten tissues (e.g. hemorrhoids), pexy (e.g. anopexy or mucopexy) to lift the tissues (e.g. hemorrhoids), deflating the vein via suction, a mesh or net around the hemorrhoids, rubberband support and spikes to drain blood from hemorrhoids, injection of sclerosing agents (e.g. ethanol) or lipids into the vein (e.g. hemorrhoidal veins), or stent to push hemorrhoids back in place (e.g. barbs on a stent, spring on a stent, or drugs on a stent (e.g. fenoafern or injection ports for drug delivery).

An additional feature that could be included with any of the previously described embodiments could be a method to block the blood supply. This could be achieved by an expanding ring pressing on or above the tissue of interest (e.g. hemorrhoids), a valve in the artery or vein or funnel in the artery or vein to decrease blood supply, injecting thrombin or gel foam into the blood stream of the tissue of interest, suction to the tissue of interest, ablation of the arteries or veins with an probe using, for example, energy, for example UV light, near infrared light, or argon beam, or laser therapy.

This device could be used for several different medical purposes, such as ligation of vessels (such as arteries, veins, or lymphatics), ducts, sinus tracts, and fistulae. More specifically it could be used to ligate vessels hard to reach locations, or locations where it is difficult to locate the vessel, such as in the gastrointestinal tract, more specifically it could be used to ligate hemorrhoidal (or rectal) arteries (or varices) or esophageal varices. Other medical problems this device could be used for include, but are not limited to, endoscopic procedures (for example: to ligate vessels in and around bleeding ulcers, such as gastric ulcers, duodenal ulcers, and marginal ulcers (from anastomoses), to ligate esophageal, gastric, or rectal (hemorrhoidal) varices, to stop bleeding from bleeding vessels the small bowel (for example from AVMs), to ligate bleeding vessels the colon (for example from angiodysplasia, bleeding diverticulae, or rectal or hemorrhoidal varices), endoscopic marking, closure of mucosectomy (for example for cancer or a suspicious lesion), closure of a perforation (for example, caused by endoscopy), for diverticular disease (for example, for closure of diverticulum, or to stop bleeding from diverticular disease), to perform a polypectomy (ligation of polyps), as an anchoring (for example, to fix jejunal feeding tube to the wall of the small bowel).) The device could be used for surgical procedures, such as for a neck dissection (for example for ligation of vessels or lymph nodes), lymph node dissection (for example in the breast, neck, or in the groin), for gynecological procedures, such as uterine artery ligation for the treatment of uterine fibroid disease, for bleeding following a Caesarean section, for fallopian tubal ligation, for urological procedures, such as vasectomy (for example for the purpose of ligating a structure and specifically avoiding ligation of a vessel), for closure of urine leaks from kidneys, ureters, bladder, and/or urethra, for ligation of vessels (such as lacerated arteries and/or veins) in trauma situations (for example to stop rapid arterial bleeding without isolating the artery, more specifically to enable those untrained in medicine to stop bleeding in the field), to stop bleeding from AVMs, to close an aneurysm (for example for small aneurysm sacs), for closure of arteries (such as hemorhhoidal arteries, the gastroduodenal artery, and/or bleeding ulcers), for closure of veins (such as veins in the esophagus), for closure of lymphatic vessels (such as the lymphatic duct, lymph vessels causing a lymphocele, and/or lymph nodes), for closure of ducts, such as the pancreatic duct, biliary ducts (for example for post-surgical leaks, for example the cystic duct, intra- or extra-hepatic ducts, common hepatic duct, and or common bile duct), sebaceous ducts, mucous ducts, and/or salivary ducts, closure of sinus tracts, closure of fistulae, such as vascular fistulae and/or enteric fistulae, for aneurysms (for example aneurysms in the brain, aorta, iliac, femoral, popliteal artery, or other peripheral artery), for venous aneurysms (for example, popliteal vein aneurysms). It could also be use for closure of airways (e.g. bronchi airways, e.g. for air leaks).

The devices and methods disclosed here can effectively treat hemorrhoids with minimal pain. The device is minimally invasive and can involve no cutting, suturing, and extensive anal dilation. The device can require only 1.5 cm dilation of the anus (the same as a finger exam of the rectum) and the use of precision energy delivery to collapse the targeted arteries.

The methods described herein can be performed in a clinic or office. The methods described are minimally invasive and do not require anesthesia (which requires previously existing treatments to be performed in the operating room (OR), which is typically more expensive).

The devices and methods described herein can be usable by gastroenterologists. Gastroenterologists currently diagnose hemorrhoids but are unable to effectively treat the hemorrhoids because they lack the necessary tools.

Many patients do not receive treatment because they fear the painful treatments, or get lost in the referral chain. The devices and methods described herein can expand the treated population by providing an effective treatment that is painless and can be performed by the physicians who first diagnose the hemorrhoids.

The devices and methods described herein will effectively treat hemorrhoids with minimal procedural and post-procedural pain. The devices and methods herein improve upon HD in several respects: the massive anal dilation (>6 cm) required by HD causes severe anal fissures (tears) in 4% of patients, while our invention requires minimal dilation (1.5 cm); the presently disclosed procedure can be performed by gastroenterologists and will allows a much faster and easier procedure. The device has the efficacy and minimal pain of HD.

Alternative or in addition to the use of ultrasound Doppler sensors, detection of submucosal arterial segments with internal blood flow can also be accomplished using a number of other sensors, which can be incorporated into or used in conjunction with the inventions described in this document.

The sensor can be laser Doppler flowmetry. The patient can receive intravenous indocyanine green dye, followed by detection of the arteries by near-infrared video angiography. The arteries can be detected by measuring absorption of electromagnetic energy from the mucosa. Several wavelength bands should suffice for submucosal arterial detection, such as infrared which is well absorbed by blood vessels. Fourth, the sensor can use multiple wavelength bands of electromagnetic energy to differentiate arteries from veins. Oxygenated hemoglobin absorbs more light at 910 nm and deoxygenated hemoglobin absorbs more light at 660 nm. By comparing absorption at these wavelengths it is possible to differentiate veins from arteries. Including dopper ultrasound sensors, a combination of any of the above sensors can also be used to detect submucosal arterial segments with internal blood flow, in conjunction with or incorporated into inventions described in this document.

Any or all elements of the clips, clamps, staples, stents, or other implantable devices or tools for delivering the treating devices or directly treating hemorrhoids disclosed herein (collectively the "treatment devices") and/or other devices or apparatuses described herein can be made from, for example, a single or multiple stainless steel alloys, nickel titanium alloys (e.g., Nitinol), cobalt-chrome alloys (e.g., ELGILOY® from Elgin Specialty Metals, Elgin, Ill.; CONICHROME® from Carpenter Metals Corp., Wyomissing, Pa.), nickel-cobalt alloys (e.g., MP35N® from Magellan Industrial Trading Company, Inc., Westport, Conn.), molybdenum alloys (e.g., molybdenum TZM alloy, for example as disclosed in International Pub. No. WO 03/082363 A2, published 9 Oct. 2003, which is herein incorporated by reference in its entirety), tungsten-rhenium alloys, for example, as disclosed in International Pub. No. WO 03/082363, polymers such as polyethylene teraphathalate (PET)/polyester (e.g., DACRON® from E. I. Du Pont de Nemours and Company, Wilmington, Del.), polypropylene, (PET), polytetrafluoroethylene (PTFE), expanded PTFE (ePTFE), polyether ketone (PEK), polyether ether ketone (PEEK), poly ether ketone ketone (PEKK) (also poly aryl ether ketone ketone), nylon, polyether-block co-polyamide polymers (e.g., PEBAX® from ATOFINA, Paris, France), aliphatic polyether polyurethanes (e.g., TECOFLEX® from Thermedics Polymer Products, Wilmington, Mass.), polyvinyl chloride (PVC), polyurethane, thermoplastic, fluorinated ethylene propylene (FEP), absorbable or resorbable polymers such as polyglycolic acid (PGA), polylactic acid (PLA), polycaprolactone (PCL), polyethyl acrylate (PEA), polydioxanone (PDS), and pseudo-polyamino tyrosine-based acids, extruded collagen, silicone, zinc, echogenic, radioactive, radiopaque materials, a biomaterial (e.g., cadaver tissue, collagen, allograft, autograft, xenograft, bone cement, morselized bone, osteogenic powder, beads of bone) any of the other materials listed herein or combinations thereof. Examples of radiopaque materials are barium sulfate, zinc oxide, titanium, stainless steel, nickel-titanium alloys, tantalum and gold.

Any or all elements of the treatment devices and/or other devices or apparatuses described herein, can be, have, and/or be completely or partially coated with agents and/or a matrix for cell ingrowth or used with a fabric, for example a covering (not shown) that acts as a matrix for cell ingrowth. The matrix and/or fabric can be, for example, polyester (e.g., DACRON® from E. I. Du Pont de Nemours and Company, Wilmington, Del.), polypropylene, PTFE, ePTFE, nylon, extruded collagen, silicone or combinations thereof.

The treatment devices and/or elements of the treatment devices and/or other devices or apparatuses described herein and/or the fabric can be filled, coated, layered and/or otherwise made with and/or from cements, fillers, glues, and/or an agent delivery matrix known to one having ordinary skill in the art and/or a therapeutic and/or diagnostic agent. Any of these cements and/or fillers and/or glues can be osteogenic and osteoinductive growth factors.

Examples of such cements and/or fillers includes bone chips, demineralized bone matrix (DBM), calcium sulfate, coralline hydroxyapatite, biocoral, tricalcium phosphate, calcium phosphate, polymethyl methacrylate (PMMA), biodegradable ceramics, bioactive glasses, hyaluronic acid, lactoferrin, bone morphogenic proteins (BMPs) such as recombinant human bone morphogenetic proteins (rhBMPs), other materials described herein, or combinations thereof.

The agents within these matrices can include any agent disclosed herein or combinations thereof, including radioactive materials; radiopaque materials; cytogenic agents; cytotoxic agents; cytostatic agents; thrombogenic agents, for example polyurethane, cellulose acetate polymer mixed with bismuth trioxide, and ethylene vinyl alcohol; lubricious, hydrophilic materials; phosphor cholene; anti-inflammatory agents, for example non-steroidal anti-inflammatories (NSAIDs) such as cyclooxygenase-1 (COX-1) inhibitors (e.g., acetylsalicylic acid, for example ASPIRIN® from Bayer AG, Leverkusen, Germany; ibuprofen, for example ADVIL® from Wyeth, Collegeville, Pa.; indomethacin; mefenamic acid), COX-2 inhibitors (e.g., VIOXX® from Merck & Co., Inc., Whitehouse Station, N.J.; CELEBREX® from Pharmacia Corp., Peapack, N.J.; COX-1 inhibitors); immunosuppressive agents, for example Sirolimus (RAPAMUNE®, from Wyeth, Collegeville, Pa.), or matrix metalloproteinase (MMP) inhibitors (e.g., tetracycline and tetracycline derivatives) that act early within the pathways of an inflammatory response. Examples of other agents are provided in Walton et al, Inhibition of Prostoglandin $E_2$ Synthesis in Abdominal Aortic Aneurysms, *Circulation*, Jul. 6, 1999, 48-54; Tambiah et al, Provocation of Experimental Aortic Inflammation Mediators and Chlamydia Pneumoniae, *Brit. J. Surgery* 88 (7), 935-940; Franklin et al, Uptake of Tetracycline by Aortic Aneurysm Wall and Its Effect on Inflammation and Proteolysis, *Brit. J. Surgery* 86 (6), 771-775; Xu et al, Sp1 Increases Expression of Cyclooxygenase-2 in Hypoxic Vascular Endothelium, *J. Biological Chemistry* 275 (32) 24583-24589; and Pyo et al, Targeted Gene Disruption of Matrix Metalloproteinase-9 (Gelatinase B) Suppresses Development of Experimental Abdominal Aortic Aneurysms, *J. Clinical Investigation* 105 (11), 1641-1649 which are all incorporated by reference in their entireties.

"Automated" or "automatedly" herein refers to controlling a device to perform the function desired. Automatic implies that the operators hands have no direct mechanical control over the tool. The operator of an automated tool can press a button, a lever, knob, and/or use other controls to control a working element, but does not have a grasp on the working element performing the resulting action itself.

"Remote" or "remotely" herein refers to controlling a device away from the target site. Notably, remotely using a device ligating hemorrhoids in the rectum means that the device is controlled by elements operated by the user outside of the rectum.

"Immobilizing" herein refers to actively holding steady, not merely being placed next to a loose object or tissue that may continue to move about.

"Ligating" herein refers to a method of stopping flow within a lumen. Ligating can include, but is not limited to, mechanical constriction or otherwise compressing or tamponading, sclerosing, ablating, or combinations thereof.

The devices and methods discussed above are not limited to certain treatments or regions of the body, but may include any number of other treatments and areas of the body. Modification of the above-described methods and devices for carrying out the invention, and variations of aspects of the invention that are obvious to those of skill in the arts are intended to be within the scope of this disclosure. Any elements described herein as singular can be pluralized (i.e., anything described as "one" can be more than one). Any species element of a genus element can have the characteristics or elements of any other species element of that genus. The above-described configurations, elements or complete assemblies and methods and their elements for carrying out the invention, and variations of aspects of the invention can be combined and modified with each other in any combination. Moreover, various combinations of aspects between examples are also contemplated and are considered to be within the scope of this disclosure as well.

We claim:

1. An apparatus for ligating a hemorrhoidal blood vessel for treatment of hemorrhoids comprising:
    a housing extending along a longitudinal axis and having a distal end insertable into the rectum;
    an ultrasound sensor coupled to the distal end of the housing and configured to detect blood flow of a hemorrhoidal blood vessel;
    a suction channel having a distal end located at the distal end of the housing;
    a suction port at the distal end of the suction channel that receives through suction a tissue segment containing at least a portion of the hemorrhoidal blood vessel, the suction port located at a fixed longitudinal position along the longitudinal axis in relation to the ultrasound sensor; and
    a compression clip, proximate to the suction port and having two clip arms displaceable from each other, wherein the compression clip has an open configuration within the housing and a closed configuration and is biased in the closed configuration, and wherein the compression clip is deployable in the open configuration and configured to close and compress the tissue segment.

2. The apparatus of claim 1, wherein the clip arms angularly close when deployed.

3. The apparatus of claim 2, wherein the compression clip includes internally opposing jaws coupled to the clip arms.

4. The apparatus of claim 3, wherein at least one of the jaws includes a prong internally opposed to the other jaw.

5. The apparatus of claim 3, wherein both jaws include teeth.

6. The apparatus of claim 1, wherein the compression clip is biased closed and held open until deployment.

7. The apparatus of claim 1, wherein the suction port is retractable into the housing.

8. The apparatus of claim 7, wherein the suction port is further extendable from the housing.

9. The apparatus of claim 1, wherein the ultrasound sensor includes a Doppler sensor.

10. A method for ligating a hemorrhoidal blood vessel for treatment of hemorrhoids, comprising:

inserting a device having a housing extending along a longitudinal axis, an ultrasound sensor, a suction port, the suction port located at a fixed longitudinal position along the longitudinal axis in relation to the ultrasound sensor, and a compression clip in an open configuration into the rectum;

moving the ultrasound sensor along the surface of tissue in the rectum;

detecting a hemorrhoidal blood vessel in the tissue with the ultrasound sensor;

creating a tissue mound including at least a portion of the hemorrhoidal blood vessel; and deploying the compression clip in the open configuration such that the compression clip moves toward a closed configuration to compress at least a portion of the tissue mound to stop blood flow through the hemorrhoidal blood vessel.

11. The method of claim 10, wherein deploying the compression clip includes deploying the compression clip to compress a hemorrhoidal artery.

12. The method of claim 10, wherein creating a tissue mound includes applying suction to the tissue in a suction direction and receiving the tissue mound in the device.

13. The method of claim 12, wherein receiving the tissue mound in the device includes receiving the tissue mound in a suction port and retracting the suction port into the device.

14. The method of claim 10, wherein deploying the compression clip includes deploying a pair of clip arms to close around at least a portion of the hemorrhoidal blood vessel.

15. The method of claim 14, wherein deploying a pair of clip arms includes compressing the hemorrhoidal blood vessel between two internally opposing jaws.

16. The method of claim 10, wherein the compression clip comprises a pair of opposing jaws spaced apart from one another in the open configuration and wherein deploying the compression clip comprises compressing the hemorrhoidal blood vessel between the opposing jaws.

* * * * *